United States Patent
See et al.

(10) Patent No.: US 9,622,835 B2
(45) Date of Patent: Apr. 18, 2017

(54) ORTHODONTIC DIGITAL SETUPS

(71) Applicant: 3M INNOVATIVE PROPERTIES COMPANY, St. Paul, MN (US)

(72) Inventors: Peter See, Berlin (DE); Richard E. Raby, Lino Lakes, MN (US); Nicholas A. Stark, Woodbury, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 14/528,966

(22) Filed: Oct. 30, 2014

(65) Prior Publication Data
US 2015/0057983 A1 Feb. 26, 2015

Related U.S. Application Data

(62) Division of application No. 14/000,151, filed as application No. PCT/US2012/025605 on Feb. 17, 2012, now Pat. No. 8,897,902.
(Continued)

(51) Int. Cl.
*A61K 6/00* (2006.01)
*A61C 1/00* (2006.01)
(Continued)

(52) U.S. Cl.
CPC .............. *A61C 7/002* (2013.01); *G06F 19/12* (2013.01); *G06T 19/00* (2013.01);
(Continued)

(58) Field of Classification Search
CPC ..... A61C 7/002; A61C 2007/004; A61C 1/00; A61C 13/00; A61C 13/004; A61C 13/12;
(Continued)

(56) References Cited

U.S. PATENT DOCUMENTS 6,512,994 B1 *  1/2003  Sachdeva .................... 702/167
6,688,886 B2   2/2004  Hughes
(Continued)

FOREIGN PATENT DOCUMENTS

CN    101284302 A    10/2008
CN    101310964      11/2008
(Continued)

OTHER PUBLICATIONS

Dr. Lawrence F. Andrew, Straight Wire, The Concept and Appliance, "Six Keys to Optimal Occlusion", (L. A. Wells, 1989) Chapter 3, pp. 13-24.
(Continued)

*Primary Examiner* — Ronald Hartman, Jr.

(57) ABSTRACT

Methods for recognizing a virtual tooth surface, defining a virtual tooth coordinate system, and simulating a collision between virtual teeth are provided. Methods include receiving input data specifying a point on the rendered surface model associated with a tooth, deriving a perimeter on the surface model of the tooth based on the input data, and analyzing the surface model along a plurality of paths outwardly extending from points on the perimeter along the three-dimensional surface to produce gingival margin data. Methods also include receiving point input data that defines a point on the virtual tooth, receiving axis input data that defines first and second axes associated with the virtual tooth, computing a substantially normal vector for a portion of the tooth surface surrounding the point, and computing a coordinate system based on the axis input and the computed vector. Methods also include receiving permissible movement input data directed to permissible movement of a first virtual tooth, simulating, in three dimensional space, bringing the first virtual tooth into contact with a second virtual tooth while constraining movement of the first virtual tooth
(Continued)

based on the permissible movement input data, and displaying data resulting from the simulation.

20 Claims, 43 Drawing Sheets

Related U.S. Application Data

(60) Provisional application No. 61/444,644, filed on Feb. 18, 2011.

(51) Int. Cl.
| | |
|---|---|
| *A61C 13/00* | (2006.01) |
| *A61C 13/12* | (2006.01) |
| *A61C 8/00* | (2006.01) |
| *A61C 7/00* | (2006.01) |
| *G06T 19/00* | (2011.01) |
| *G06F 19/12* | (2011.01) |
| *G06F 19/00* | (2011.01) |

(52) U.S. Cl.
CPC .... *A61C 2007/004* (2013.01); *G06F 19/3437* (2013.01); *G06T 2210/41* (2013.01)

(58) Field of Classification Search
CPC ....... A61C 8/00; A61C 9/0046; A61C 9/0053; A61C 13/006; G06F 19/12; G06F 19/3437; G06T 19/00; G06T 2210/41; A61K 6/00
USPC ..... 433/24, 201.1, 213, 214; 700/56, 97, 98, 700/117
See application file for complete search history.

(56) References Cited

U.S. PATENT DOCUMENTS

| | | | |
|---|---|---|---|
| 6,733,289 B2* | 5/2004 | Manemann et al. ............ 433/24 |
| 7,155,373 B2* | 12/2006 | Jordan et al. .................... 703/1 |
| 7,156,661 B2* | 1/2007 | Choi et al. ................... 433/213 |
| 7,210,929 B2 | 5/2007 | Raby |
| 7,291,011 B2 | 11/2007 | Stark |
| 7,354,268 B2 | 4/2008 | Raby |
| 7,361,018 B2* | 4/2008 | Imgrund et al. ................ 433/24 |
| 7,613,527 B2 | 11/2009 | Raby |
| 7,695,278 B2* | 4/2010 | Sporbert et al. ................ 433/24 |
| 7,766,653 B2* | 8/2010 | Manemann et al. ............ 433/24 |
| 7,844,429 B2* | 11/2010 | Matov et al. ..................... 703/7 |
| 7,865,259 B2* | 1/2011 | Kuo et al. ....................... 700/98 |
| 7,880,751 B2* | 2/2011 | Kuo et al. ..................... 345/634 |
| 8,029,277 B2* | 10/2011 | Imgrund et al. ................ 433/24 |
| 8,512,037 B2* | 8/2013 | Andreiko ........................ 433/24 |
| 8,727,776 B2* | 5/2014 | Mehl ............................ 433/223 |
| 2002/0102009 A1 | 8/2002 | Jones |
| 2004/0023188 A1 | 2/2004 | Pavlovskaia et al. |
| 2004/0110110 A1 | 6/2004 | Chishti |
| 2005/0055118 A1 | 3/2005 | Nikolskiy |
| 2005/0130095 A1 | 6/2005 | Raby et al. |
| 2005/0271996 A1 | 12/2005 | Sporbert |
| 2006/0063135 A1 | 3/2006 | Mehl |
| 2006/0073436 A1 | 4/2006 | Raby |
| 2006/0147872 A1* | 7/2006 | Andreiko ........................ 433/24 |
| 2006/0263739 A1* | 11/2006 | Sporbert et al. ................ 433/24 |
| 2006/0263741 A1* | 11/2006 | Imgrund et al. ................ 433/24 |
| 2007/0031791 A1 | 2/2007 | Cinader, Jr. |
| 2007/0099146 A1 | 5/2007 | Reising |
| 2008/0057466 A1 | 3/2008 | Jordan |
| 2009/0026643 A1 | 1/2009 | Wiest |
| 2009/0286196 A1 | 11/2009 | Wen |
| 2010/0138025 A1* | 6/2010 | Morton et al. ................ 700/104 |
| 2010/0153075 A1* | 6/2010 | Sporbert et al. ................. 703/1 |
| 2010/0179789 A1 | 7/2010 | Sachdeva |
| 2010/0260405 A1 | 10/2010 | Cinader, Jr. |
| 2010/0324715 A1 | 12/2010 | Yang |

FOREIGN PATENT DOCUMENTS

| | | |
|---|---|---|
| CN | 100586611 | 2/2010 |
| CN | 101647729 | 2/2010 |
| JP | 2006-175205 | 7/2006 |
| WO | WO 2007/084727 | 7/2007 |

OTHER PUBLICATIONS

LingualJet European Show Info_Brochure (PDF copy in WorkSite) undated, 15 pages.
International Search Report PCT/US12/25605 Aug. 24, 2012, 5 pages.

* cited by examiner

ORTHODONTIC DIGITAL SETUPS

1. FIELD OF THE INVENTION

Provided are methods related to digitally enabled orthodontics and, more particularly, computer-based methods for assisting orthodontic diagnosis and treatment.

2. DESCRIPTION OF THE RELATED ART

The field of orthodontics is concerned with repositioning a patient's teeth for improved function and aesthetic appearance. For example, orthodontic treatment often involves the use of tiny slotted appliances, known as brackets, which are generally fixed to the patient's anterior, cuspid, and bicuspid teeth. An archwire is received in the slot of each bracket and serves as a track to guide movement of the teeth to desired orientations. The ends of the archwire are usually received in appliances known as buccal tubes that are secured to the patient's molar teeth. The archwire and appliances are commonly referred to as "braces." Orthodontic treatment may also be implemented through the use of clear plastic tooth positioning trays or other functional appliances.

The practice of orthodontics has traditionally relied on manual steps, such as the selection of proper appliances for the particular patient, placement of appliances in the mouth, and adjustment of appliances throughout treatment. More recently, advancement in technology has allowed some of these steps to be assisted through the use of computers. For example, computers can be used to guide the acquisition of data representing the teeth arrangement of an individual patient. Such data can then be used to visualize the patient's dentition to diagnose and assist in orthodontic treatment planning at any stage of treatment. Furthermore, these data can be used in manufacturing appliances, such as brackets, that are customized to the patient.

There are numerous advantages to using customized appliances. First, the prescription of the appliances can account for the variability in the starting positions of the maloccluded teeth and provide more efficient delivery of forces to teeth. Second, the customization of an orthodontic archwire or bracket bases can allow for significantly lower profile brackets to be used, since the archwire can contour more closely with the surfaces of the teeth. This in turn can lead to enhanced patient comfort, especially with respect to lingual appliances. Third, the shape of bonding surfaces can be manufactured to precisely complement the teeth surfaces to assist in bonding the appliances and maximize the bond reliability.

When raw data representing the shapes of teeth are received by a computer, the data is often little more than a point cloud in three dimensional (3D) space. Typically, this point cloud is surfaced to create 3D object models of the patient's dentition, including one or more teeth, gingival tissue, and other surrounding oral structure. In order for this data to be useful in orthodontic diagnosis and treatment, the dentition surface is generally "segmented" to produce one or more discrete, movable 3D tooth object models representing individual teeth. It is also preferred that these tooth models are separated from the gingiva into separate objects.

Segmentation allows a user to characterize and manipulate the teeth arrangement as a set of individual objects. Advantageously, diagnostic information such as arch length, bite setting, and even ABO grading could be derived from these models. As a further benefit, digital orthodontic setups can provide flexibility in the manufacturing process. By replacing physical processes with digital processes, the data acquisition step and data manipulation steps can be executed at separate locations without the need to transport stone models or impressions from one location to another. Reducing or eliminating the need for shipping physical objects back and forth can result in significant cost savings to both customers and manufacturers of customized appliances.

3. SUMMARY OF THE INVENTION

Some of the technically challenging aspects of digitally enabled orthodontics relate to the proper recognition of tooth objects in the segmentation process. Teeth tend to display significant variability in size and shape, making it difficult for computers to recognize boundaries that separate a given tooth from adjacent teeth and other surrounding structure, such as gingival tissue. Especially problematic are the chewing surfaces of teeth, which can be jagged, worn and unpredictable. These can frustrate efforts by a computer to automatically separate tooth surfaces from surrounding structure. While a human can easily isolate surfaces belonging to a single tooth, it can be time-consuming for a human to manually perform the segmentation process on an entire arch.

This problem can be alleviated by using a two-step method in which a virtual surface is used to identify at least a portion of a singular tooth surface on a mouth surface. With the virtual surface defined, remaining portions of the mouth surface are then automatically analyzed to identify the boundaries that separate the tooth surface from surrounding mouth surfaces, thus defining segmented tooth objects. By excluding portions of the mouth surface already known to be part of a single tooth, this method leverages the knowledge of the user while retaining the advantages of a semi-automatic process. The success rate of computerized segmentation substantially increases by excluding crown surfaces that tend to induce error. Additionally, the computation is significantly accelerated by reducing the area of mouth surface analyzed after each successive tooth has been identified.

In one aspect, a computer-implemented method for recognizing the gingival margin of a tooth is provided. The method comprises: receiving into the computer surface model data that digitally defines a three-dimensional surface of at least a portion of a mouth, the portion containing at least one tooth; presenting a rendering of the surface model data in a user interface; receiving input data specifying a point on the rendered surface model associated with a tooth; using the computer's processor, deriving a perimeter on the surface model of the tooth based on the input data; and using the computer's processor, analyzing the surface model along a plurality of paths outwardly extending from points on the perimeter along the three-dimensional surface to produce gingival margin data, which is data that defines a boundary in the surface model separating the tooth surface and surrounding surfaces of the mouth.

In another aspect, a computer-implemented method of defining a tooth coordinate system for a virtual tooth is provided, comprising: presenting the virtual tooth in a user interface of a digital display; receiving point input data that defines a point on the virtual tooth; receiving axis input data that defines first and second axes associated with the virtual tooth; using the computer's processor, computing a substantially normal vector for a portion of the tooth surface surrounding the point; and computing the tooth coordinate system based on the axis input and the computed vector.

In still another aspect, a computer-implemented method of simulating a collision between a first virtual tooth and a second virtual tooth is provided, comprising: receiving into the computer digital data defining, in three-dimensional space, the first virtual tooth and the second virtual tooth; receiving permissible movement input data directed to permissible movement of the first virtual tooth along or about a first axis; using the computer's processor, simulating, in three dimensional space, bringing the first virtual tooth into contact with the second virtual tooth while constraining movement of the first virtual tooth based on the permissible movement input data; and displaying, in a user interface of a display, data resulting from the simulation.

In yet another aspect, a computer-implemented method of simulating a collision between a first virtual arch and a second virtual arch is provided, comprising: receiving into the computer digital data defining, in three-dimensional space, the first virtual arch and the second virtual arch; receiving permissible movement input data directed to permissible movement of the first virtual arch along or about a first axis; using the computer's processor, simulating, in three dimensional space, bringing the first virtual arch into contact with the second virtual arch while constraining movement of the first virtual arch based on the permissible movement input data; and displaying, in a user interface of a display, data resulting from the simulation.

4. BRIEF DESCRIPTION OF THE DRAWINGS

DEFINITIONS

As used herein:

"Mesial" means in a direction toward the middle of the patient's curved dental arch.

"Distal" means in a direction away from the middle of the patient's curved dental arch. "Occlusal" means in a direction toward the outer tips of the patient's teeth.

"Gingival" means in a direction toward the patient's gums or gingiva.

"Buccolabial" means in a direction toward the patient's lips or cheeks.

"Lingual" means in a direction toward the patient's tongue.

5. DETAILED DESCRIPTION OF THE PREFERRED EMBODIMENTS

Figure 1A:
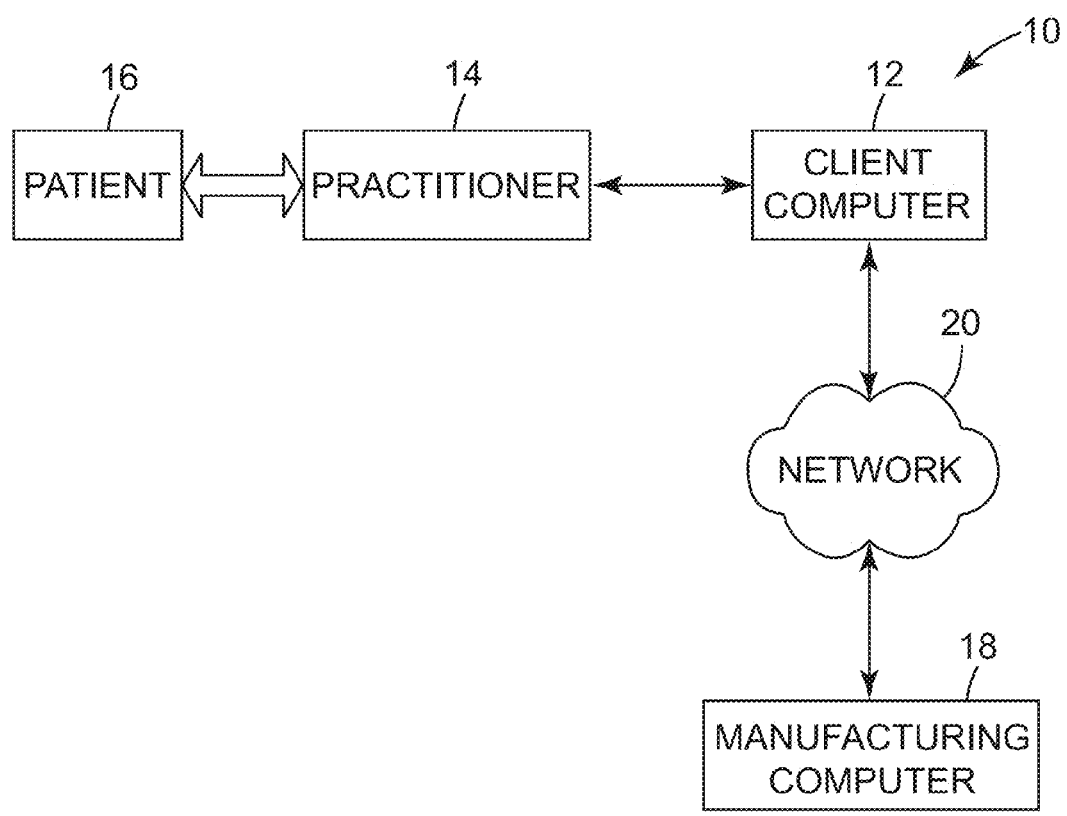
FIG. 1A is a block diagram of an exemplary computer environment in which a client computer communicates with a manufacturing facility.

FIG. 1A is a block diagram illustrating an exemplary computer environment 10 that includes a client computer 12. Preferably, the client computer 12 has a processor, input device, memory, and display device. The client computer 12 presents an environment for an orthodontic practitioner 14 to interact with a digital representation of a portion of or an entire dental arch of patient 16 to generate and visualize an orthodontic digital setup for patient 16. Optionally and as shown, the client computer 12 communicates with a manufacturing facility 18 via network 20.

The client computer is operated by a user. The user interacts with modeling software executing on a computer to visualize, process, and manipulate the 3D representation of a patient's dental arch, arches, or subsets thereof. The computer may be located in the manufacturing facility 18, a dental laboratory, or practitioner's office. As another possibility, the computing resources for running the software may be spread over two or more computers in different locations. Optionally, the interaction between the user and the modeling software is conducted in view of creating one or more appliances, such as a customized brace or aligning tray, at the manufacturing facility 18.

Figure 1B:
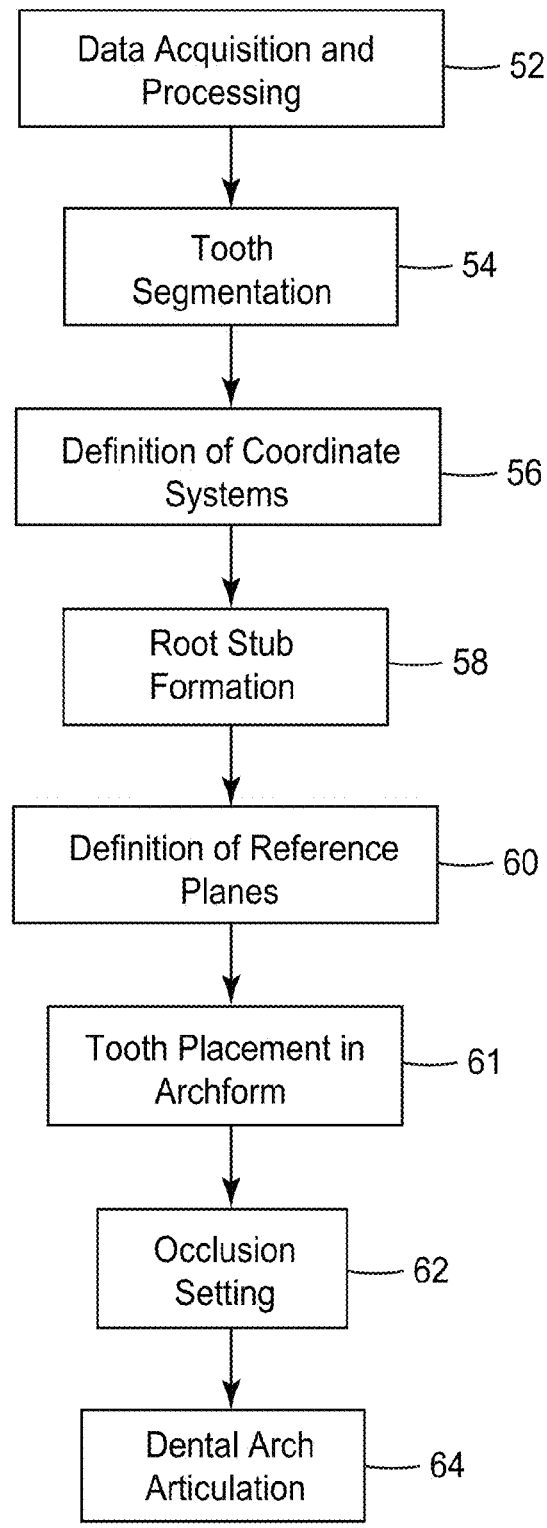
FIG. 1B is a high-level flowchart directed to an exemplary orthodontic digital setup.

FIG. 1B provides an exemplary workflow for a digital orthodontic setup. In this exemplary embodiment, the orthodontic digital setup provides methods for recognizing tooth surfaces, separating tooth surfaces from surrounding dental structure, supplementing the shapes of tooth surfaces, and moving the tooth surfaces toward desired positions (locations and orientations). These methods can be advantageously used to diagnose a malocclusion for achieving mid-treatment or final treatment goals. Digital representations of a patient's dentition can also provide mid-course treatment corrections or specify one or more orthodontic appliances, as described in U.S. Publication No. 2010/0260405 (Cinader).

As shown in the figure, the workflow can be sub-divided into basic steps, including Data Acquisition and Processing (Block 52), Tooth Segmentation (Block 54), Definition of Coordinate Systems (Block 56), Root Stub Formation (Block 58), Definition of Reference Planes (Block 60), Tooth Placement in Archform (Block 61), Occlusion Setting (Block 62), and Dental Arch Articulation (Block 64). In the following sections, each of these steps shall be examined in turn, bearing in mind that the invention may represent fewer than all of these steps, more than all of these steps, and/or steps carried out in a different order than the order shown in FIG. 1B.

Data Acquisition and Processing

Digital orthodontic setups begin with obtaining data representing the patient's dentition and digitally processing this data, as shown by Block 52 in FIG. 1B. A digital dentition surface (or surface model), of a patient's dental arrangement is provided and stored on a local or remote computer. The dentition surface (or mouth surface) represents a shape of at least part of a patient's mouth. The dentition surface may represent both arches of a patient, only the upper or lower arch, or only a portion of one or both arches. Optionally, a dentition surface representing only a portion of a patient's dental structure may be desired, for example, in cases in which treatment is sought for some but not all of the teeth. As used herein, "dentition surface" and "mouth surface" are interchangeable.

In some embodiments, the first dentition surface may be provided using a hand-held intra-oral scanner such as the intra-oral scanner using active wavefront sampling described by Brontes Technologies, Inc. (Lexington, Mass.) in PCT Publication No. WO 2007/084727 (Boerjes, et al.). Alternatively, other intra-oral scanners or intra-oral contact probes may be used.

The dentition surface may be provided by scanning either a positive or negative impression of the patient's teeth. As another option, the dentition surface may be provided by using a contact probe on a model of the patient's teeth. The model used for scanning may be made, for example, by casting an impression of a patient's dentition from a suitable impression material such as alginate or polyvinylsiloxane, and scanning the impression. If a stone model has been cast from the impression, the stone model can be scanned instead. Any suitable scanning technique may be used for scanning the impression or model, including X-ray radiography, laser scanning, computed tomography, magnetic resonance imaging, and ultrasound imaging. Other possible scanning methods are described in U.S. Patent Publication No. 2007/0031791 (Cinader et al.).

Additional processing steps can be implemented in creating the 3D dentition surface. For example, the raw data may be optionally "cleansed" by removing any data points that represent errors or are unnecessary. For example, data files representing a tooth surface that include one or more data points significantly outside the normal expected geometrical relationship of adjacent data points (i.e. outliers) could be fixed by data handling software or human intervention to remove the erroneous data point(s). In addition, tooth data points that are missing could be added or estimated by data handling software to create realistic, smoothly curved shapes of teeth or the jawbone, as defined by the data points.

In preferred embodiments, the digital data is then "surfaced", or converted from digital point clouds to 3D surfaces by modeling software from a provider such as Geomagic, Inc. (Research Triangle Park, N.C.).

Figure 2A:
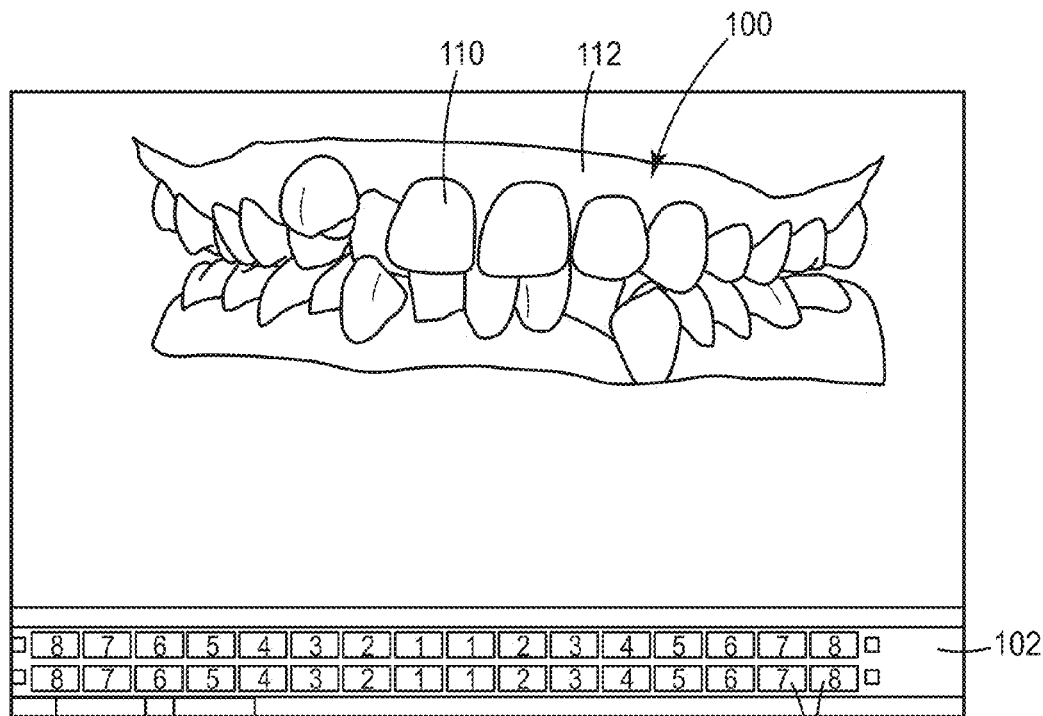
FIG. 2A shows a dentition surface of the upper and lower arches of a patient according to one embodiment.

FIG. 2A shows an exemplary 3D model surface of an exemplary patient's maloccluded dentition, represented here by the numeral 100. The dentition surface 100 is rendered on a 3D user interface as a 3D mesh of surface triangles representing both the upper and lower arches. Notably here, the dentition surface 110 includes not only maloccluded teeth 110 but also surrounding gingival tissue 112.

Tooth Segmentation

Following the acquisition of data to create the dentition surface, the dentition surface is then virtually separated into discrete elements so that, for example, each tooth may be independently moved as a separate object. This is represented by Block 54 in FIG. 1B.

Referring to FIG. 2A, an exemplary toolbar 102 is provided to provide additional information about the teeth types represented by the dentition surface 100. The toolbar 102 includes a set of elements 104 labeled in Palmer notation denoting the complete set of 32 teeth in an adult dental arch. Different types of notation may be used such as universal or Federation Dentaire Internationale (FDI) World Dental Federation notation.

Figure 2B:
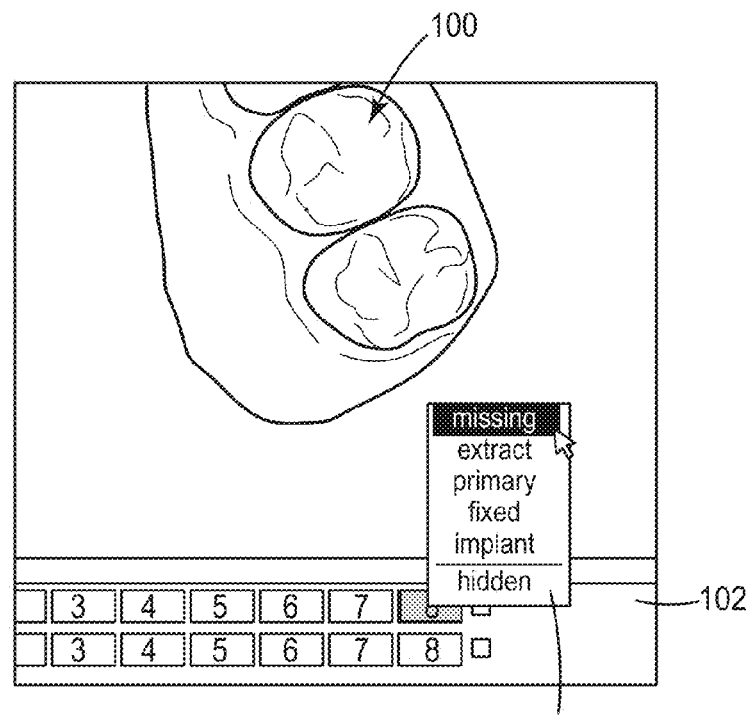
FIG. 2B is a fragmentary view showing the classification of teeth in the dentition surface of FIG. 2A by a user.

FIG. 2B shows a simplified method of entering user input directed to one or more tooth types with respect to the dentition surface 100. By clicking on each element 104 on the toolbar 102, a dialog box 106 appears. The dialog box 106 allows the user to enter information specific to that tooth. For example, in FIG. 2B, the dialog box 106 is being used to indicate that the upper left third molar tooth is missing in the dentition surface 100. Further information, for example, concerning missing teeth, implants, teeth for extraction, fixed teeth, and primary teeth can be conveniently entered using the toolbar 102. Further aspects of this user interface can be found in issued U.S. Pat. No. 7,613,527 (Raby, et al.).

Figure 3:
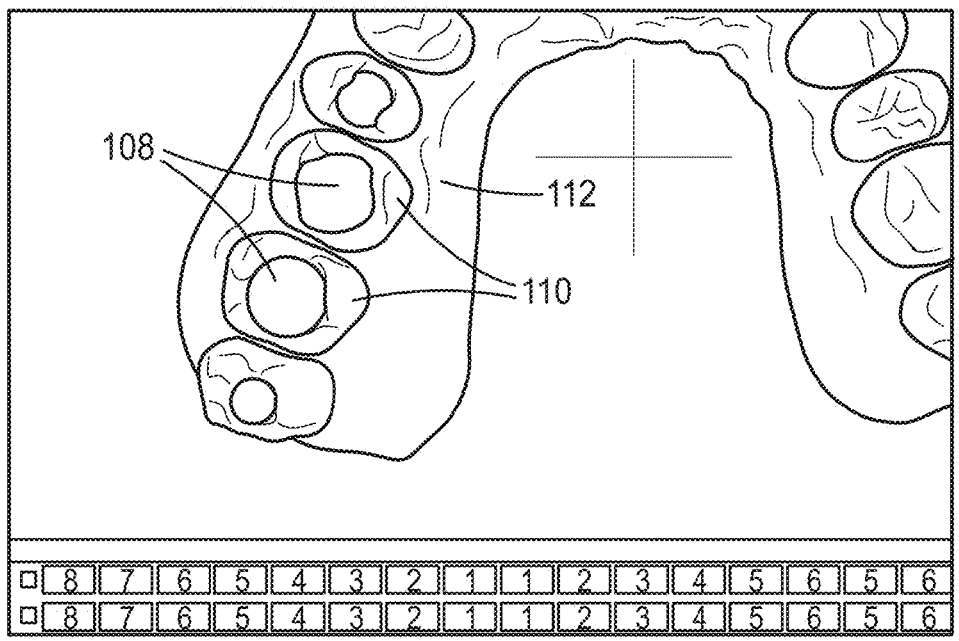
FIG. 3 shows the arrangement of markers on individual teeth in the dentition surface of FIGS. 2A and 2B.

FIG. 3 shows a process by which a user assists the computer in recognizing individual teeth by providing input data specifying one or more points on the dentition surface 100. In this example, the points are specified on each tooth 110 of the dentition surface 100 using a cursor control device. A suitable cursor control device can be a mouse, trackball, pen, or touch screen. Upon selection of each point location, the corresponding tooth is marked with a virtual auxiliary surface—here a sphere 108—that is placed on the tooth 110 around the point location. Each sphere 108 encloses, and is concentric about, the user-selected location and is shown concurrently with the dentition surface 100—here, intersecting with each tooth 110 in 3D space. Moreover, each sphere 108 is indexed to an element 104 on the toolbar 102, such that each sphere is registered to exactly one particular tooth in the dental arch.

As shown in the example of FIG. 3, the sphere 108 and the dentition surface 100 intersect with each other to form a virtual intersection line on the sphere 108 and the dentition surface 100. Each point location is specified such that all portions of the dentition surface 100 that intersect with the corresponding sphere 108 are part of a single tooth 110. In other words, the sphere 108 does not intersect with any of the surrounding gingival tissue 112 or other neighboring teeth 110 (note that this does not preclude the sphere 108 from extending above the occlusal surfaces of the tooth 110 as shown in FIG. 3).

As a result of this constraint, portions of the dentition surface 100 enclosed by the virtual intersection line are designated as a partial tooth surface of the individual tooth 110. Defining each tooth 110 in this manner is highly beneficial in avoiding errors in teeth segmentation because furrowed and ridged portions of the molar teeth 110 can be partially or fully contained within the sphere 110. As a result, these areas of the teeth 110 can be removed from consideration in subsequent computational analyses, thus reducing the risk of identifying erroneous tooth boundaries.

Optionally, the spheres 108 are shaded (as shown) or color-coded to allow a user to easily identify specific teeth that have been marked. As an example, green spheres 108 may be used to represent first bicuspid teeth, and orange spheres may be used to represent cuspid teeth. Advantageously, such a coding scheme helps eliminate user error in placing spheres 108 on the teeth 110, particularly when one or more teeth are missing.

In some embodiments, the size of the sphere is predetermined according to the tooth associated with the selected location. Preferably, the sizes of the spheres 108 generally scale with the sizes of the associated teeth according to statistical norms in the patient population. In FIG. 3, for example, the first and second molar teeth are associated with relatively large spheres 108', and anterior teeth are associated with relatively small spheres 108".

While each tooth 110 is being marked with a sphere 108 in this embodiment, other auxiliary surfaces are also contemplated for this purpose. For example, the auxiliary surface could be an alternative geometric form such as an ellipsoid, torus, or cube. The auxiliary surface could be either an open-manifold or closed-manifold surface. If desired, an open surface (having one or more boundaries) such as an open-ended cylinder, disk, or rectangular surface may be used. However, the use of spheres 108 is particularly preferred because spheres are not orientation-dependent and can be faster to analyze computationally.

Although use of an auxiliary surface to define the perimeter is helpful, it is not required. For example, a perimeter can be defined directly on the virtual tooth surface by free-hand user input.

Figure 4:
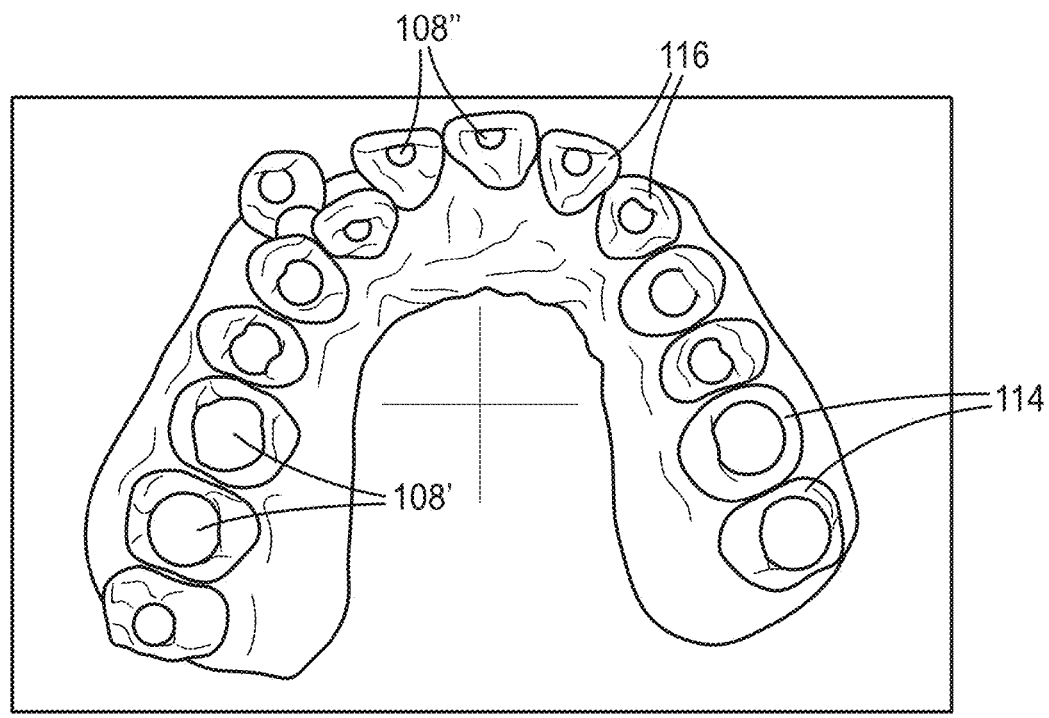
FIG. 4 shows the dentition surface of FIGS. 2A-3 with all markers placed.

FIG. 4 shows teeth 110 of the upper dental arch of the dentition surface 100 that has been completely marked by the placement of spheres 108 as described above. Optionally and as shown, the spheres 108 placed on the molar teeth 114 intersect with the occlusal surfaces of the molar teeth 114, while the spheres 108 placed on the anterior teeth 116 intersect with the lingual surfaces of the anterior teeth 116. The intersection of each sphere 108 and respective tooth 114, 116 with each other defines a closed perimeter on the surface of the respective tooth 114, 116. The perimeter, defined in 3D space, can be generally circular in shape, but this need not be the case where tooth surfaces are highly irregular.

Figure 5A:
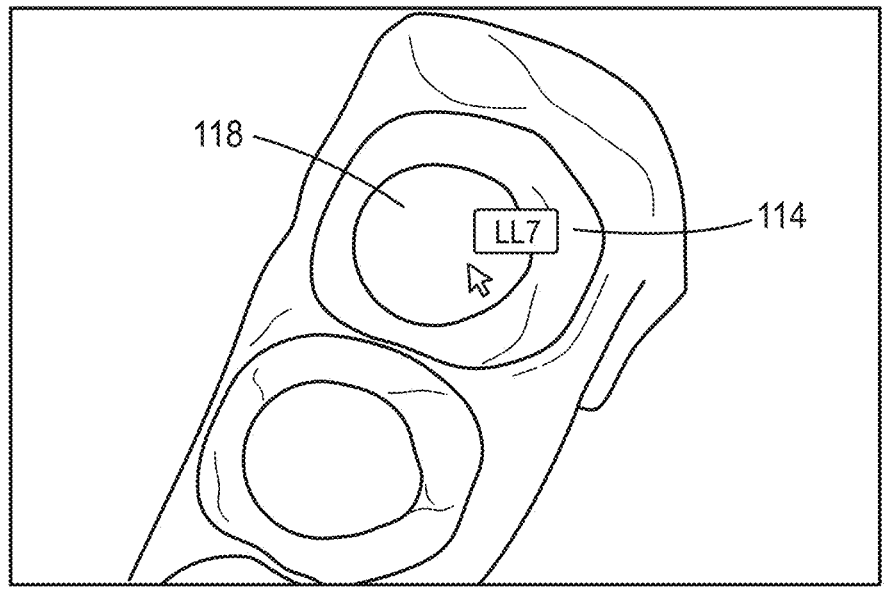
FIGS. 5A and 5B show the re-sizing of a marker on an individual tooth in the dentition surface of FIGS. 2A-4.
Figure 5B:
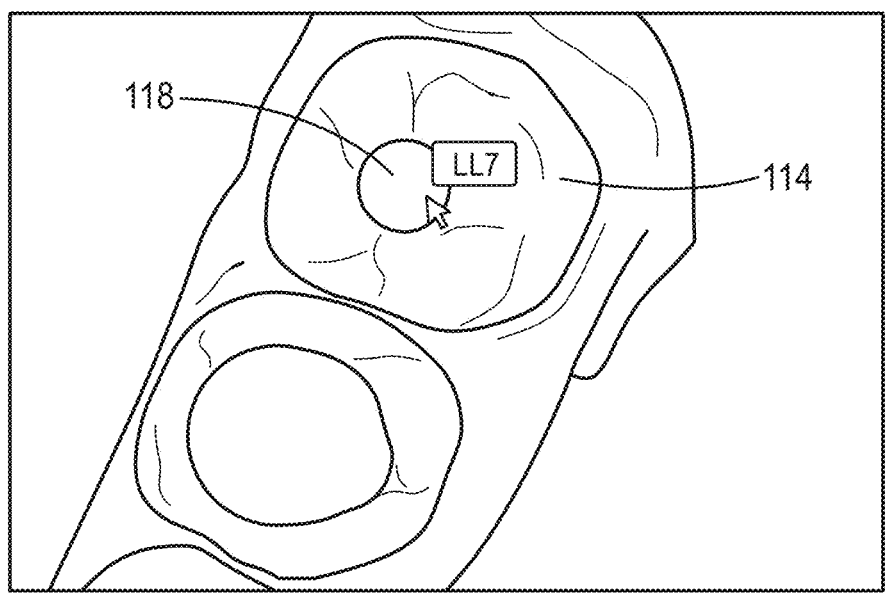
Figure 6:
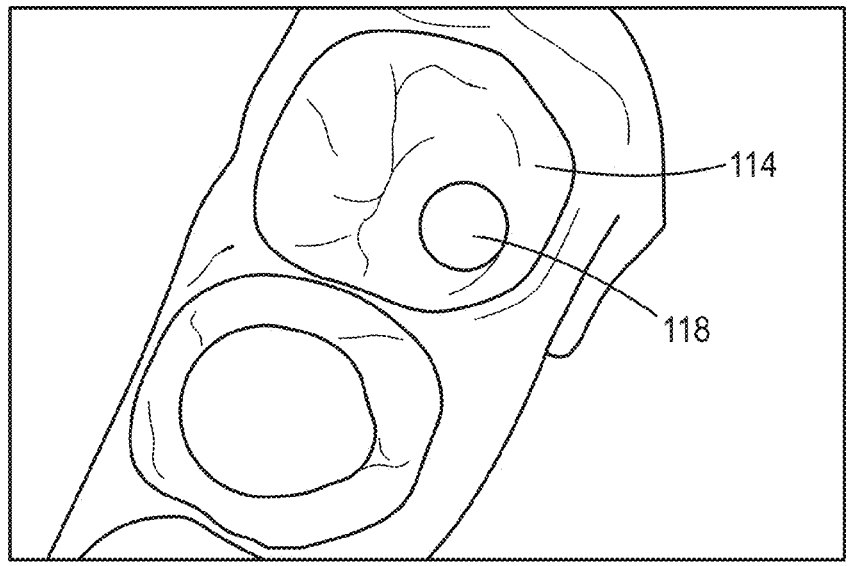
FIG. 6 shows the translation of a marker from its original position in the dentition surface of FIGS. 2A-5B.

After all of the spheres 108 have been placed on both the upper and lower arches, further adjustments can be made to one or more of the spheres 108. For example, as shown in FIGS. 5A and 5B, the size of a sphere 118 on a lower molar tooth 114 is manually adjusted from a larger to a smaller size by a user. In an exemplary two-step process, a cursor control device is used to select the sphere 118 in FIG. 5A, and a subsequent keyboard or cursor control device action (such as rolling the scroll-wheel of a mouse) is used to shrink the sphere 118 in FIG. 5B. FIG. 6 shows an adjustment to the position of the sphere 118 relative to the tooth 114. As shown, the sphere 118 is translated as desired by clicking and dragging the sphere 118 to a new location. Adjustments to the size and location of one or more spheres 108 can help keep the spheres 108 separated from known defects in the dentition surface 110, and provide for a more robust tooth segmentation process.

Figure 7:
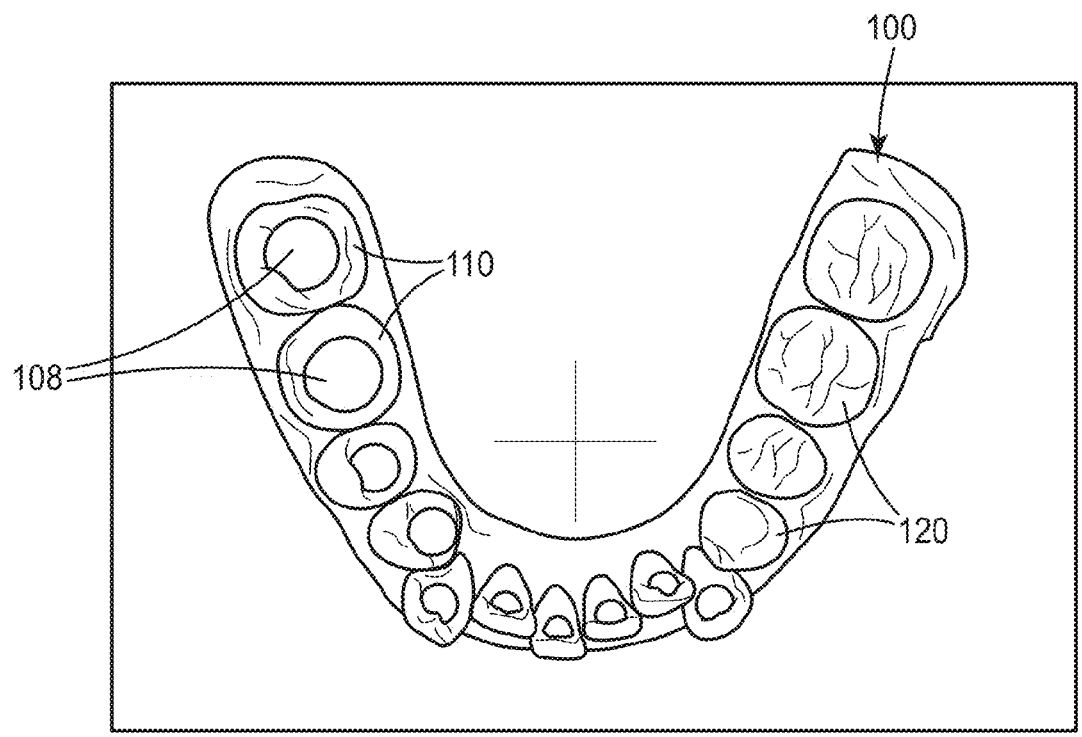
FIG. 7 shows partially completed output from the automated process of separating the individual teeth from surrounding structure in the dentition surface of FIGS. 2A-6.

FIG. 7 shows an automated aspect of the segmentation process. Once all of the spheres 108 have been placed and adjusted, the user instructs the computer to execute a tooth segmentation procedure. In the embodiment depicted, a computer algorithm is executed for each tooth 110 of the lower arch of the dentition surface 100, beginning with the lower left second molar and ending with the lower right second molar. Other tooth orderings are possible and may be appropriate, depending on the tooth numbering notation used in the toolbar or depending on regional practices or individual user preferences.

In a preferred embodiment, any surface triangle of the dentition surface 100 located within the corresponding sphere 108 is designated as a partial tooth surface, or part of an individual tooth surface 120. Once the tooth surface 120 has been initially defined, the dentition surface 100 is then analyzed along a plurality of paths outwardly extending from the sphere 108 along the dentition surface 110 to automatically recognize a boundary separating the tooth surface 120 and the surrounding structure. Once each tooth surface 120 is fully defined, the corresponding sphere 108 is removed and the tooth surfaces 120 are suffused with color or shaded as shown in FIG. 7.

Figure 8:
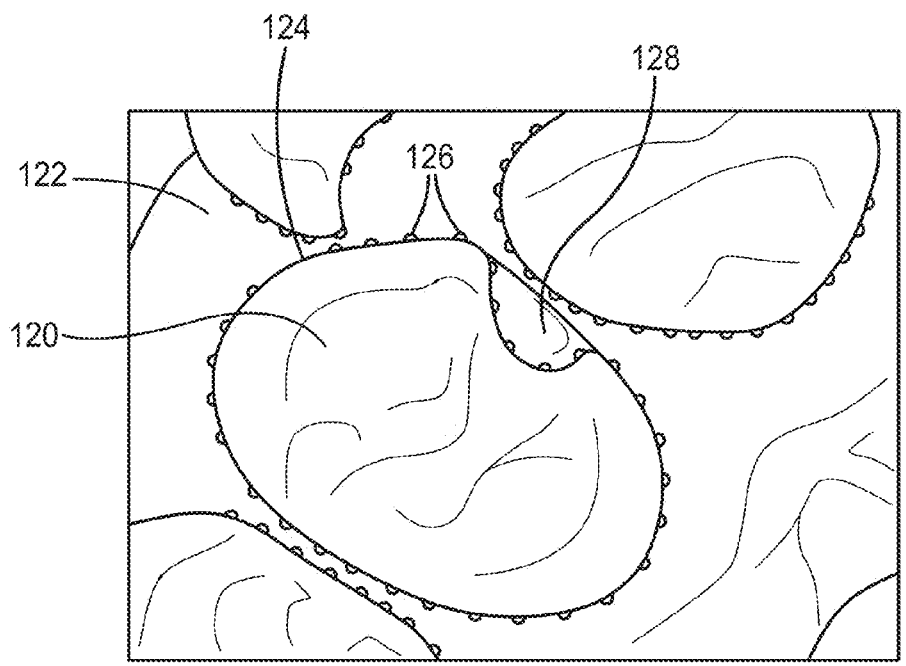
FIG. 8 shows the inspection of the separated tooth surfaces and gingival margins in the dentition surface of FIGS. 2A-7.

FIG. 8 shows in more detail an exemplary gingival boundary 124 partitioning the tooth surface 120 and the surrounding structure 122. In a particular embodiment, the boundary 124 is determined by probing the degree of concavity along the surface of the dentition surface 110. With the surface triangles already identified as part of the tooth surface 120 as a starting point, the computer algorithm proceeds by outwardly searching for surface triangles of the dentition surface 110 having a certain numeric characteristic. This numeric characteristic can determine, or assist in determining, the local concavity of the dentition surface 100.

The algorithm proceeds to search for surface triangles that are potential boundary triangles. Potential boundary triangles satisfy a threshold local concavity, a condition that suggests that a boundary between the tooth and a surrounding structure may have been found. This threshold can be met, for example, when the numeric characteristic falls above a threshold value, below a threshold value, or within a pre-determined range of values. In a preferred embodiment, the numeric characteristic is an angle formed between the plane of the given surface triangle and the plane of one of three possible neighboring surface triangles. Alternatively, the numeric characteristic could be the internal angle, aspect ratio or overall area of the surface triangle.

The above searching process is applied iteratively to identify an end-to-end chain of contiguous boundary triangles in which each boundary triangle satisfies the threshold concavity requirement. The identified series of triangles can thus define a proposed gingival boundary. The proposed gingival boundary is deemed acceptable, for example, if each boundary triangle has a numeric characteristic that satisfies a threshold value and also has a maximum of two neighbors that likewise satisfy this condition. In a preferred embodiment, the numeric characteristic is an angle of a surface triangle whose threshold value starts at 5 degrees. This condition may be used to propose a set of surface triangles for providing an acceptable gingival boundary (i.e. gingival margin). If this condition is found unacceptable, the threshold value can be iteratively changed by 0.5 degree decrements and this process repeated until an acceptable gingival boundary is provided.

Additional constraints may be hard-coded into the software to improve the performance or robustness of the algorithm. For example, a maximum dimension of the tooth surface 120 may be specified. In some embodiments, the size of the tooth surface 120 is specified as being no greater than 12 millimeters, no greater than 14 millimeters, no greater than 15 millimeters, no greater than 16 millimeters, or no greater than 18 millimeters. Optionally, limitations may be placed based on a minimum dimension for the tooth surface 120.

In FIG. 8, the boundary 124 is rendered smooth by using a spline function (such as a cubic spline function) that connects the identified set of surface triangles. Having thus defined the boundary 124, the portion of the dentition surface between the tooth boundary and the intersection line is designated as a second partial tooth surface. Finally, the completed tooth surface 120 is formed by combining the first and second partial tooth surfaces.

Optionally and as shown, the boundary 124 is outfitted with a plurality of adjustable nodes 126 that are located along the boundary 124. The nodes 126 act as control points, allowing a user to correct errors in the boundary 124 as described below.

Figure 9A:
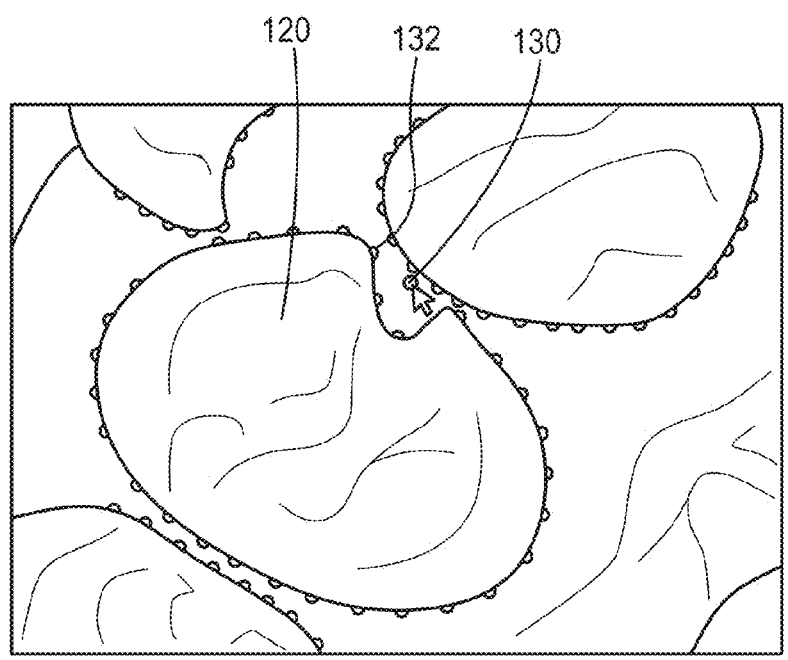
FIGS. 9A and 9B show the process of repairing a defect in the gingival margins in the dentition surface of FIGS. 2A-8.
Figure 9B:
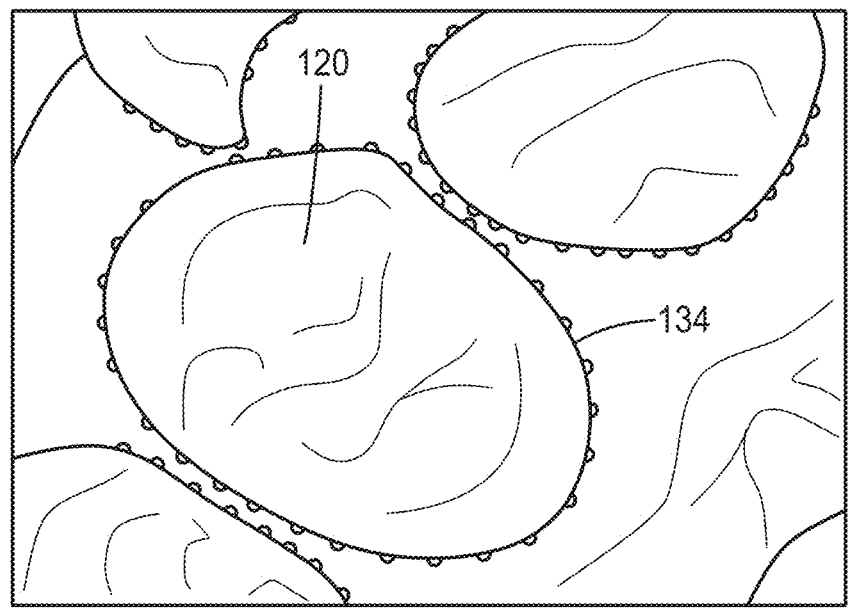
Figure 10:
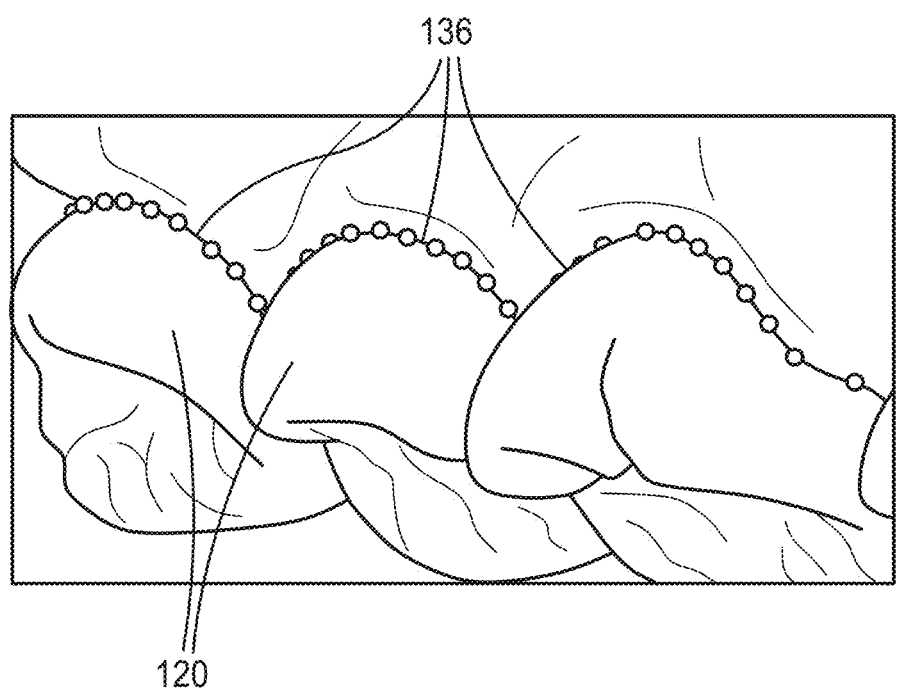
FIG. 10 shows one view of the finished result of the tooth separation, inspection and repair processes in the dentition surface of FIGS. 2A-9B.

FIGS. 9 and 10 show a convenient process for correcting, or "healing", a user-identified defect in the boundary 124. As shown, a user uses the pointer to click and drag a first node 130 toward a second node 132 to indicate a gap that should be closed along the boundary 124. When the first node 130 is positioned over the second node 132 and released, the software automatically eliminates erroneously defined sections of the boundary 124 between the nodes 130,132, resulting in a properly corrected gingival boundary 134.

Figure 11A:
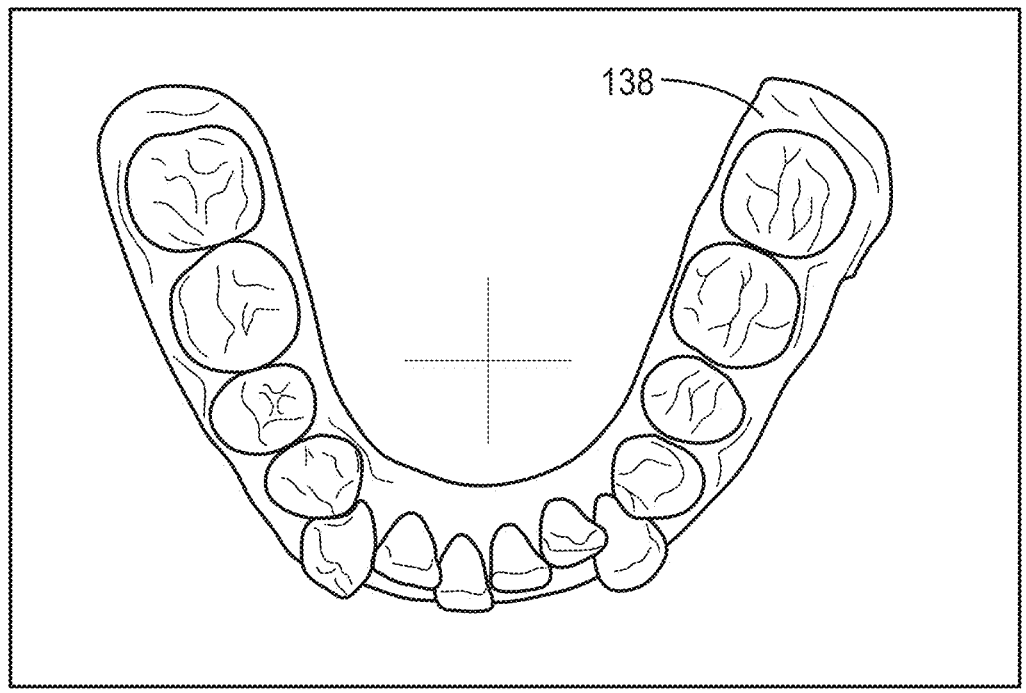
FIGS. 11A and 11B are occlusal and buccolabial views of the final tooth surfaces in the dentition surface of FIGS. 2A-10 with the gingiva distinguished.
Figure 11B:
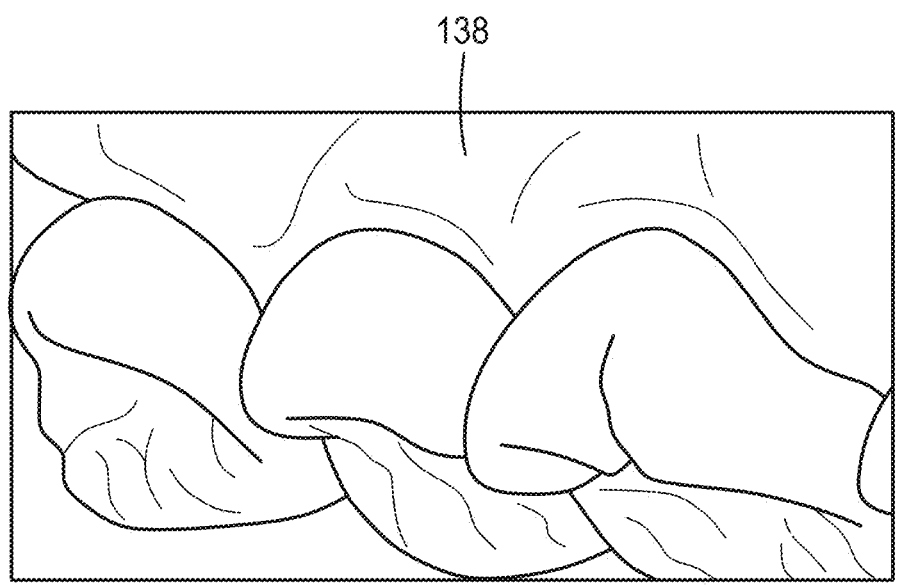
Figure 12:
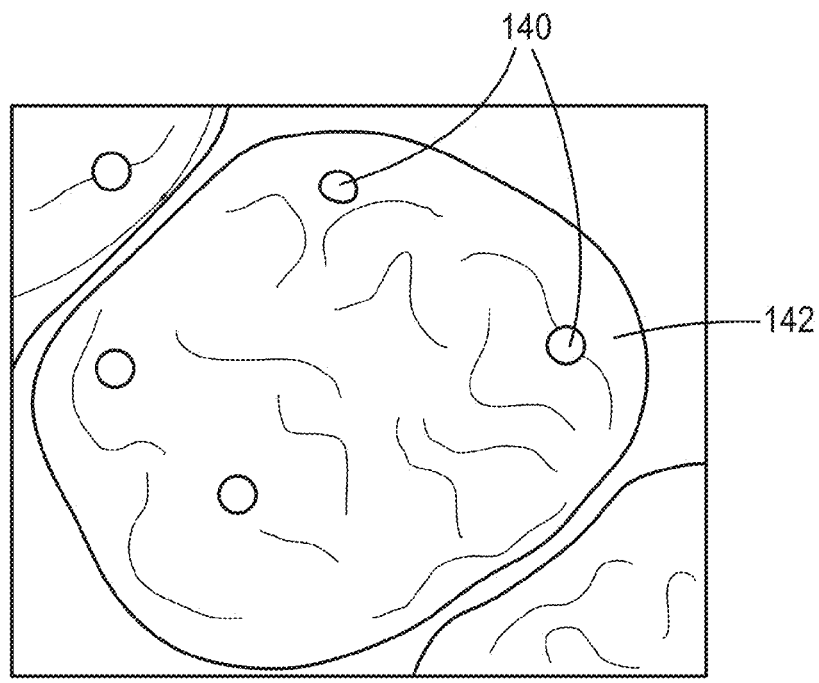
FIGS. 12 and 13 are occlusal and perspective views showing identification of landmarks by a user on a tooth surface in the dentition surface of FIGS. 2A-11.

FIG. 10 presents, in the user interface, visual indicia on the rendering of the surface model showing the gingival boundaries 136 separating the tooth surfaces 120 from the surrounding surfaces of the mouth. As shown here, the boundaries 136 separate the tooth surfaces 120 both from the gingiva and from each other. After the gingival boundaries 136 have been deemed satisfactory, the user accepts the tooth surfaces 120 as is. FIGS. 11 and 12 show the segmented dentition surface 138. Optionally and as shown, the boundaries 136, nodes 126, and shading of the teeth are removed for clarity in the completed model 138.

Definition of Coordinate Systems

After the dentition surface 138 has been provided, a coordinate system, defined by coordinate axes, is determined for each of the discrete tooth surfaces. This step is represented by Block 56 in FIG. 1B.

Figure 13:
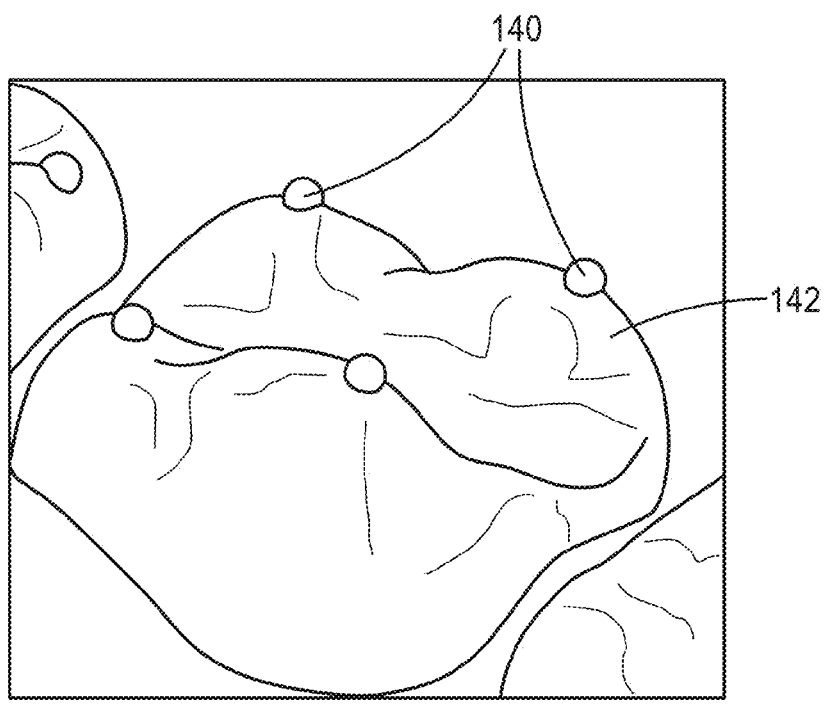

One way of determining these coordinate axes involves the placement of one or more landmarks on the tooth surfaces. For example, FIGS. 12 and 13 show the placement of four landmarks 140 on a molar tooth surface 142, each landmark corresponding to the tip of a respective cusp on the molar tooth. In this example, the location of the landmarks 140 is selected manually by a user. The user may pan, rotate, or zoom the virtual camera relative to the tooth surface 142 in order to better visualize the cusps of the respective tooth. More or fewer than four landmarks may be defined for a given tooth surface. In some embodiments, the software prompts the user to specify the location of each cusp by progressively placing the landmarks 140 along the dentition surface 100.

Initial landmark locations can also be determined automatically or semi-automatically. For example, the computer could propose the location of landmarks 140 based on the overall shape of the tooth surface 142, a long axis of the tooth surface 142, or other feature of the tooth surface 142 as specified by the user. Optionally, a user verifies the placement of landmarks 140 and makes manual adjustments as needed. This process can be repeated for all of the tooth surfaces 142 in the dentition surface 100 that have cusps. These generally include the molar and premolar teeth.

When all of the landmarks 140 have been placed on the tooth surface 142, they are collectively used to define the respective coordinate system for the tooth surface 142. For example, in one embodiment, a molar table (reference plane parallel to the occlusal surface of a molar tooth) is initially computed as a "best fit" to the four landmarks 140. The two buccolabial landmarks 140 are then projected onto the occlusal plane to compute the location and orientation of the mesial-distal axis. The buccolabial-lingual axis lies within the molar table as well and is computed as perpendicular to the x-axis. Finally, the occlusal-gingival axis can be derived from the cross-product of the other two axes.

Figure 14A:
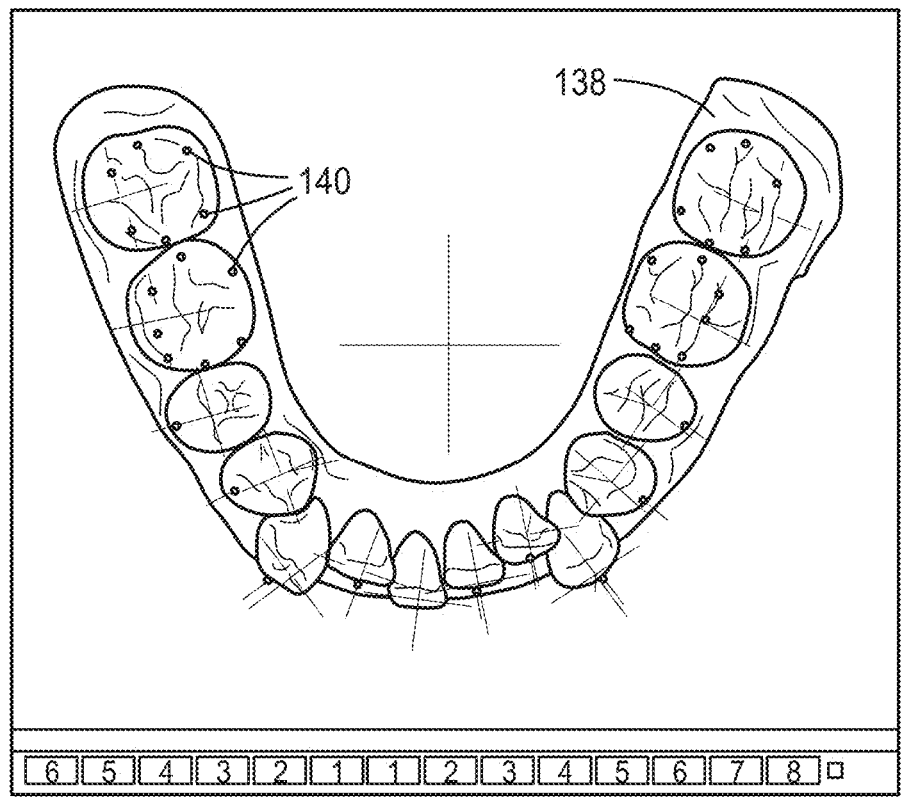
FIG. 14A is an occlusal view of the dentition surface of FIGS. 2A-13 with positioning of landmarks finalized.

Optionally, landmarks may also be defined based on other features of the tooth surface 142. For example, the marginal ridge valley of the tooth surface 142 may also be specified by the user and assist in determining a coordinate system for the respective tooth surface 142. FIG. 14A shows the dentition surface 100 displaying finalized landmarks directed to both the cusps and the marginal ridges of the teeth.

Figure 15:
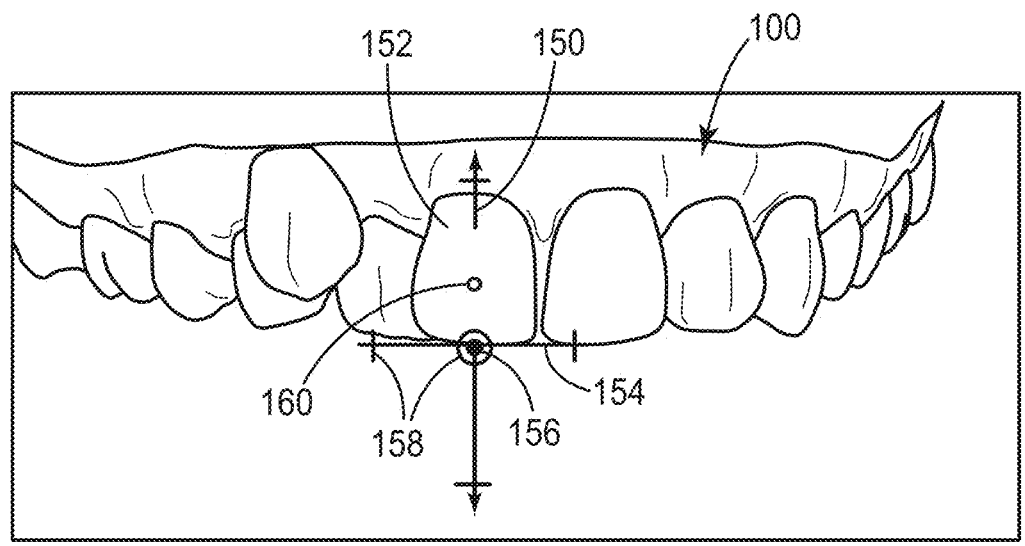
FIG. 15 is a buccolabial view showing a coordinate system on a tooth surface of the dentition surface of FIGS. 2A-14B.
Figure 16:
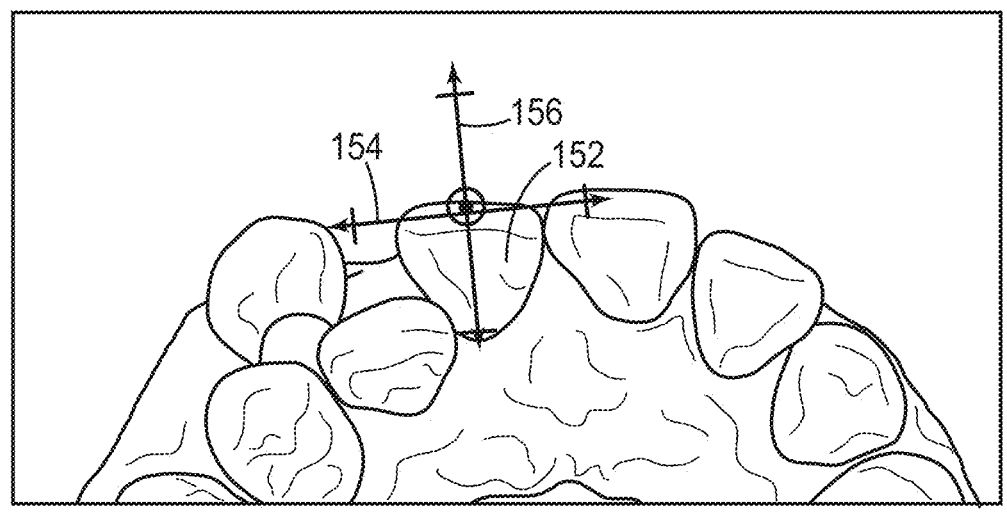
FIG. 16 is an occlusal view showing a coordinate system on a tooth surface of the dentition surface of FIGS. 2A-15.
Figure 17:
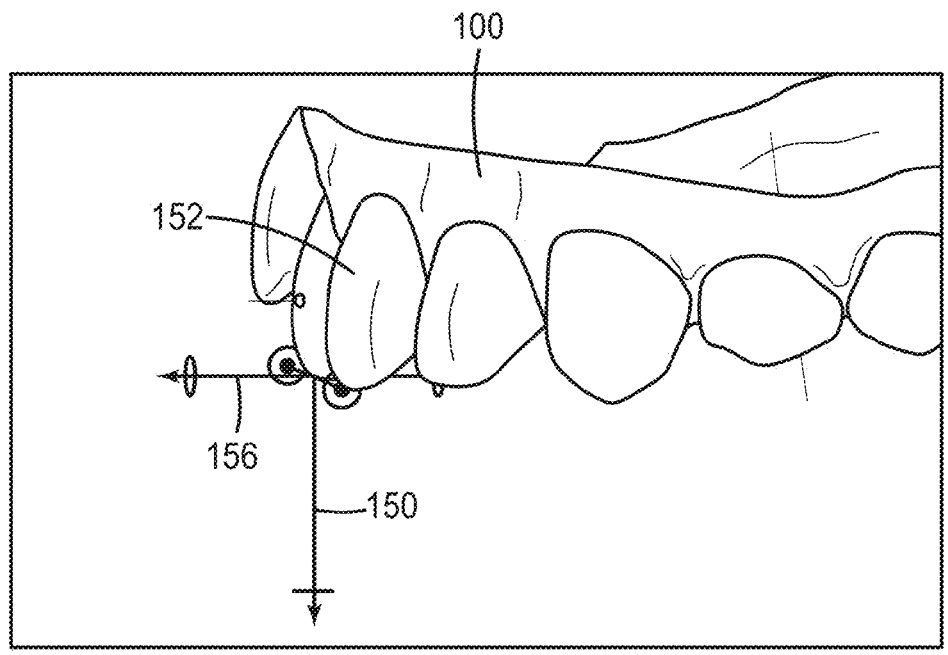
FIG. 17 is a distal view showing a coordinate system on a tooth surface of the dentition surface of FIGS. 2A-16.

FIGS. 15-17 show three different views of a computed coordinate system and adjustment control for a tooth of the dentition surface 100. As illustrated, a first axis 150 (z-axis) is parallel with the perceived long axis of the tooth surface 152, a second axis 154 is aligned with the incisal edge of the tooth, and a third axis 156 intersects axes 150,154 and is substantially normal to the buccolabial tooth surface.

The coordinate axes may be conveniently adjusted relative to the tooth in six degrees of freedom. For example, each axis may be translated using a simple click and drag gesture applied to a highlighted section, or "tube", along a given axis. Moreover, each axis may be easily rotated using a "wheel" 158, found at either end of the axis as displayed. Wheels 158 may be activated, for example, using the scroll wheel of a mouse. Advantageously, this allows for easier and faster alignment while reducing the need to orient the dentition surface 100.

As an alternative to using landmarks 140, a "single-click" method may be used to define the coordinate system. This method uses point input data that defines a point on the virtual tooth, receiving axis input data that defines first and second axes associated with the virtual tooth, computing a substantially normal vector for a portion of the tooth surface surrounding the point, and computing the tooth coordinate system based on the axis input and the computed vector. This is particularly useful for determining coordinate axes for incisor, cuspid, and bicuspid teeth, for which the buccolabial surfaces display a relatively small degree of variability. In FIGS. 15-17, this implementation is used for the upper right central tooth surface 152. The creation of the coordinate system can be performed semi-automatically, as will be described below.

Figure 14B:
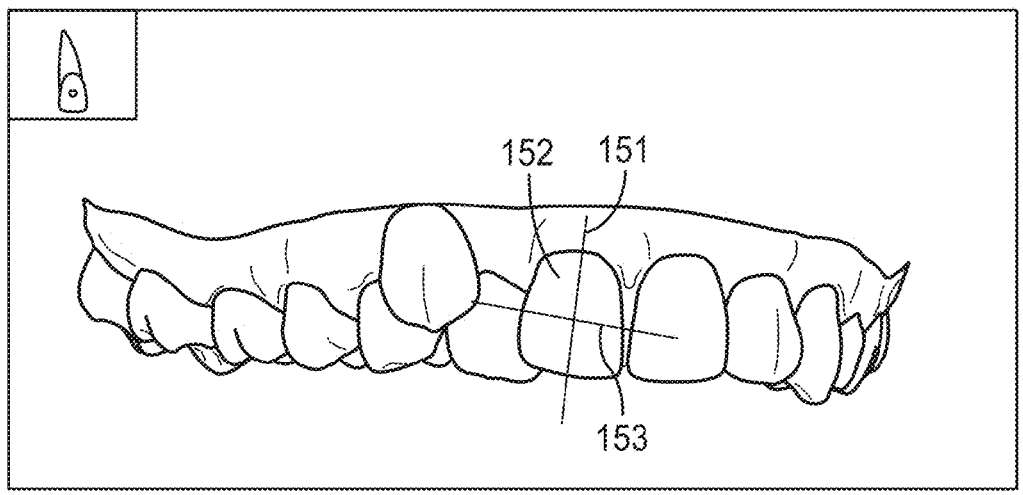
FIG. 14B is a buccolabial view showing horizontal and vertical crosshairs on a tooth surface of the dentition surface of FIGS. 2A-14A.

FIG. 14B shows the use of an oriented crosshairs tool for defining the coordinate system of a tooth surface in a three-dimensional viewing environment. Here, the location of vertical and horizontal crosshairs 151,153 is initially provided by a user, with the vertical crosshair 151 reflecting the perceived z-axis of the tooth surface 152. The point of intersection of the horizontal crosshair 153 and the vertical crosshair 151 defines a perceived reference point, such as the perceived facial axis (FA) point 160 of the tooth surface 152. Advantageously, this user input can be provided using a single click using a cursor control device on the tooth surface 152.

If desired, the horizontal crosshair 154 can be rotated relative to the vertical crosshair 150 such that the crosshairs 150,154 are no longer orthogonal. This rotation can be carried out, for example, by holding down a control key on the keyboard, or entering some other temporary user input mode, while moving the scroll wheel on the mouse (or other pointing device). In the context of an orthodontic prescription, such an adjustment can be useful in representing an adjustment in the angulation (or "tip") of the respective tooth. Advantageously, such an adjustment can express the tip that is built into the anatomy of the patient's dentition such that the correct tip may be applied later when moving the virtual teeth objects toward desired positions.

With the crosshairs 150,154 and the FA point thus defined, the coordinate system can be computed using the FA point as a position reference and using at least one of the crosshairs and a normal vector (or "normal") for a portion of the tooth surface as an orientation reference. The computer can then provide on the user interface visual indicia to represent x, y, and z axes of the tooth coordinate system.

In one embodiment, this can be achieved using the following technique:
 a) A sagittal reference plane P is defined as the intersection of the vertical crosshair 150 with the viewing plane (equivalent to the plane of the page in FIG. 14B). Plane P represents the intersection of the vertical crosshair 150 with an eye point of a virtual camera in the 3D viewing environment shown in FIG. 14B. An intersection is then identified between this plane P and the tooth (the result of this intersection is a polyline). The occlusal-most point of this polyline is used to define the position of the origin of the tooth coordinate system. For bicuspids, a slight variation to this step is used—the lingual portion of the tooth is excluded so that the coordinate system origin is defined using buccolabial cusps only).
 b) A cylinder is created, centered about the center of the crosshair object and normal to the viewplane, with a radius R. In an exemplary embodiment, the radius used is 1 millimeter.
 c) A uniform point sampling within that cylinder is used (in an exemplary embodiment, approximately 25 points are used within this cylindrical region). A ray is extended from each of these points towards the facial surface of the tooth. The intersection with the tooth surface is computed, and the normal at the surface is found. All normals from the point sampling are averaged to find the average normal at the facial surface of the tooth near the FA point. Advantageously, this step removes any spikes that may occur due to local rough surface data.
 d) The average normal, as computed in step c) above, is used to define the y orientation of the coordinate system.
 e) Next, the vertical crosshair is projected onto the plane defined by the coordinate system origin and the y axis orientation as the normal. The result of this projection is the z orientation vector of the coordinate system.
 f) Finally, the x orientation vector is simply the remaining vector (z cross y or y cross z).

Other variants are also possible. For example, the FA point itself could define the origin of the coordinate system. In some embodiments, the array of points in step (c) above lie in a reference plane parallel to the view plane, and are projected onto the tooth along a line passing through an eye point of the virtual camera and the FA point of the tooth. In some embodiments, the array of points are projected onto the tooth along the normal vector determined at the FA point. The array of points need not be derived from a cylindrical region. For example, the array of points may be derived from any geometric shape enclosing a portion of the tooth around the reference point. In any of the above cases, the array of points could be projected onto the tooth along an average normal vector, which is in turn an average of individual normal vectors for respective polygons or vertices used to represent the tooth surface.

Figure 18:
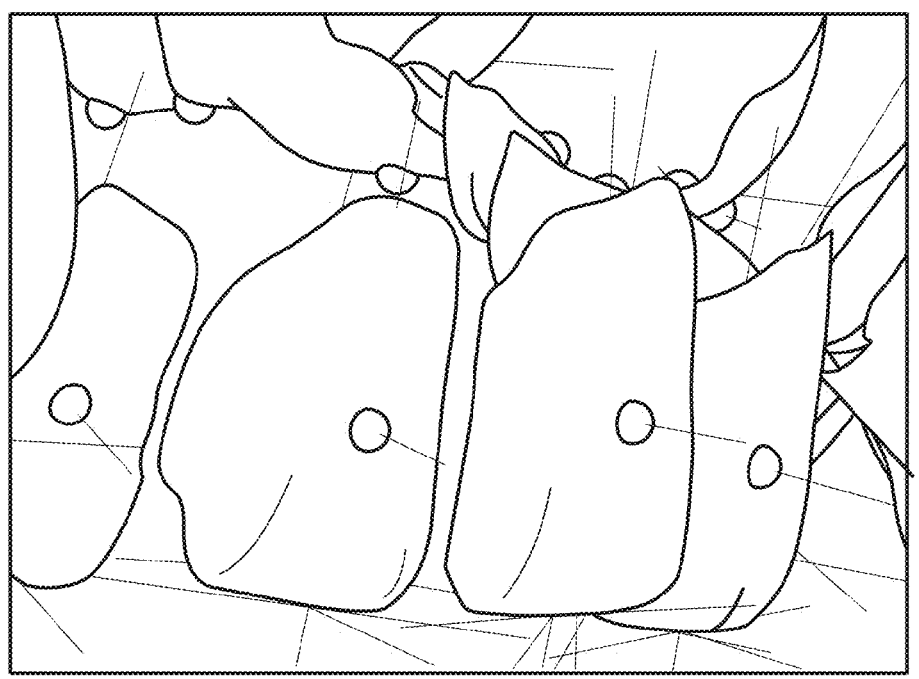
FIG. 18 is a perspective view of tooth surfaces in the dentition surface of FIGS. 2A-17 showing coordinate systems for the tooth surfaces.

FIG. 18 shows an upper dental arch of the dentition surface 100 with the coordinate system defined for all teeth. Also shown, as an additional reference datum, is the normal vector for each tooth as determined in steps a-c above. Advantageously, this method allows a user to compensate for known defects in the tooth structure. As an option, if a user is aware that a cusp has been worn down, the user can intentionally avoid landmarking that cusp, thereby avoiding the effects of this defect when setting the coordinate axes for the respective tooth. Alternatively, such a defect may be remedied by manually adjusting the coordinate axes as described above. If desired, a landmark of the worn cusp can be identified as "suspect" and removed from further calculations while still being noted.

The coordinate system thus defined, the user can then perform various modifications to one or more virtual teeth associated with the coordinate system. This could include, for example, rotation or translation of the tooth along or about a given tooth axis. Such modification could also include the attachment of an orthodontic appliance to a tooth. In a preferred embodiment, the computer updates the user interface to be consistent with the modifications.

Root Stub Formation

Once all of the coordinate systems have been defined, artificial root stubs can be virtually added to each tooth surface such that each tooth surface presents a closed-manifold surface. Referring back to FIG. 1B, this step is represented by Block 58. Root stubs are beneficial in orthodontic digital setups because they reflect the defined coordinate system of each tooth and help a user visualize the orientation of each tooth with respect to its neighbors. Root stubs can also assist in treatment planning. For example, root stubs provide a visualization that can be used by a practitioner to predict possible interferences between roots during treatment.

Figure 19:
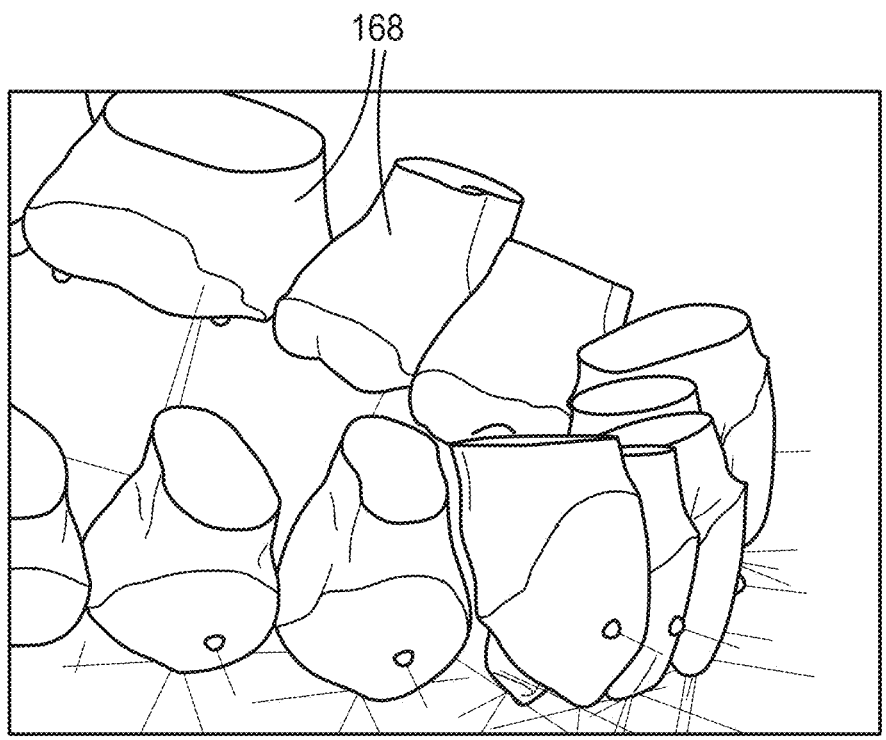
FIG. 19 is a perspective view showing coordinate axes for tooth surfaces with root stubs in the dentition surface of FIGS. 2A-18.

FIG. 19 shows the automated formation of root stubs 168. In a preferred implementation, the root stubs 168 are computed from the finalized coordinate systems of the tooth surfaces and pre-defined characteristic cross-sections of artificial roots. The pre-defined characteristic cross-sections originate from a model (or idealized) tooth, and represent virtual "slices" of the tooth root along planes normal to the z-axis of the model tooth.

The following implementation can be used to integrate the artificial roots with scanned tooth surfaces:

1) An object oriented bounding box is defined for each tooth surface.
2) A second, larger object oriented bounding box is defined for both the tooth surface and root stub based on a predetermined root stub length. Preferably, the predetermined length is hard-coded. Optionally, the predetermined length is uniform for all root stubs.
3) The artificial cross section of the artificial root for each respective tooth is then scaled to the size of the oriented bounding box.
4) Polygons of real scanned points are created in the plane of each artificial cross section.
5) Areas of missing scan data are provided by morphing the cross section points with the tooth surface.
6) Horizontal splines on areas of real scan data are built based on real scan polygons and morphed artificial data.
7) Vertical splines are defined considering the real scan data and the horizontal splines.
8) Splines located in areas without scan data are then smoothed to reduce areas of strong convexity and concavity. The result is a three dimensional grid of spline points defining the surface of the artificial root stub and the interproximal areas of the tooth.
9) The spline data for all artificial parts are then triangulated, or converted to a 3D triangular mesh.
10) Finally, the artificial edges are connected with the real scan data edges to produce tooth surfaces with fully integrated root stubs.

Figure 20:
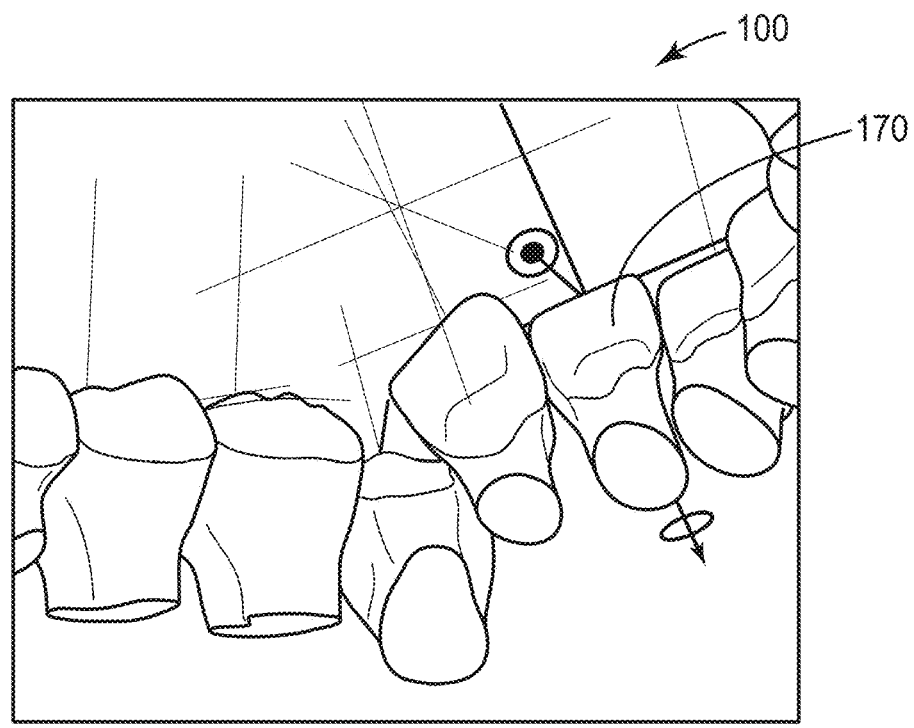
FIG. 20 is a lingual view showing coordinate axes for tooth surfaces with root stubs in the dentition surface of FIGS. 2A-19.

FIG. 20 shows the use of "tube" and "wheel" elements as parts of an adjustment control to manipulate the location and orientation of the integrated tooth elements. This adjustment control differs from the one earlier described as being associated with the tooth coordinate system, because it is associated with the entire tooth. As such, adjustments to this control cause the tooth, along with its coordinate axes, to move relative to the arch, while its coordinate axes maintain their position relative to the tooth geometry. Advantageously, a user can visualize the movement of teeth in response to very small changes in an orthodontic prescription. In the figure, the effect of minor changes in torque and angulation for individual tooth surface 170 is depicted with respect to the surrounding teeth in the dentition surface 100.

Definition of Reference Planes

With the root stubs in place, the user may specify one or both of the occlusal and midsagittal planes of the dentition surface 100 at this time (Block 60 in FIG. 1B). The occlusal plane is an imaginary surface that passes through the occlusion of the teeth, and is generally approximated by a plane. The midsagittal plane is an imaginary plane passing longitudinally through the middle of the dental arch, dividing it into left and right halves.

Figure 21:
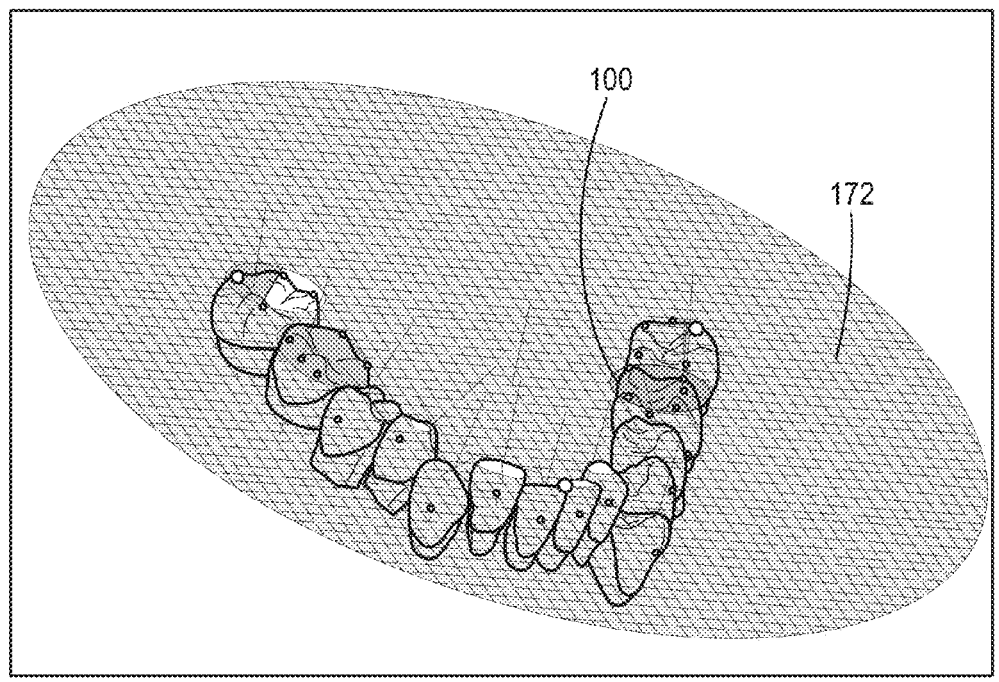
FIG. 21 illustrates the definition of a first reference plane in the dentition surface of FIGS. 2A-20.

FIG. 21 shows the process of deriving an occlusal plane 172 on the dentition surface 100. In one embodiment, the computer provides an initial approximation of the occlusal plane 172 based on the shapes or coordinate systems of some or all of the tooth surfaces belonging to an individual arch of the dentition surface 100. For example, the occlusal plane 172 may be defined by identifying three points that tangentially contact a plane superimposed on the dentition surface 100. For a given dental arch, the three points generally include at least one contact point from a left molar, one contact point from a right molar, and one contact point from a central or lateral tooth. In another embodiment, the occlusal plane is defined as a best-fit plane to the points representing the origins of the tooth coordinate systems, as previously defined. In effect, this plane represents the average of these origins, which are generally positioned at the incisal edges, single cusp tips, or buccal cusp tips of the teeth.

Figure 22:
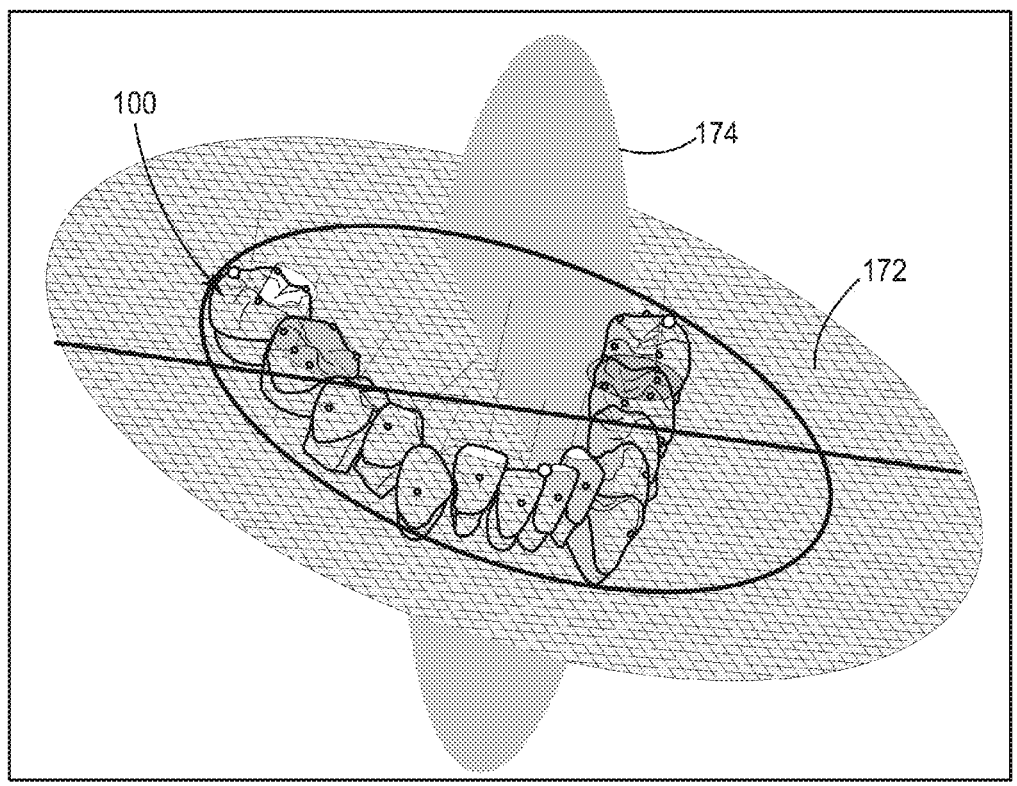
FIG. 22 illustrates the definition of a second reference plane in the dentition surface of FIGS. 2A-21.

FIG. 22 shows the result of deriving the midsagittal plane 174 of the dentition surface 100. The computer derives this plane 174 based on the shape of the archform according to the coordinate systems of the tooth surfaces of the dentition surface 100. With respect to both the occlusal and midsagittal planes 172,174, the computer provides an option to make manual adjustments to their locations and/or orientations relative to the dentition surface 100 as seen fit by the user.

Tooth Placement in Archform

At this point, the dentition surface 100 includes a set of discrete movable tooth surfaces with integrated root stubs. Further, both occlusal and midsagittal reference planes have been defined. At this time, basic diagnostic features are available. For example, the user can superimpose the occlusal plane to examine the patient's dentition for symmetry. The location and orientation of the tooth surfaces are then adjusted to precisely place tooth surfaces in each of the upper and lower archforms, as represented by Block 61 in FIG. 1B.

The tooth surfaces in each archform can be placed according to known guiding principles in orthodontic practice. For example, some of these guiding principles can be found in Dr. Lawrence F. Andrew's "Six Keys to Optimal Occlusion", describing the tooth positions of naturally optimal dentitions. This information is documented in Dr. Andrew's text entitled, *Straight Wire, The Concept and Appliance* (L. A. Wells, 1989).

Preferably, the placement of tooth surfaces in the dentition surface 100 occurs according to one or more quantitative rules. As one example, a rule could require the closure all spaces within a dental arch. In a preferred embodiment, a computer algorithm automatically closes all spaces between tooth surfaces by packing the teeth toward the midline in the dentition surface 100, while constraining all tooth surfaces to the defined archform. A user can also specify that this condition is maintained such that this tooth packing procedure takes place automatically every time a tooth surface is subsequently moved.

The user may specify one or more constraints to the tooth packing process. For example, the user may choose to "pin" one or more tooth surfaces such that these tooth surfaces do not move relative to the dentition surface 100 while the remaining teeth are packed toward the midline. This constraint can be advantageously applied when the user does not wish to disturb the position of one or more of the teeth.

If desired, a virtual archwire may be defined and one or more tooth surfaces can be moved to a specified position along the virtual archwire, as described in issued U.S. Pat. No. 7,354,268 (Raby, et al.). As another option, the positions of the tooth surfaces in the dentition surface 100 can be determined based on a predetermined orthodontic prescription, as described in issued U.S. Pat. No. 7,291,011 (Stark, et al.). The definition of the arch form need not be a spline consisting of a continuous series of circular arc segments, as described in the aforementioned patents. Instead, the arch form may be defined as a spline consisting of a continuous series of parametric cubic curve segments, or according to some other mathematical definition of a continuous curve.

One or more teeth can also be individually adjusted. Aspects that can be adjusted for each tooth surface include: torque, tip, $1^{st}$ order rotation, mesial-distal movement (with or without interproximal reduction (IPR)), occlusal-gingival translation, and buccolabial-lingual translation. Each of these aspects relate to movement in one of the six degrees of freedom defined by the coordinate axes of the respective tooth surface. Corresponding adjustments can be made as previously described for the tooth surface 152 in FIGS. 15-17. Adjustments to one or more individual teeth may be used to implement, for example, a desired Curve of Spee or Curve of Wilson. If buccolabial or lingual braces are intended for use in treatment, adjustments can be made to conform one or more tooth surfaces to a particular archwire plane. Optionally, one or more of these requirements are provided by a orthodontic practitioner.

Figure 23:
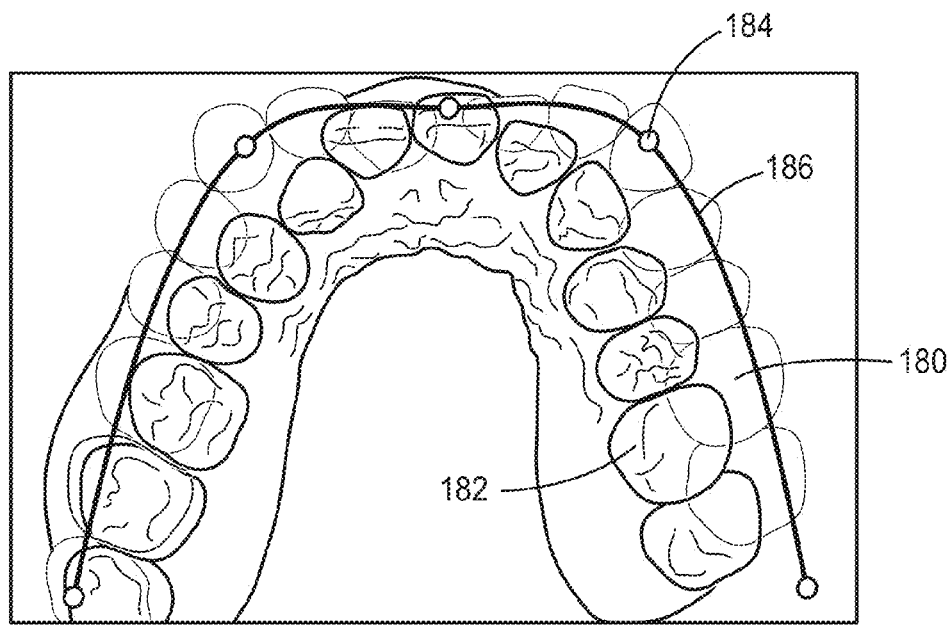
FIG. 23 is an occlusal view showing a superposition between the upper maloccluded reference arch and the same arch undergoing adjustment of the dentition surface of FIGS. 2A-22.

FIG. 23 shows a plurality of teeth objects on upper reference and upper setup arches 180,182 being adjusted in coordinated fashion. As shown in the figure, the user can make an archform adjustment in response to viewing superimposed images of the upper reference arch 180, representing the original malocclusion, and the upper setup dental arch 182 being adjusted to preserve as much as possible the basic shape of the original archform. The shape of the archform is adjusted by clicking and dragging a node 184 on a spline 186 defining the shape of the respective arch. The user may also create additional nodes or control points on the spline 186 to tailor the shape of the archform more precisely.

The manipulation of the tooth surfaces in the dentition surface 100 as described above can be made to satisfy any number of quantitative requirements specified by the orthodontic practitioner, including arch length, intercanine width, intermolar width, and anterior proclination. At the same time, however, there are constraints on the types of tooth movement that are possible, given the physiology of the patient. In the event that it is impossible to satisfy all of the requirements, the user may communicate with the orthodontic practitioner to relax one or more of the requirements and determine an acceptable compromise.

Figure 24:
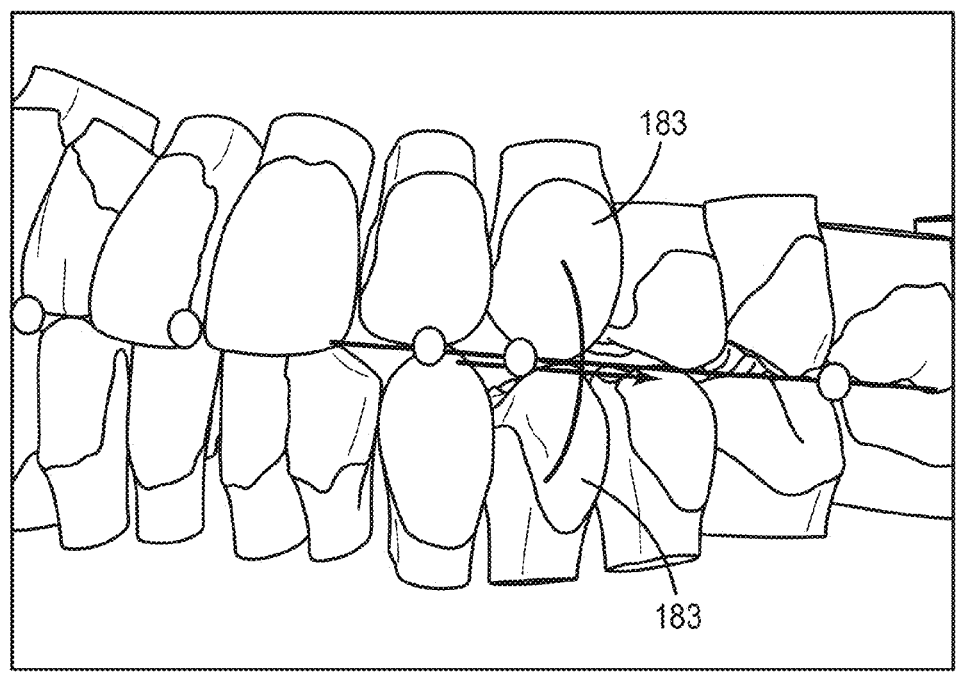
FIG. 24 is a buccolabial view showing collisions being detected between the upper left cuspid and lower left bicuspid and between the upper left cuspid and its mesial and distal neighbors of the dentition surface of FIGS. 2A-23.

When two teeth collide, there are different ways in which the computer can respond to such a collision. In one type of response, the colliding tooth surfaces are allowed to intersect with each other. Optionally and as shown in FIG. 24, the tooth surfaces in collision can be "flagged" (for example, by coloring the tooth surfaces 183 as displayed) to indicate that an intersection between two tooth surfaces has occurred. In a second type of response, the colliding tooth surface simply stops, thereby preventing intersection from occurring. In a third type of response, the colliding tooth is prevented from intersecting with the other tooth while still allowing for limited tooth movement based on the nature of the collision. For example, every manual or input-directed movement of a tooth could be accompanied by an automatic movement that forces the tooth along or about a different axis until contact is made with one or more neighboring teeth. Optionally, the computer provides an option to select the preferred type of response when a user adjusts the positions and locations of one or more tooth surfaces.

The third type of collision response described above can be particularly advantageous because it can simulate the physical and physiological response that occurs when two tooth surfaces collide. While two tooth surfaces may be precluded from direct interferences, it is also possible for a first tooth surface to deflect out of the way and slide past a second tooth surface based on the simulated application of forces (for example, gravity or articulation forces) to the first tooth surface. In other words, input data can be directed to movement of the first tooth that is permissible even when the first and second virtual teeth collide. However, as a result of the collision, the movement of the first tooth can also be restrained along or about a given direction associated with the simulated application of forces. Some of these principles are at work in the algorithms described below and in FIGS. 25-41.

Collision Detection Based on Applied Force

Figure 25:
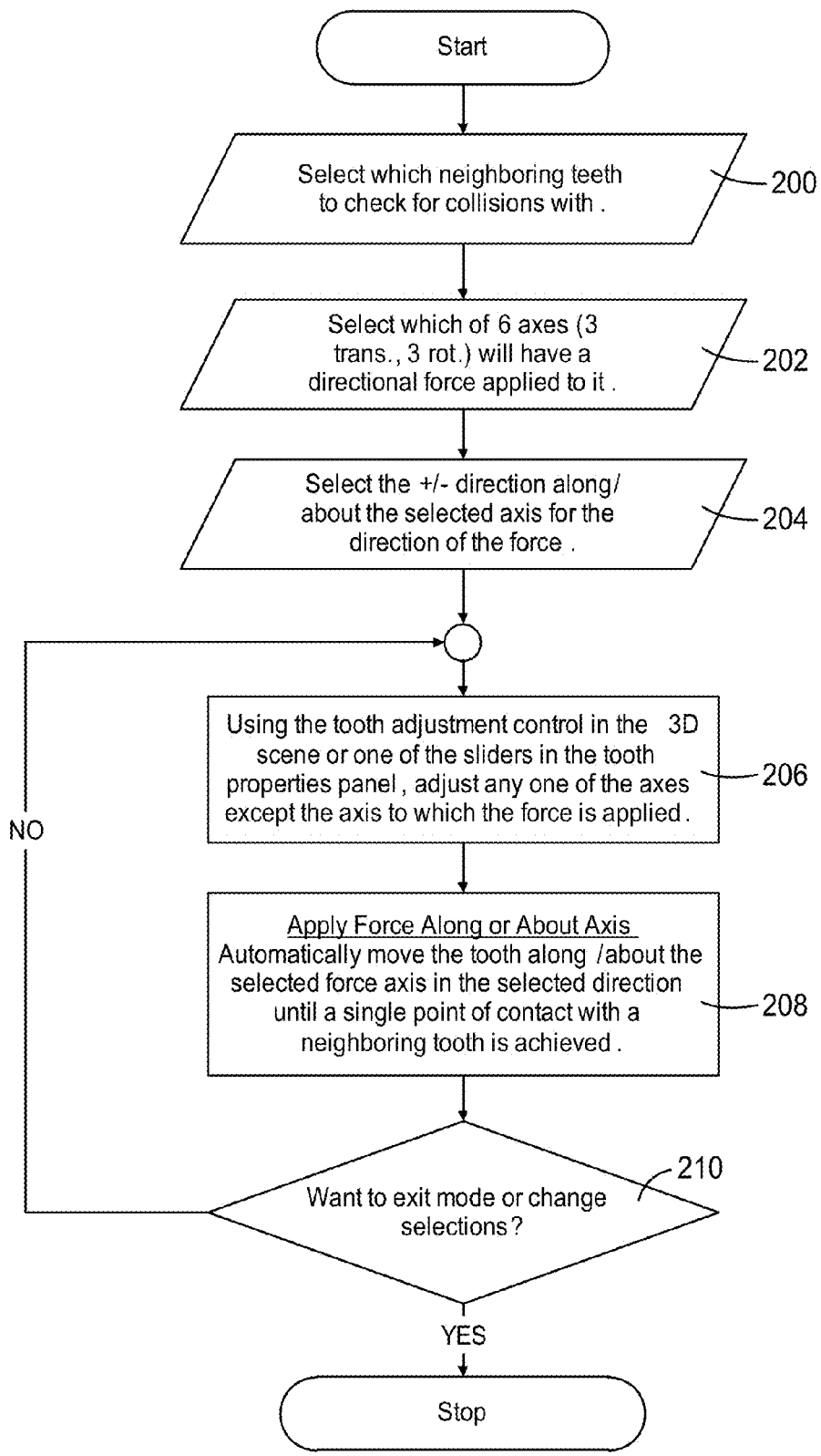
FIG. 25 is a high-level flowchart showing a method of collision prevention between teeth.

FIG. 25 provides an overall flowchart of an algorithm for detecting and responding to tooth-to-tooth collisions encountered when moving a particular tooth surface of interest (i.e. selected tooth) relative to other teeth surfaces. As used herein, the terms "tooth" and "tooth surface" are used interchangeably. For the purposes of collision detection, a tooth may include at least a portion of a natural crown, natural root, artificial crown, veneer, inlay, onlay, implant, bridge, partial denture, or appliance attached to the tooth. Further, the terms "intersection" and "collision" are used interchangeably. This algorithm may be applied to collisions within a dental arch and collisions between opposing dental arches. In the flowcharts, underlined text indicates a reference to a separate function provided in a separate flowchart and described elsewhere in the specification.

Initially, as shown in Block 200, the computer determines which neighboring teeth could present possible collisions with the selected tooth. Generally, these teeth include the mesial and distal neighbors of the selected tooth, along with any opposing teeth on the opposite arch. While a tooth generally has at most one mesial neighbor and at most one distal neighbor, the tooth can have two or more antagonist teeth (i.e. opposing teeth) situated on the opposite dental arch.

In Block 202, the computer selects which of the six axes (i.e. three translational axes and three rotational axes) is associated with the applied force. Proceeding to Block 204, the computer selects the positive or negative direction along/about which the selected axis represents the application of force. For example, the mesial direction can be defined as a positive direction, the distal direction as a negative direction, the occlusal as positive, gingival as negative, and so forth. Preferably, the standards used for positive and negative directions are in accordance with those commonly used in orthodontic appliance prescriptions or specifications.

Next, in Block 206, one or more of the axes other than the selected force axis can be adjusted. This can be carried out by a user using a suitable user interface. For example, these adjustments can be inputs from a tooth adjustment control attached to a 3D dentition surface or sliders in a tooth properties panel. The selected tooth preferably moves by a small increment along or about the manually adjusted axis.

Referring now to Block 208, a function is executed to apply a force along or about the selected axis in the selected direction until a single point of contact with a neighboring tooth is achieved. In other words, if the selected tooth is intersecting a neighboring tooth in the direction of the force, the selected tooth is first moved back until the intersection is eliminated.

In Block 210, the user then has the option of exiting setup mode in the software or changing selections. If either condition holds true, then the process returns to Block 206; otherwise, the process ends.

Applying Force Along/about an Axis

Figure 26:
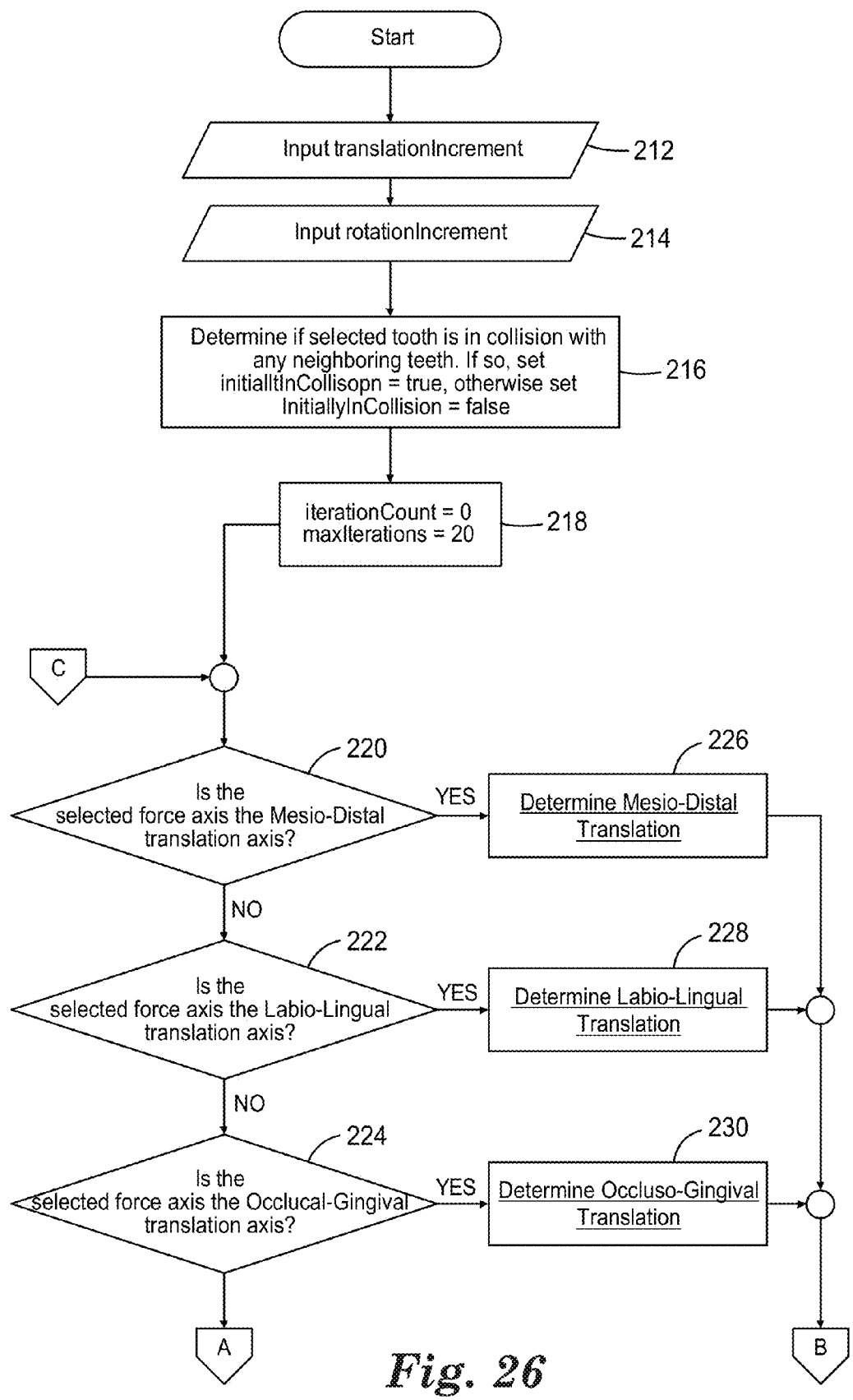
FIGS. 26-28 are a flowchart showing a method of applying a force to a tooth along or about a selected axis.

FIG. 26 provides a flowchart showing in more detail the function of applying force along or about an axis, as represented by Block 208. First, as shown in Blocks 212, 214, a suitable translation or rotation increment is initially provided. In this embodiment, the translation or rotation increment is provided as a function parameter.

Proceeding to Block 216, the computer determines if the selected tooth is in collision with any neighboring (mesial/distal/antagonist) teeth. Here, the neighboring teeth considered are the ones previously selected in Block 200. A Boolean variable, initiallyInCollision, is set to "true" if the selected tooth is in collision with a neighboring tooth and "false" if the selected tooth is not in collision with any neighboring teeth.

In Block 218, an iteration counter is set to 0 and the maximum number of iterations, maxIterations, is set to some predefined quantity (for example, 20). Next, the workflow then continues to one or more of Blocks 220,222,224. Each of the Blocks 220,222,224 determines if the force axis selected in Block 202 corresponds to one of the three translation axes (mesio-distal, buccolabial-lingual, or occlusal-gingival). If this condition is met, then the computer executes a separate function, represented by Block 226,228,230, to determine the respective mesio-distal, buccolabial-lingual, or occlusal-gingival translation, responsive to the applied force.

Figure 27:
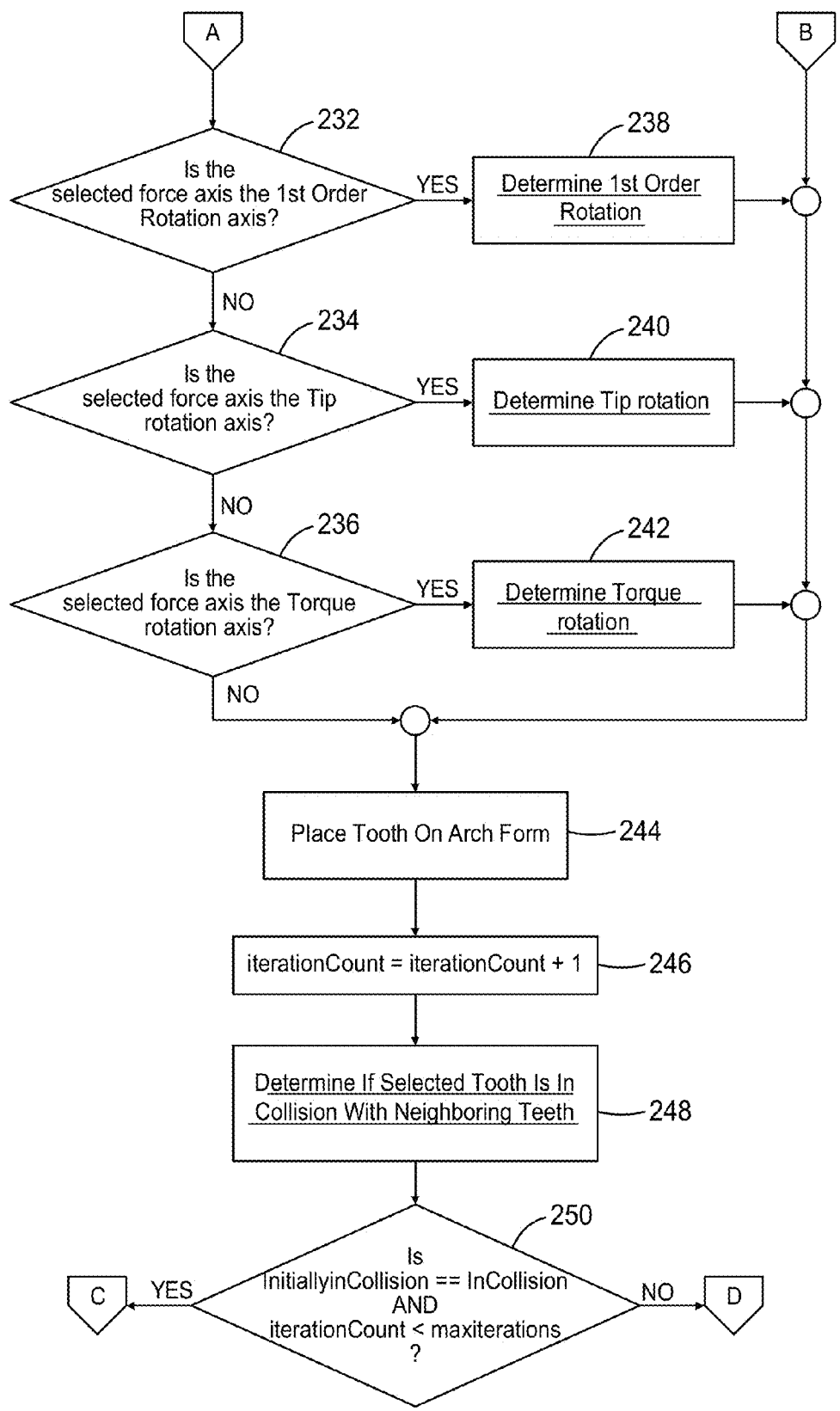
Figure 28:
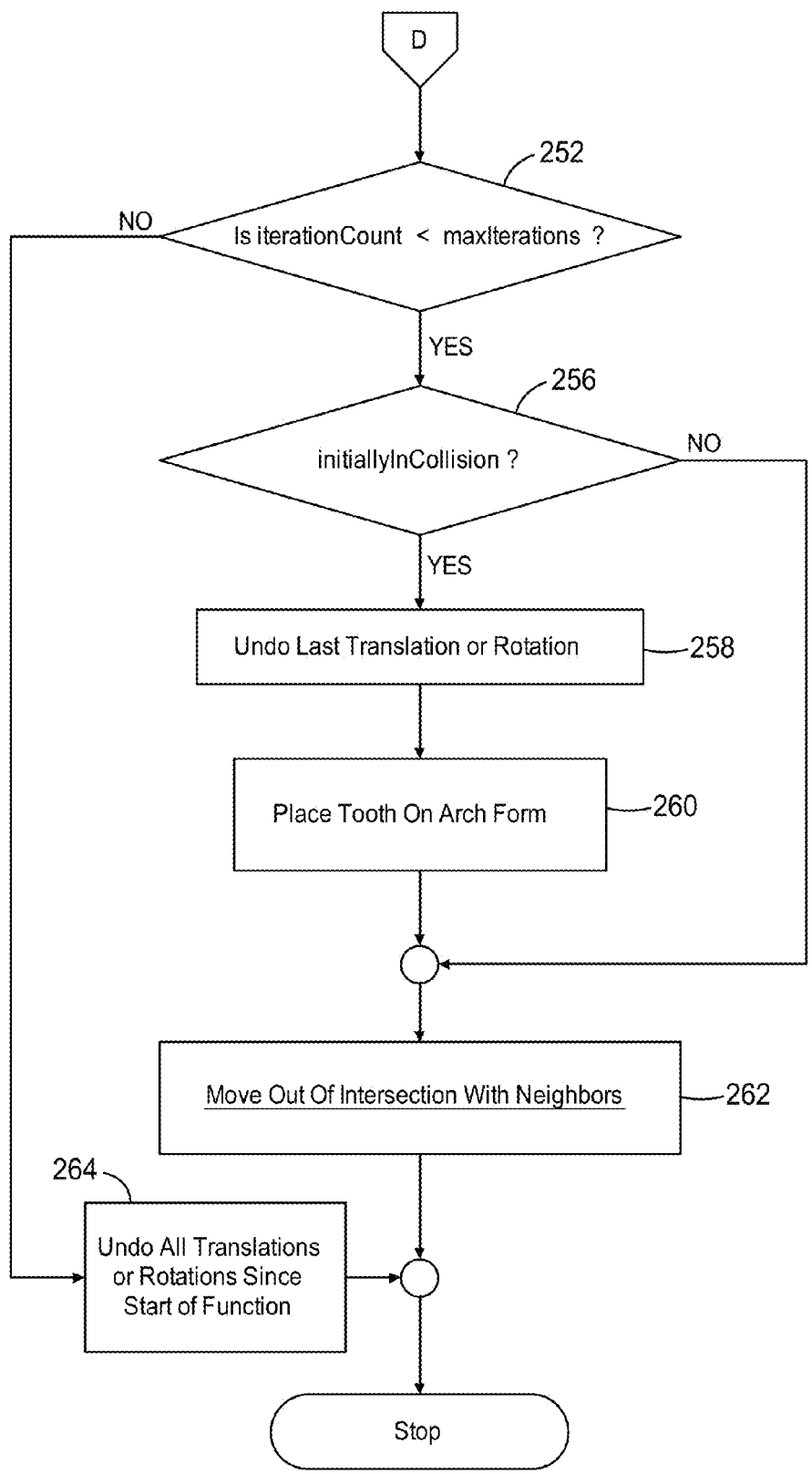

If the selected force axis does not correspond to one of the three translation axes, then the workflow proceeds to the flowchart shown in FIG. 27. As indicated by Blocks 232, 234,236, the computer determines if the selected axis is one of the three rotation axes ($1^{st}$ order rotation, tip rotation, or torque rotation). If one of these rotation axes applies, then the appropriate $1^{st}$ order rotation, tip rotation, or torque rotation is then determined according to one of Blocks 238,240,242.

As shown in Block 244, the selected tooth is then replaced on the archform using the most current translation and rotation settings. The tooth should now have a location or orientation that is adjusted slightly based on the translation or rotation determined in Block 226,228,230,238,240,242. Moving to Block 246, the iteration count is incremented by 1. Then, in Block 248, the computer determines if the selected tooth is in a state of collision with any of its neighboring teeth. If so, the Boolean variable inCollision is set to "true"; otherwise it is set to "false."

Block 250 shows the last step in the iteration, where the computer determines if the Boolean values of initiallyInCollision and inCollision are the same, AND if the maximum number of iterations has not been reached. If both of these conditions are met, then the workflow returns back to Block 220 and the process reiterates as described above. If both conditions are not met, then the process continues to Block 252 of the flowchart in FIG. 28.

Block 252 determines the reason for exiting the iterative loop described above in FIGS. 26,27. If the process exited the loop because the value of inCollision did not change within a reasonable number of iterations, then the process goes to Block 254, where all changes to the rotation/translation are undone. Said another way, the Block 254 causes a reversion back to the original value of the respective DistanceFromMidline, TranslationNormalToArchform, Eminence, FirstOrderRotation, Tip, or Torque, depending on the selected force axis (see FIG. 25).

If, on the other hand, the value of inCollision changed within a reasonable number of iterations (fewer then MaxIteration), then the process continues with Block 256. Block 256 determines if the tooth is initially in collision, based on the value of initiallyInCollision.

If initiallyInCollision is TRUE, then the tooth is taken out of collision by undoing the last translation or rotation (set out in Block 258), or a reversion back to the previous value of the respective DistanceFromMidline, TranslationNormalToArchform, Eminence, FirstOrderRotation, Tip, or Torque, depending on the selected force axis (from FIG. 25). Referring now to Block 260, the tooth is then replaced on the archform with the current location and orientation settings, and the process moves to Block 262.

If initiallyInCollision is FALSE, then no adjustments to location or orientation are required and the process moves directly to Block 262.

In Block 262, the tooth is moved out of intersection with neighboring teeth. This is described in more detail in a subsequent section.

Determining Translations/Rotations

This section describes six separate flowcharts (FIGS. 29-34) used to determine each of three possible translations and three possible rotations according to six degrees of freedom for the selected tooth.

Figure 29:
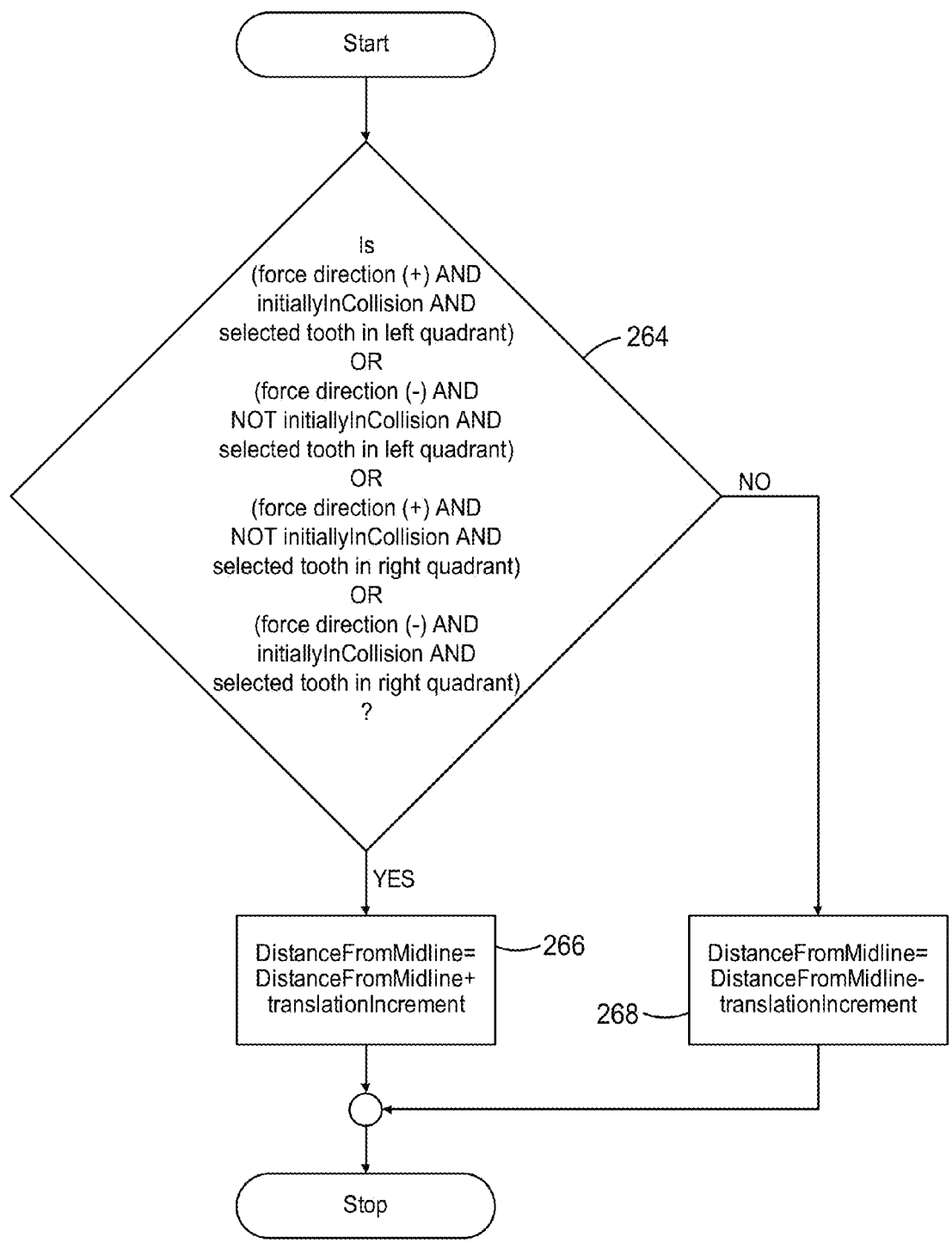
FIG. 29 is a flowchart showing a method of determining mesial-distal translation for a tooth as required in FIG. 26.

FIG. 29 shows the process of determining translation along the mesial-distal axis. Block 264 sets the direction of the movement based on a combination of three factors: the force direction, whether the selected tooth is in collision, and the quadrant in which the selected tooth is located. For example, if the selected tooth is in a state of collision, the direction will be set to move the tooth away from collision. As another example, the direction of positive mesial-distal force is reversed when crossing over from a left to a right quadrant (or vice-versa) because this traverses the origin of the coordinate system for these forces.

Based on whether a positive or negative translation is required, the process proceeds to either Block 266 or Block 268 to increment or decrement DistanceFrom Midline, respectively. Here, the magnitude of the increment or decrement is previously defined by Block 212 in FIG. 26.

Figure 30:
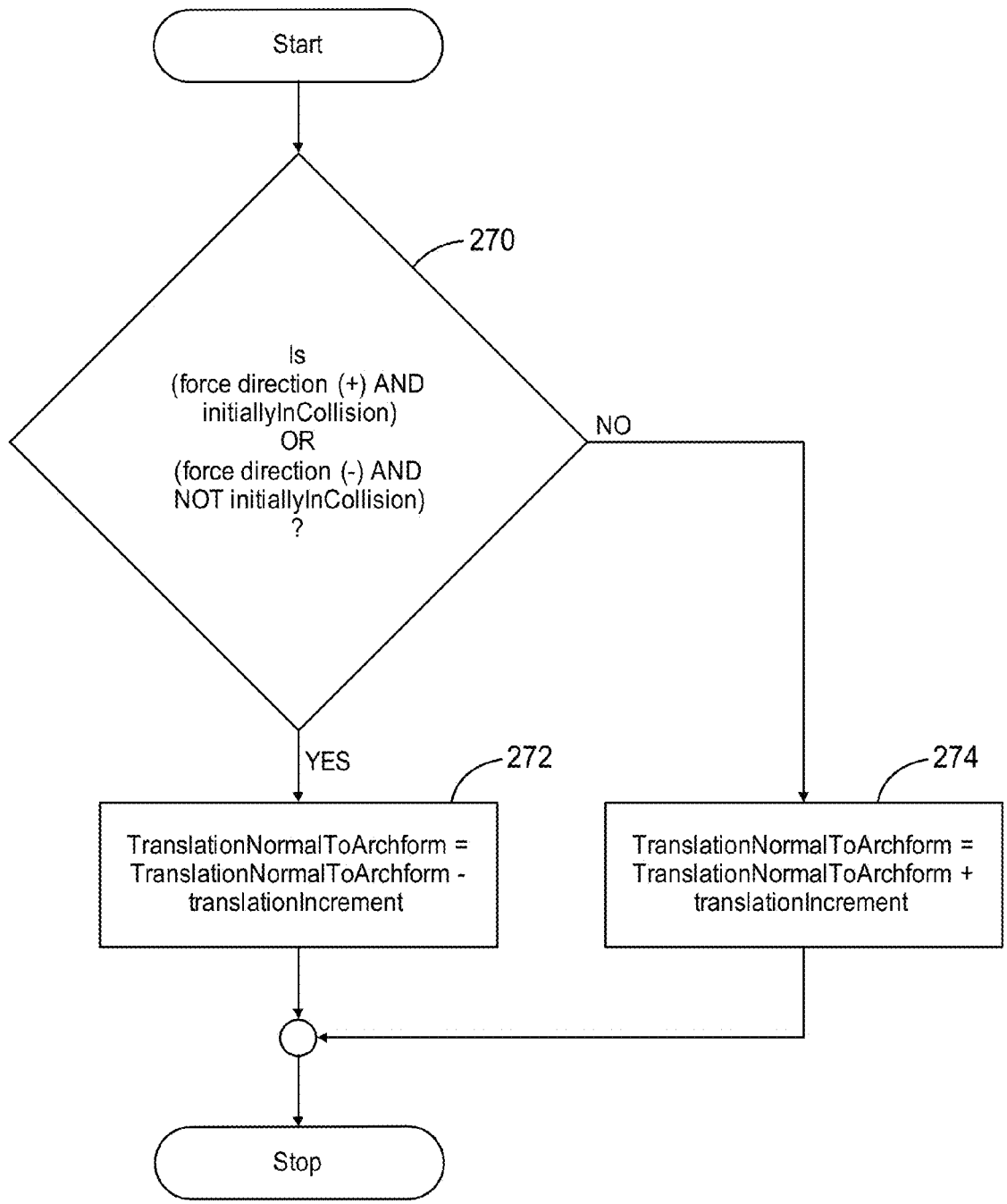
FIG. 30 is a flowchart showing a method of determining buccolabial-lingual translation for a tooth as required in FIG. 26.

FIG. 30 shows the process of determining translation along the buccolabial-lingual axis. In this case, Block 270 sets out the direction of movement, as determined by only two factors: the force direction and whether the selected tooth is in collision. Depending on whether a positive or negative translation is required, the process proceeds to either Block 272 or Block 274 to decrement or increment TranslationNormalToArchForm, respectively. The magnitude of the increment or decrement to TranslationNormalToArchForm is previously defined by Block 212 in FIG. 26.

Figure 31:
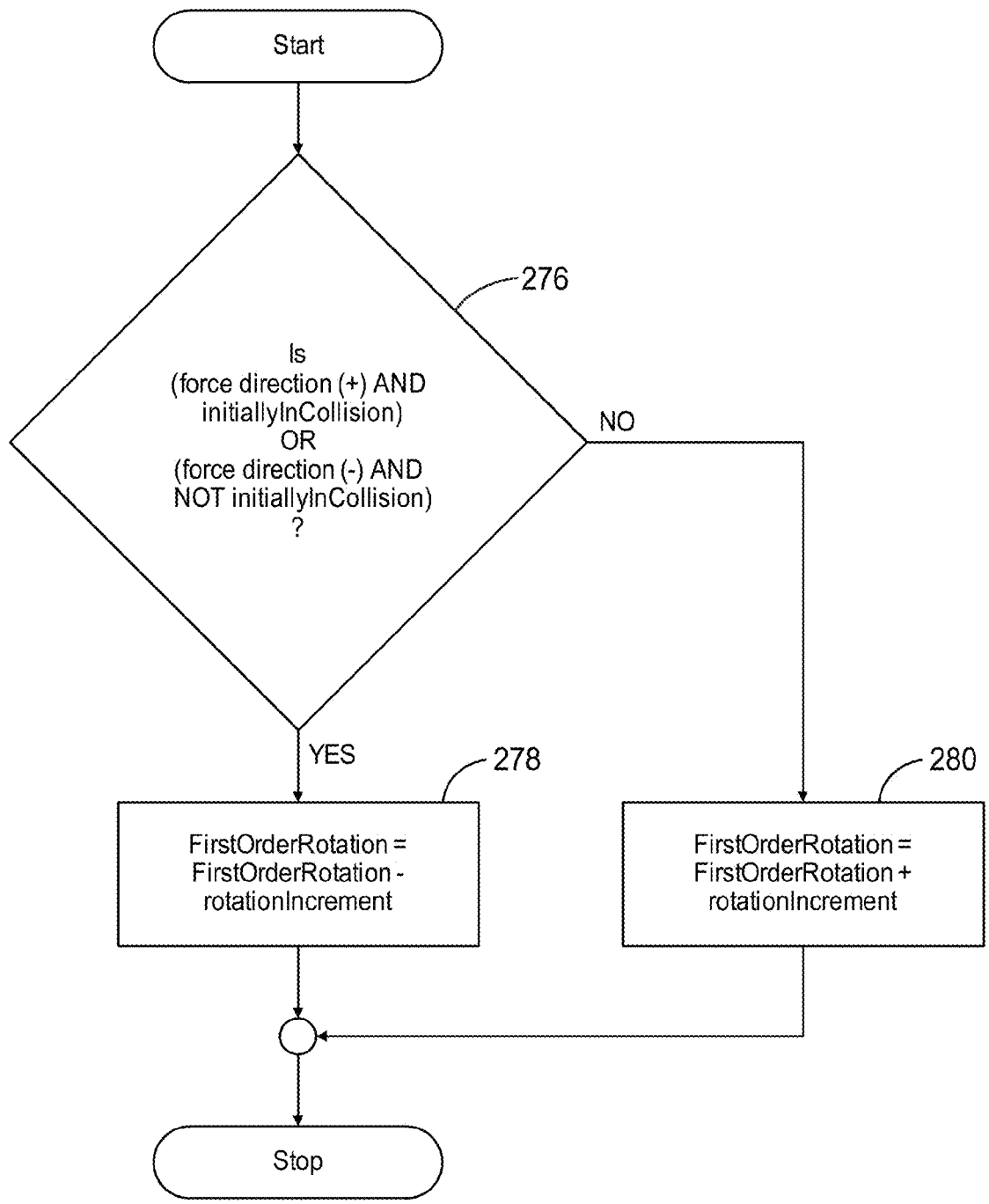
FIG. 31 is a flowchart showing a method of determining occlusal-gingival translation for a tooth as required in FIG. 26.

FIG. 31 shows the process of determining translation along the occlusal-gingival axis. Block 276 sets out the direction of movement, as determined by the force direction and whether the selected tooth is in collision. Depending on whether a positive or negative translation is required, the process proceeds to either Block 278 or Block 280 to increment or decrement Eminence, respectively. The magnitude of the increment or decrement to Eminence is previously defined by Block 212 in FIG. 26.

Figure 32:
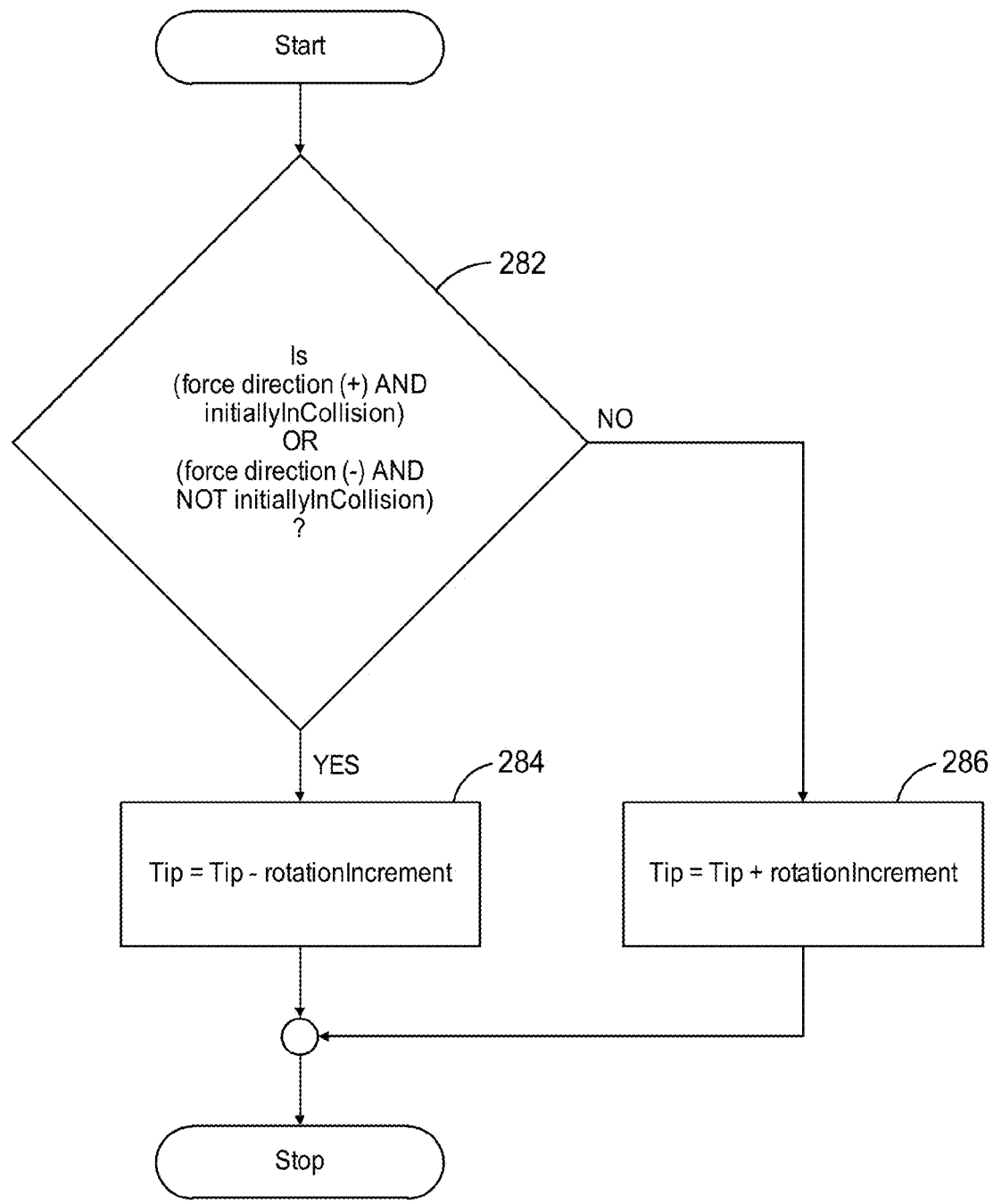
FIG. 32 is a flowchart showing a method of determining first order rotation for a tooth as required in FIG. 27.

FIG. 32 shows the process of determining first order rotation along the occlusal-gingival axis (or longitudinal axis of the tooth). Block 282 sets out the direction of movement, as determined by the force direction and whether the selected tooth is in collision. Depending on whether a positive or negative translation is required, the process proceeds to either Block 284 or Block 286 to decrement or increment FirstOrderRotation, respectively. The magnitude of the increment or decrement to FirstOrderRotation is previously defined by Block 214 in FIG. 26.

Figure 33:
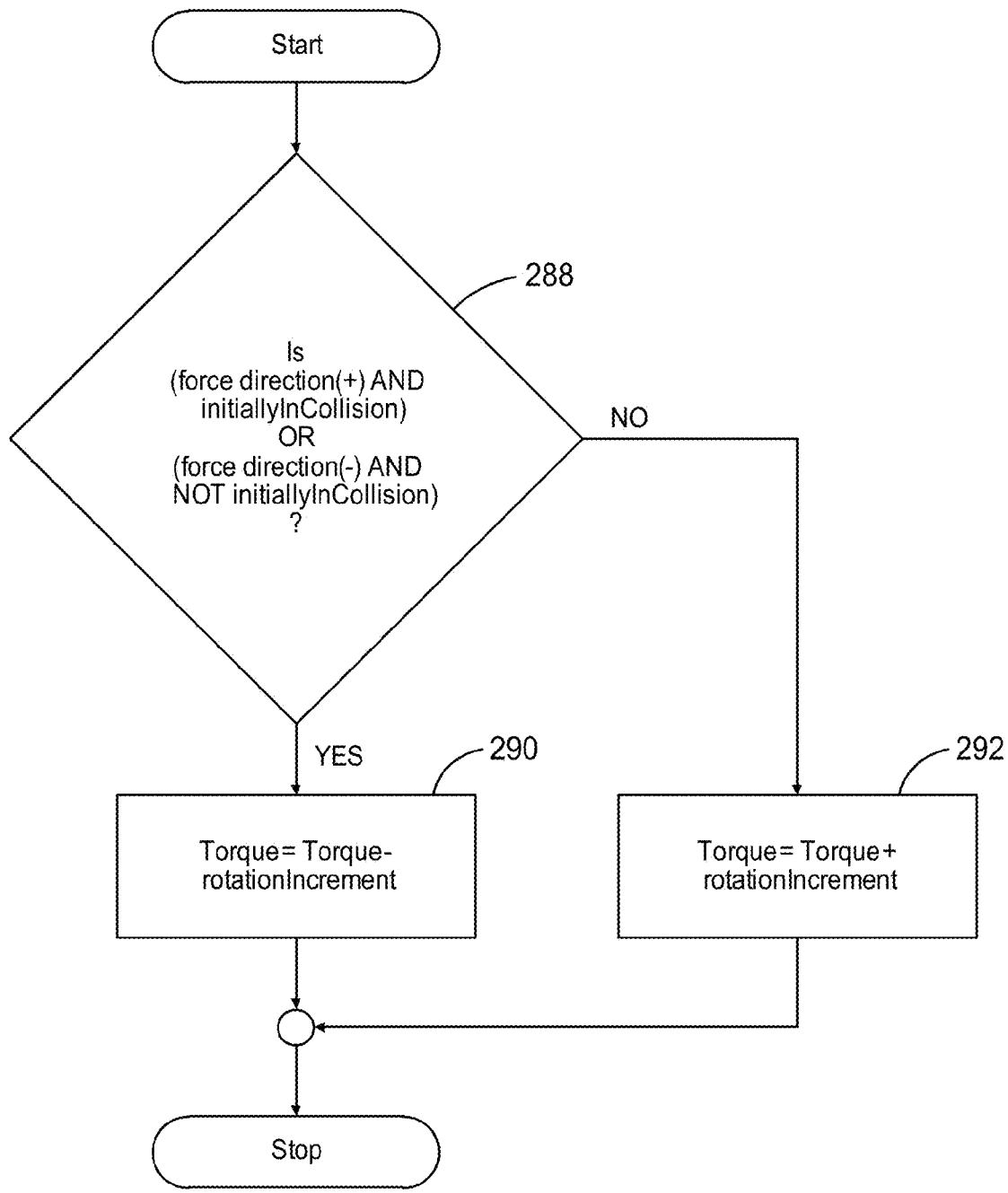
FIG. 33 is a flowchart showing a method of determining tip rotation for a tooth as required in FIG. 27.

FIG. 33 shows the process of determining tip rotation along the buccolabial-lingual axis. Block 288 sets out the direction of movement, as determined by the force direction and whether the selected tooth is in collision. Depending on whether a positive or negative translation is required, the process proceeds to either Block 290 or Block 292 to decrement or increment Tip, respectively. The magnitude of the increment or decrement to Tip is previously defined by Block 214 in FIG. 26.

Figure 34:
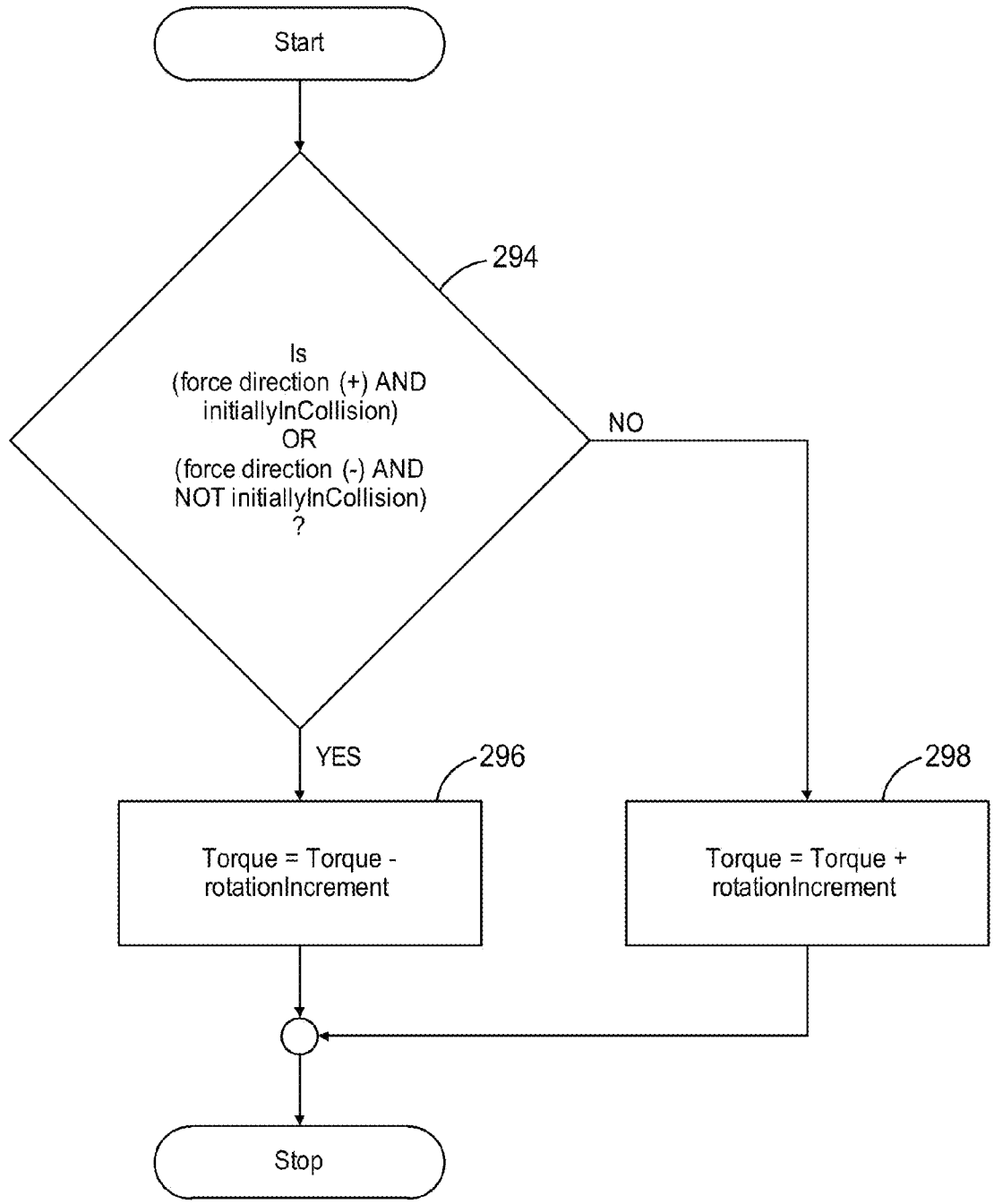
FIG. 34 is a flowchart showing a method of determining torque rotation for a tooth as required in FIG. 27.

FIG. 34 shows the process of determining torque rotation about the mesial-distal axis. Block 294 sets out the direction of movement, as determined by the force direction and whether the selected tooth is in collision. Depending on whether a positive or negative translation is required, the process proceeds to either Block 296 or Block 298 to decrement or increment Torque, respectively. The magnitude of the increment or decrement to Torque is previously defined by Block 214 in FIG. 26.

Determine if the Selected Tooth is in Collision

Figure 35:
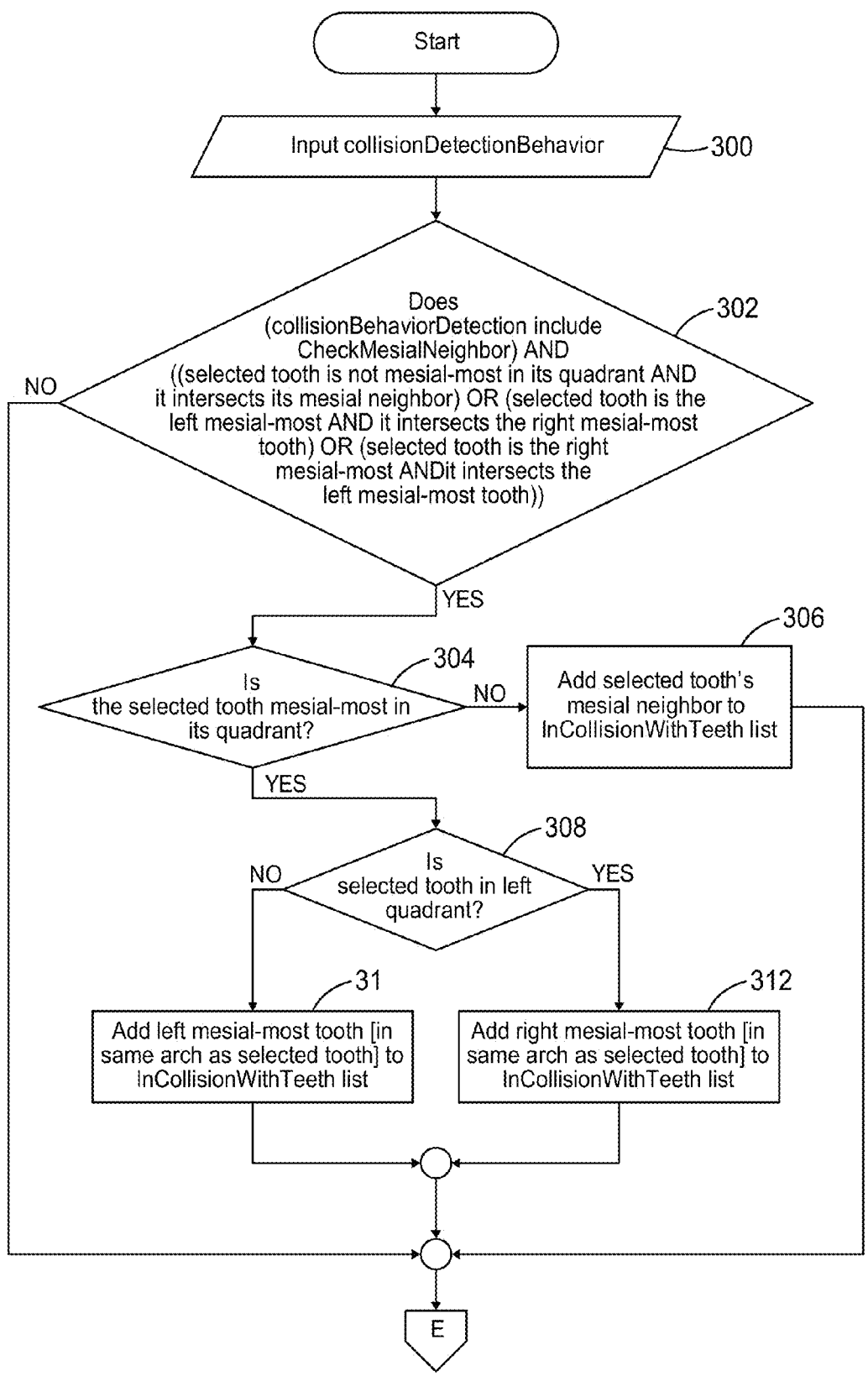
FIGS. 35-36 are a flowchart showing a method of determining if a tooth is in collision with a neighboring tooth.
Figure 36:
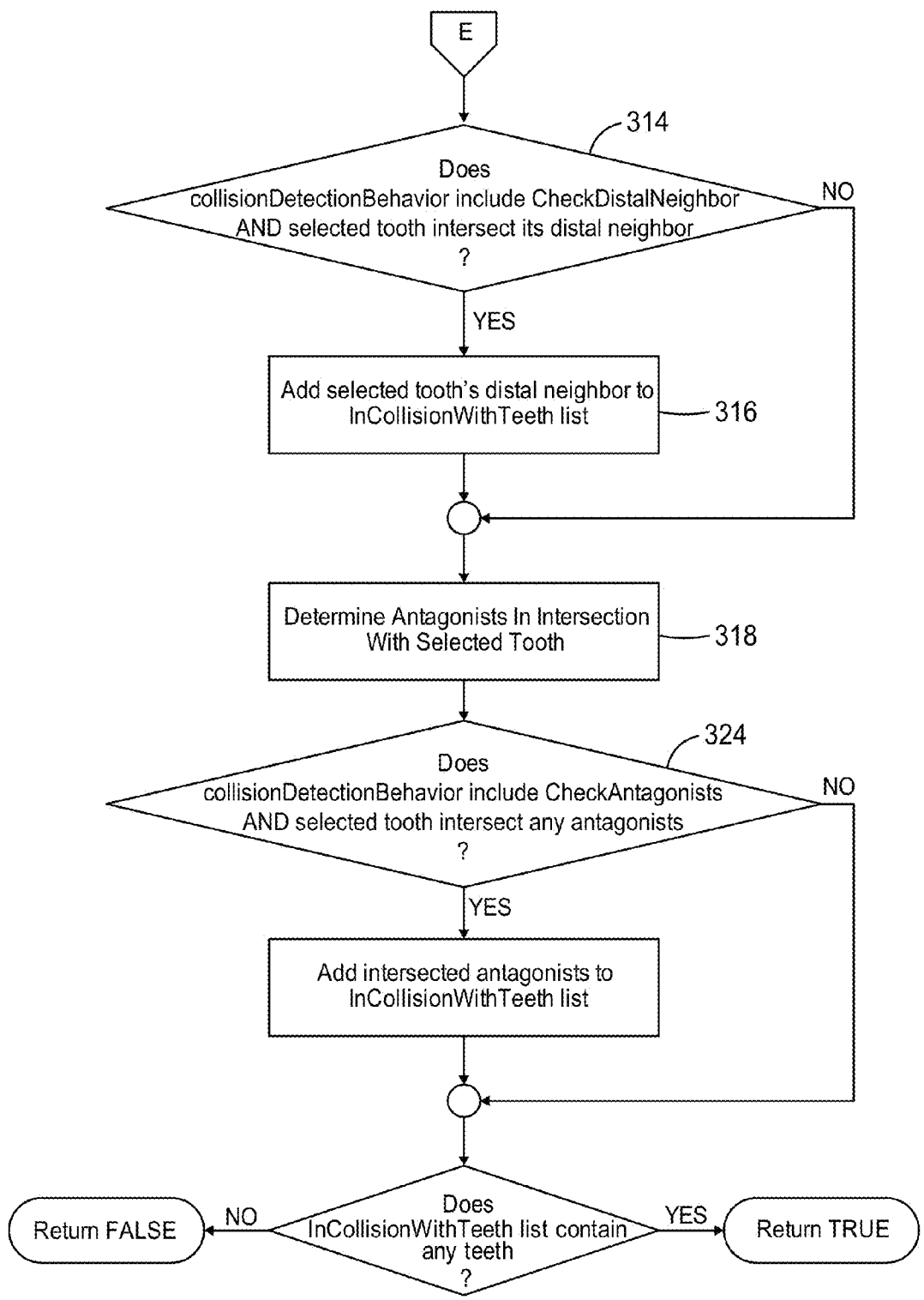

FIGS. 35-36 are flowcharts that describe an exemplary process for determining if the selected tooth is in collision with a neighboring tooth. In FIG. 35, the type of collision is initially specified, as indicated by Block 300. In this example, this input is provided as a function parameter, selected from three possible values: CheckMesialNeighbor, CheckDistalNeighbor, and CheckAntagonists.

Block 302 represents a test to determine if there is a collision between the selected tooth and its mesial neighbor. Optionally, and as shown in Block 302, such a collision exists when the selected tooth is not the mesial-most tooth and it intersects its mesial neighbor, or the selected tooth is a mesial-most tooth and it intersects a mesial-most tooth on the opposite quadrant (left versus right, and vice-versa).

If the condition is not satisfied, then the process continues on to the flowchart of FIG. 36.

If this condition is satisfied, the process proceeds to Block 304, which inquires if the selected tooth is the mesial-most in its respective quadrant. If this is not the case, then the selected tooth's mesial neighbor is noted as being in collision with the selected tooth in Block 306—in other words, it is added to the inCollisionWithTeeth list. The process then proceeds to the flowchart of FIG. 36. If the selected tooth is the mesial-most in its quadrant, then the process proceeds to Block 308, which determines the quadrant of the selected tooth. Based on this determination, either the left mesial-most tooth (Block 310) or the right-mesial most tooth (Block 312) is added to the inCollisionWithTeeth list.

In FIG. 36, the process continues with Block 314, which checks for collisions with a distal neighbor, if applicable. If an intersection between the selected tooth and distal neighbor is detected, then the distal neighbor is added to the inCollisionWithTeeth list (Block 316). Either way, the process then moves to Block 318, where a separate function is executed to determine if there are any antagonist teeth intersecting with the selected tooth.

Moving on to Block 320, if the selected tooth is determined to intersect with one or more antagonist teeth and CheckAntagonists is selected, then any intersecting antagonist teeth are added to the inCollisionWithTeeth list (Block 322). As shown in FIG. 36, whether or not the condition in Block 320 is satisfied, the process proceeds to Block 324. Block 324 determines if the inCollisionWithTeeth list contains any teeth. If yes, the function returns the value TRUE; otherwise, the function returns the value FALSE.

Determining Antagonist Teeth Intersecting with Selected Tooth

Figure 37:
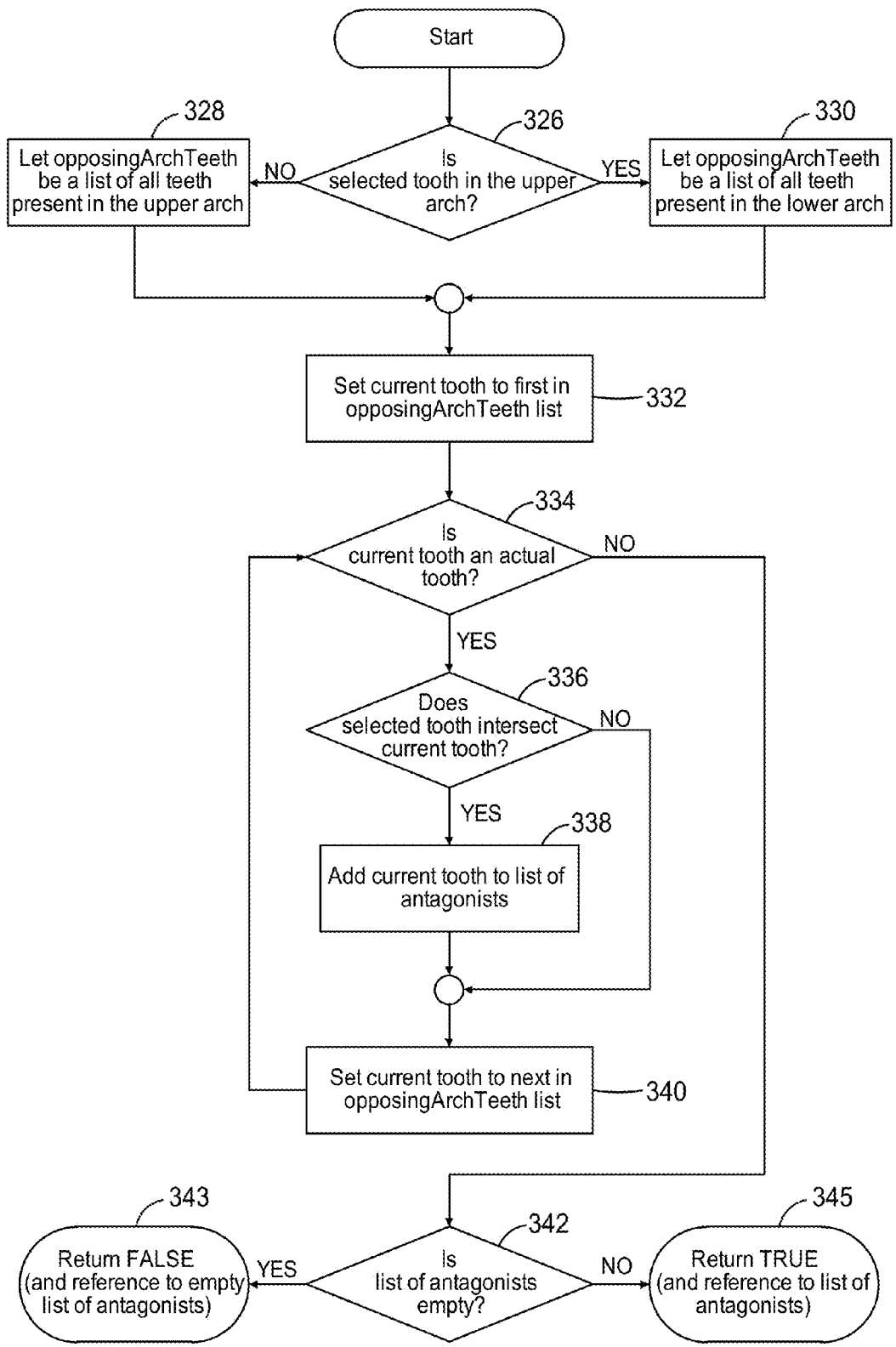
FIG. 37 is a flowchart showing a method of determining which antagonist teeth may be in collision with a tooth.
Figure 38:
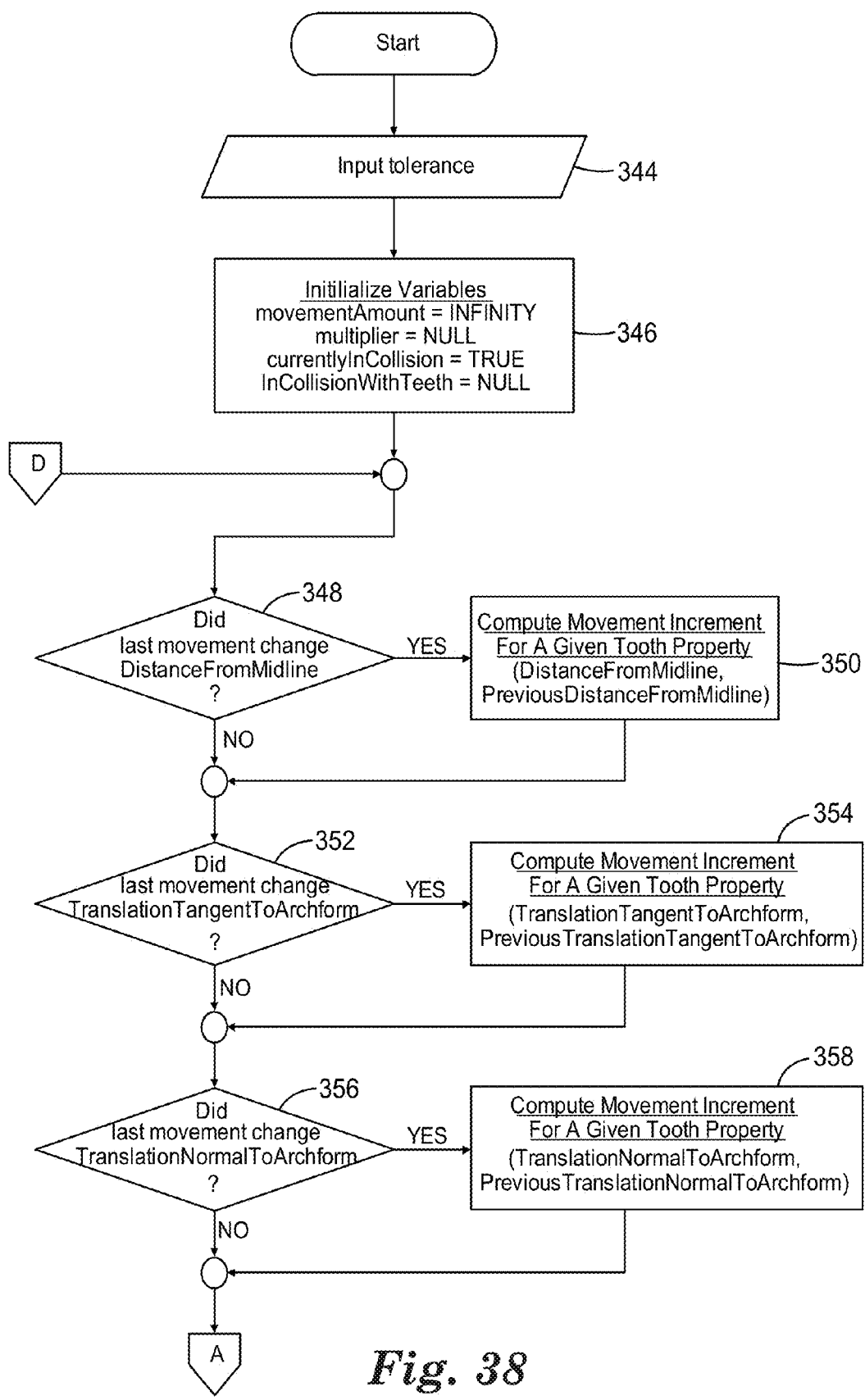
FIGS. 38-40 are a flowchart showing a method of moving a tooth out of collision with its neighboring teeth.
Figure 39:
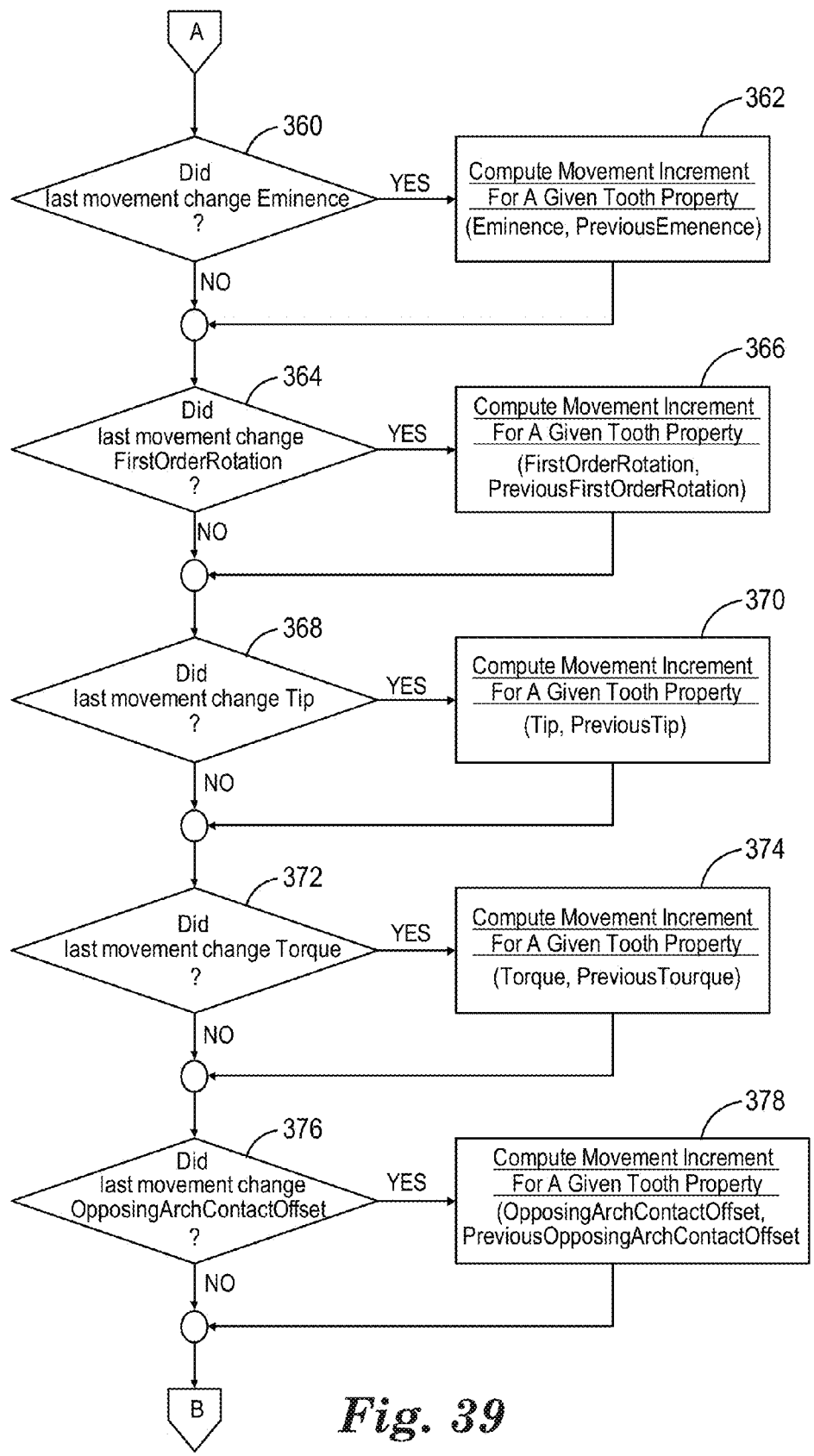
Figure 40:
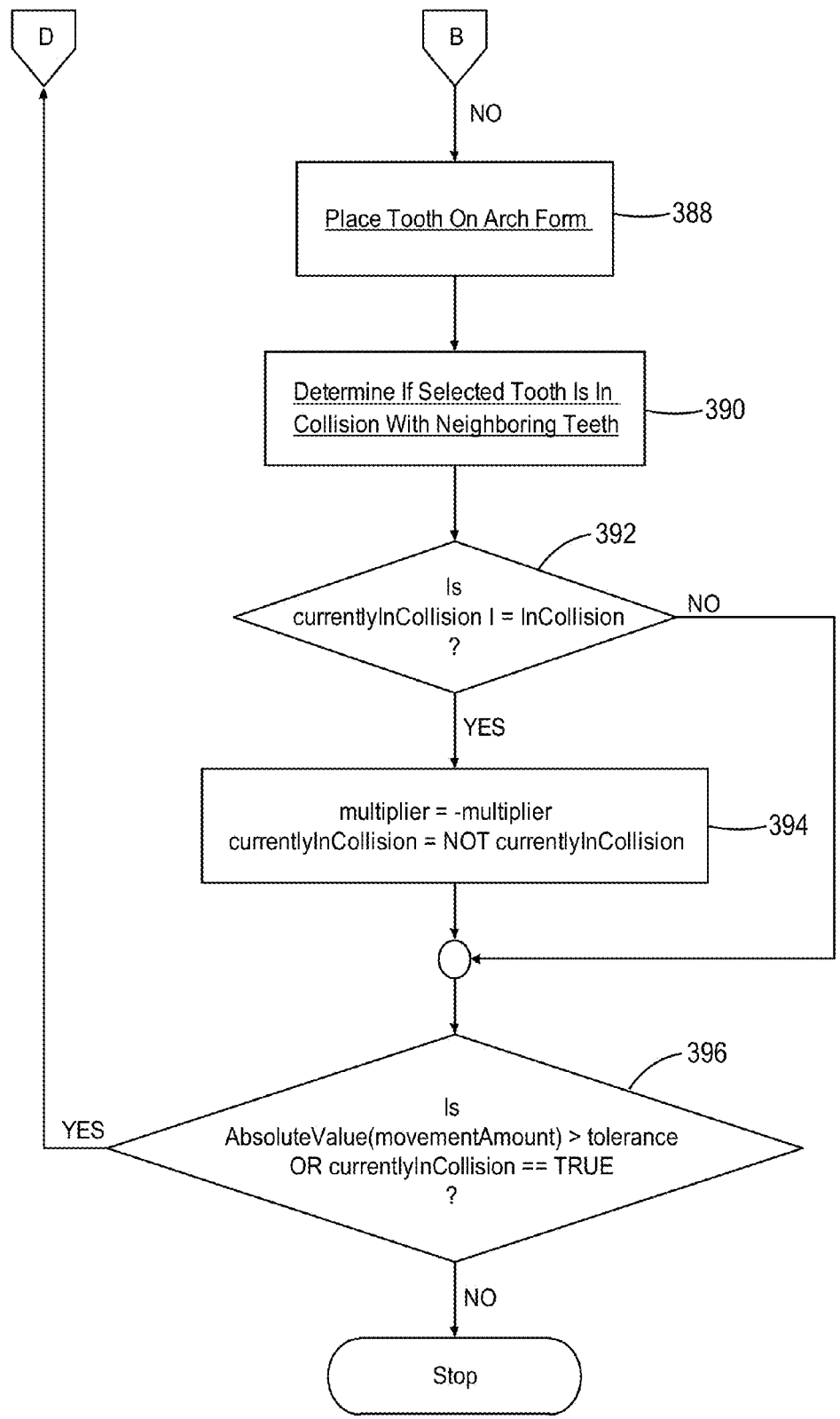

The flowchart of FIG. 37 provides a function determining if any antagonist teeth intersect with the selected tooth. Block 326 determines if the selected tooth resides in the upper arch or the lower arch. OpposingArchTeeth is then defined to include all of the teeth in the arch opposite that containing the selected tooth (Blocks 328,330). Proceeding to Block 332, the current tooth is set to be the first tooth in the list of OpposingArchTeeth. An iterative process then executes. Block 334 inquires if the current tooth is an actual tooth, and not a null value. Assuming that the current tooth is an actual tooth, Block 336 determines if the selected tooth intersects with the current tooth. If so, then the current tooth is added to the list of antagonist teeth (Block 338). Either way, the process continues to Block 340, which sets the current tooth to the next tooth in the list of OpposingArchTeeth. From here, the process repeats itself starting from Block 334 as shown in FIG. 37 until all teeth enumerated by OpposingArchTeeth have been tested.

Finally, Block 342 determines if any antagonist teeth were found. If so, the function returns the value TRUE (Block 345); otherwise, the function returns the value FALSE (Block 343).

Moving Selected Tooth Out of Collision with Neighbors

An exemplary process used to move the selected tooth out of a state of collision with a neighboring tooth is described in four-part flowchart shown in FIGS. 38-41. To begin, Block 344 determines a tolerance value to determine the point at which collision is deemed eliminated. In this example, the tolerance is a function parameter and is defined such that contact between the selected tooth and neighboring teeth is satisfied when the closest distance between the two falls within this tolerance.

In Block 346, various variables are initialized. In the example presented, multiplier is set at NULL, currentlyInCollision is set at TRUE, and inCollisionWithTeeth is set at NULL.

Block 348 marks the beginning of a loop that repeats until contact between the selected tooth and a neighboring tooth is achieved within tolerance. Movements are then probed according to each of eight types of movement, described below.

Block 348 determines if the last movement of the selected tooth changed DistanceFromMidline. If so, then Block 350 is executed, which computes the appropriate movement increment for the given tooth property. Here, for example, the movement increment could be computed based on two variables: DistanceFromMidline and PreviousDistanceFromMidline. As shown, the process then continues with Block 352.

Block 352 determines if the last movement of the selected tooth changed TranslationTangentToArchform. If so, then Block 354 is executed, which computes the corresponding movement increment computed based on TranslationTangentToArchform and PreviousTranslationTangentToArchform. As shown, the process then continues with Block 356.

Block 356 determines if the last movement of the selected tooth changed TranslationNormalToArchform. If so, then Block 358 is executed, which computes the corresponding movement increment computed based on TranslationNormalToArchform and PreviousTranslationNormalToArchform. As shown, the process then continues with Block 360 in FIG. 39.

Block 360 determines if the last movement of the selected tooth changed Eminence. If so, then Block 362 is executed, which computes the corresponding movement increment computed based on Eminence and PreviousEminence. As shown, the process then continues with Block 364.

Block 364 determines if the last movement of the selected tooth changed FirstOrderRotation. If so, then Block 366 is executed, which computes the corresponding movement increment computed based on FirstOrderRotation and PreviousFirstOrderRotation. As shown, the process then continues with Block 368.

Block 368 determines if the last movement of the selected tooth changed Tip. If so, then Block 370 is executed, which computes the corresponding movement increment computed based on Tip and PreviousTip. As shown, the process then continues with Block 372.

Block 372 determines if the last movement of the selected tooth changed Torque. If so, then Block 374 is executed, which computes the corresponding movement increment computed based on Torque and PreviousTorque. As shown, the process then continues with Block 376.

Block 376 determines if the last movement of the selected tooth changed OpposingArchContactOffset. If so, then Block 378 is executed, which computes the corresponding movement increment computed based on OpposingArchContactOffset and PreviousOpposingArchContactOffset. As shown, the process then continues with Block 388 in FIG. 40.

In Block 388, a function is executed to virtually place the selected tooth on the archform. Moving to Block 390, the computer then executes a process to determine if the selected tooth is in collision with neighboring teeth. The following Block 392 determines if there is a change in the collision status of the selected tooth (i.e. does currentlyInCollision=inCollision?) If so, then both the multiplier and currentlyInCollision are negated (Block 394).

Finally, Block 396 determines if either the absolute value of the movement is greater than the tolerance or if the selected tooth is still in collision. If so, then the process reiterates from Block 348 in FIG. 38. If not, the function ends.

Computing a Movement Increment for a Given Tooth Property

Figure 41:
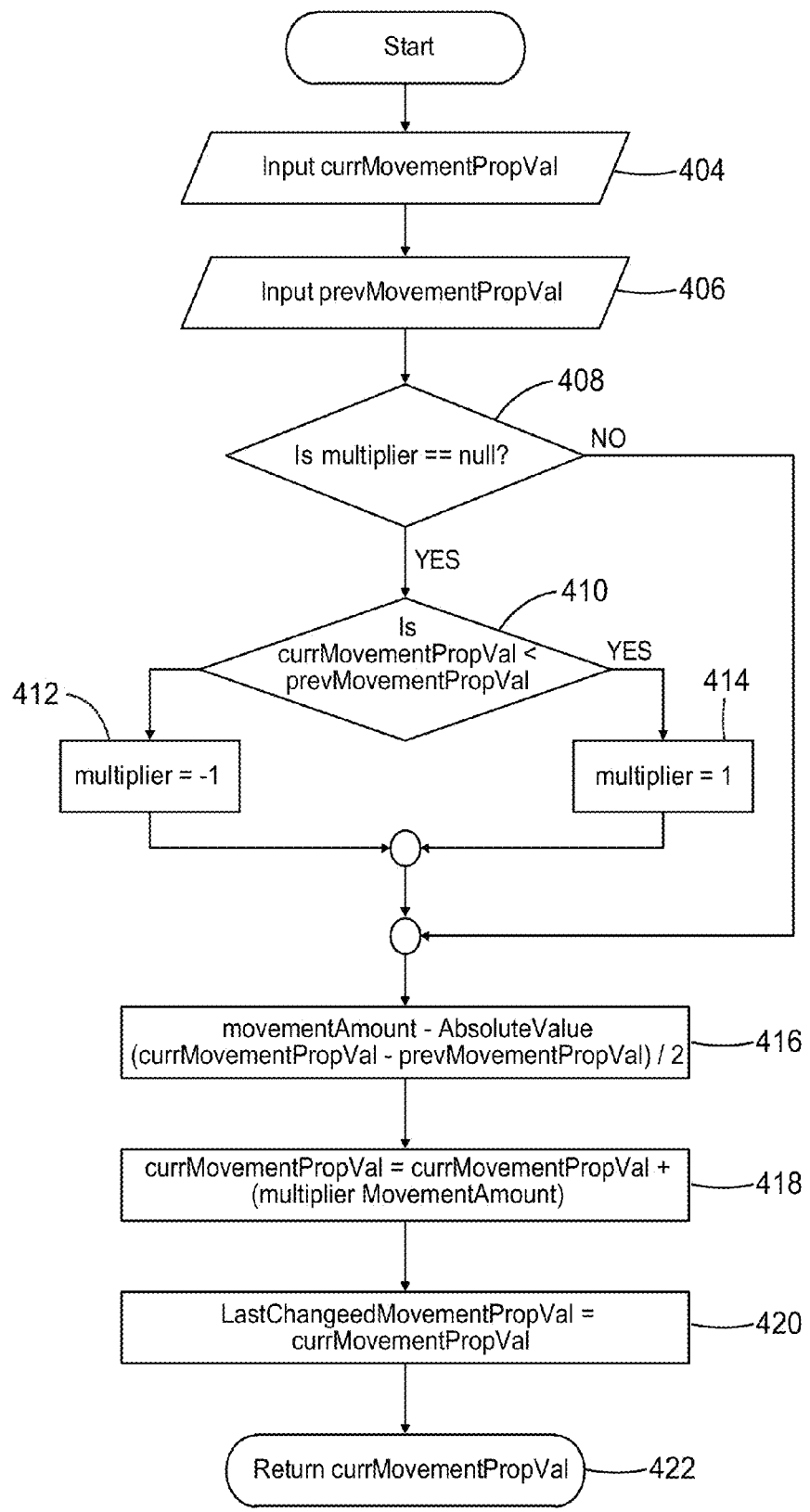
FIG. 41 is a flowchart showing a method of computing a movement increment for a tooth.

FIG. 41 is directed to a function that determines the movement increment used to move the selected tooth out of collision. This function adjusts the movement increment at each iteration of the loop in FIGS. 38-40 such that the selected tooth efficiently converges to a position where it is removed from collision but maintained "in contact" with a neighboring tooth.

The process begins with Blocks 404 and 406, which provide input as to currMovementPropValue and prevMovementPropValue, respectively. These are function parameters that represent the current and previous positions of the selected tooth with respect to the movement of interest.

If multiplier is undeclared (i.e. multiplier is NULL) (Block 408), then the process proceeds directly to Block 416. However, if the multiplier is NULL, then the process proceeds to Block 410 to define this variable. Block 410 determines if the currMovementPropValue is less than prevMovementPropValue. If so, then the multiplier is set to −1 (Block 412) to reverse the direction of movement. Otherwise, the multiplier is set to 1 (Block 414).

Block 416 defines movementAmount as the absolute value of ((currMovementPropVal−PrevMovementPropVal)/2), and Block 418 increments currMovementPropVal by multiplier*movementAmount. Then, in Block 420, LastChangedMovementPropVal is set to currMovementPropVal, thus defining a persistent property of the tooth. Finally, the function ends with Block 422, which returns the new value of currMovementPropVal.

Occlusion Setting

The user proceeds by making adjustments to the tooth surfaces of the dentition surface 100 pursuant to a desired occlusion, as represented by Block 62 in FIG. 1B. Interactions between teeth of opposing arches can be treated similarly to interactions between teeth of the same arch. Many of the basic tools and procedures described above for PLACEMENT OF THE TEETH IN AN ARCHFORM similarly apply; as such, these will not be re-examined here.

In general, setting the occlusion between the upper and lower arches often begins with defining a proper intercuspation of teeth. For example, the orthodontic practitioner may require a Class I molar relationship, where the buccal groove of the lower first molar tooth occludes with the mesiobuccal cusp of the upper first molar tooth. Whether teeth can be guided to a proper molar relationship can depend on the archform, the relationship between the upper and lower arch lengths, the individual tooth coordinate systems (i.e. the location and orientation of each tooth), and the size and shape of the teeth. Once again, the ideal molar relationship may not be immediately possible based on constraints in tooth movement.

In an exemplary embodiment, the user defines an initial arch form, examines arch length for the upper and lower arches, and determines if the desired molar relationship is achievable with the specified constraints. For example, if there is an arch length discrepancy, the user may increase anterior proclination (collective torque of multiple anterior teeth) to change increase the length of upper arch. However, if the orthodontic practitioner prescribes a certain overbite or overjet, the user may be completely constrained from making this compromise. Then need to look at what other variables can be compromised. If the user determines that a required tooth movement is precluded, the user can communicate with orthodontic practitioner to get advice.

The size and shapes of teeth are not immutable. For example, the effects of interproximal reduction can be simulated using an automatic or semi-automatic process. In some embodiments, the user temporarily pins a tooth, such that it stay fixed even when other teeth are adjusted and re-packed. The user can designate the mesial-most teeth in a quadrant as a pinned tooth, and also pin a posterior tooth. The methods described can then be used to pack the remaining teeth within the archform while constrained by the pinned teeth. Then, after defining an archform for the rest of the teeth, can distribute the IPR among the remaining teeth. In one embodiment, the IPR is distributed evenly amongst these remaining teeth. Advantageously, the software can compensate for the change in tooth width as a result of the first order rotation.

Dental Arch Articulation

The orthodontic digital setup can be refined further in virtual dental arch articulation as provided in Block 64 in FIG. 1B. Virtual articulation simulates the temporomandibular joints and the jaws, to which the upper and lower dental arches are attached. This digital representation is useful in reproducing the full range of possible mandibular movements, such as those encountered in chewing motions.

Like the tooth-to-tooth collisions described previously, arch-to-arch collisions can be simulated by applying virtual forces to the teeth. In response to these virtual forces, an arch can be simulated to move in a natural manner that avoids intersection between the upper and lower dental arches while maintaining contact. Advantageously, software can be used to simulate the physical process of setting an occlusion using an articulator.

In some embodiments, collision detection occurs between two monolithic (i.e. unsegmented) dental arches. However, the detection of collision between opposing dental arches can also include detecting whether one or more pairs of opposing teeth are in collision. Alternatively, or in combination, the detection of collision could also include detecting whether one or more teeth in one arch is in collision with any portion of the second arch.

Such a process is described by way of illustration and example in a series of interrelated flowcharts, provided below.

Figure 42:
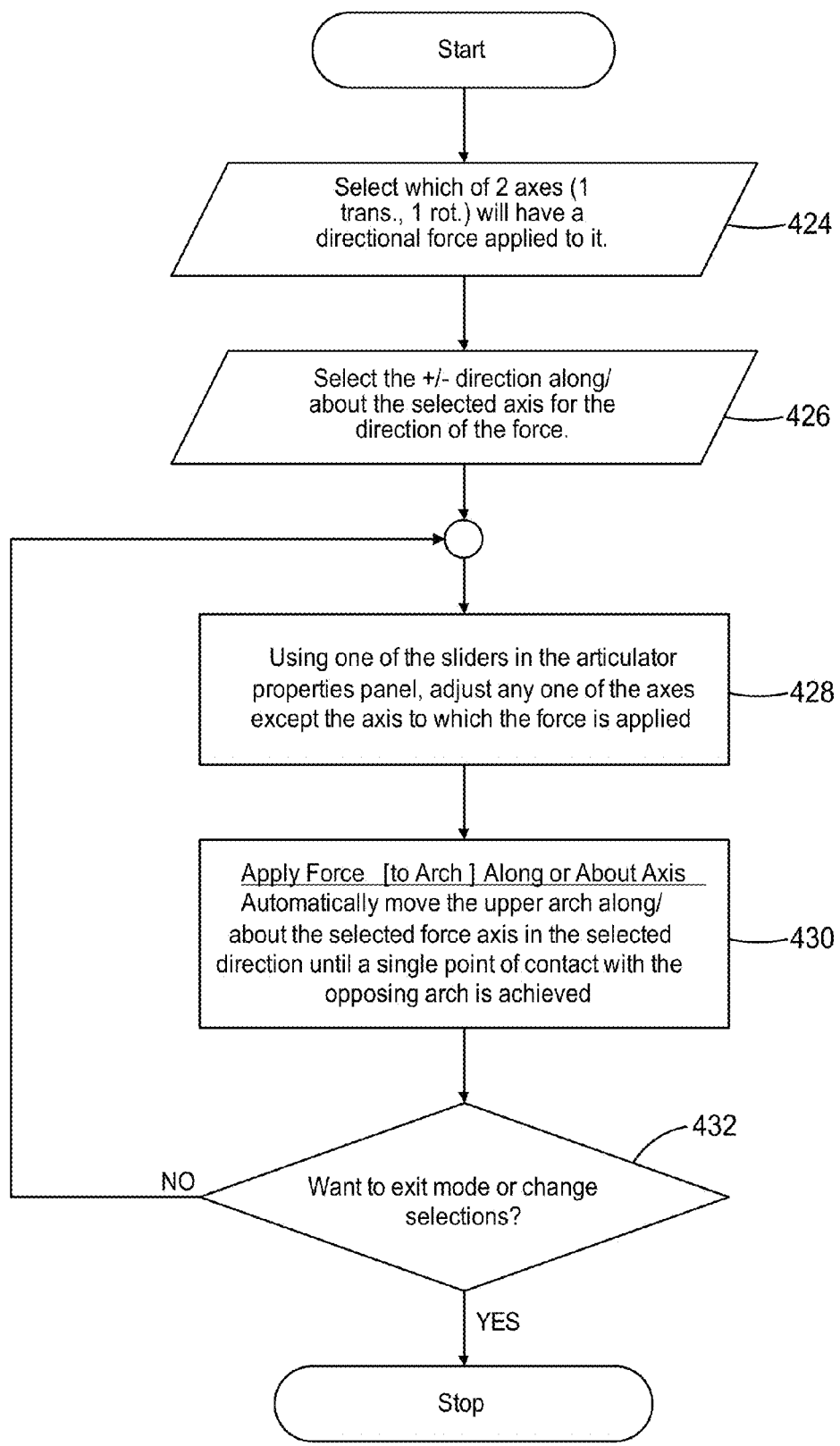
FIG. 42 is a high level flowchart showing a method of collision prevention between dental arches.

Arch-to-Arch Collision Prevention with Applied Force During Virtual Articulation FIG. 42 is a high-level flowchart describing an exemplary process that simulates the movement of a dental arch in response to virtual articulation of upper and lower dental arches. Block 424 provides for the selection of one of two axes for the application of a directional force. Since this process concerns the movement of arches, not individual teeth, two possibilities are provided, one translational and one rotational: 1) along the condyle axis, and 2) about the condyle axis.

In Block 426, the direction of the force along/about the above selected axis is specified. This is provided as either positive (+) or negative (−). In this example, a decrease in the gape angle (closing of the jaws) about the condyle axis is be represented by a negative value. For movements along the condyle axis, a lateral excursion toward the patient's left is defined as negative and a lateral excursion toward the patient's right is defined as positive.

Next, and as provided in Block 428, the user makes an adjustment to any one of the axes except the axis to which the force is applied. In an exemplary embodiment, this adjustment occurs by manipulating a slider in the articulator properties panel of the user interface. Possible choices could include closing the gape, a lateral excursion left, or a lateral excursion right. The upper arch moves by a small increment along/about the manually adjusted axis.

Block 430 is a function that applies force to the arch along or about the axis, and will be later described in greater detail in FIGS. 43-44. Here, the computer automatically moves the upper arch along/about the selected force axis in the selected direction until a single point of contact with the opposing arch is achieved. If any tooth is intersecting an antagonist tooth in the direction of force, the entire arch is first moved back until the intersection is eliminated.

The process then continues to Block 432, where the user is given the option to either exit the current process or change selections. If so, the process ends; otherwise, the process restarts from Block 428.

Application of Forces to Arch Along or about Axis

Figure 43:
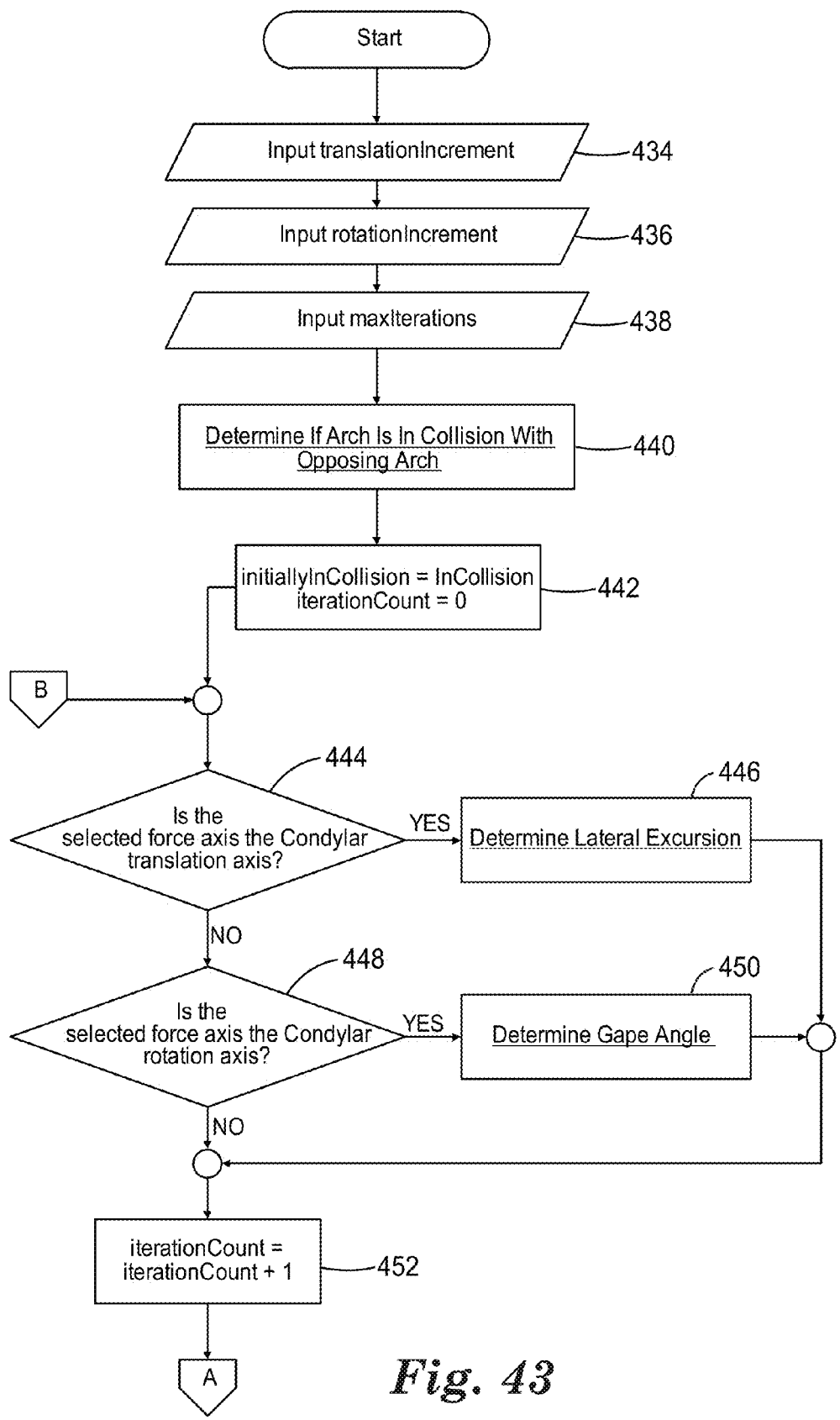
FIGS. 43-44 are a flowchart showing a method of applying force to a dental arch along or about a selected axis.
Figure 44:
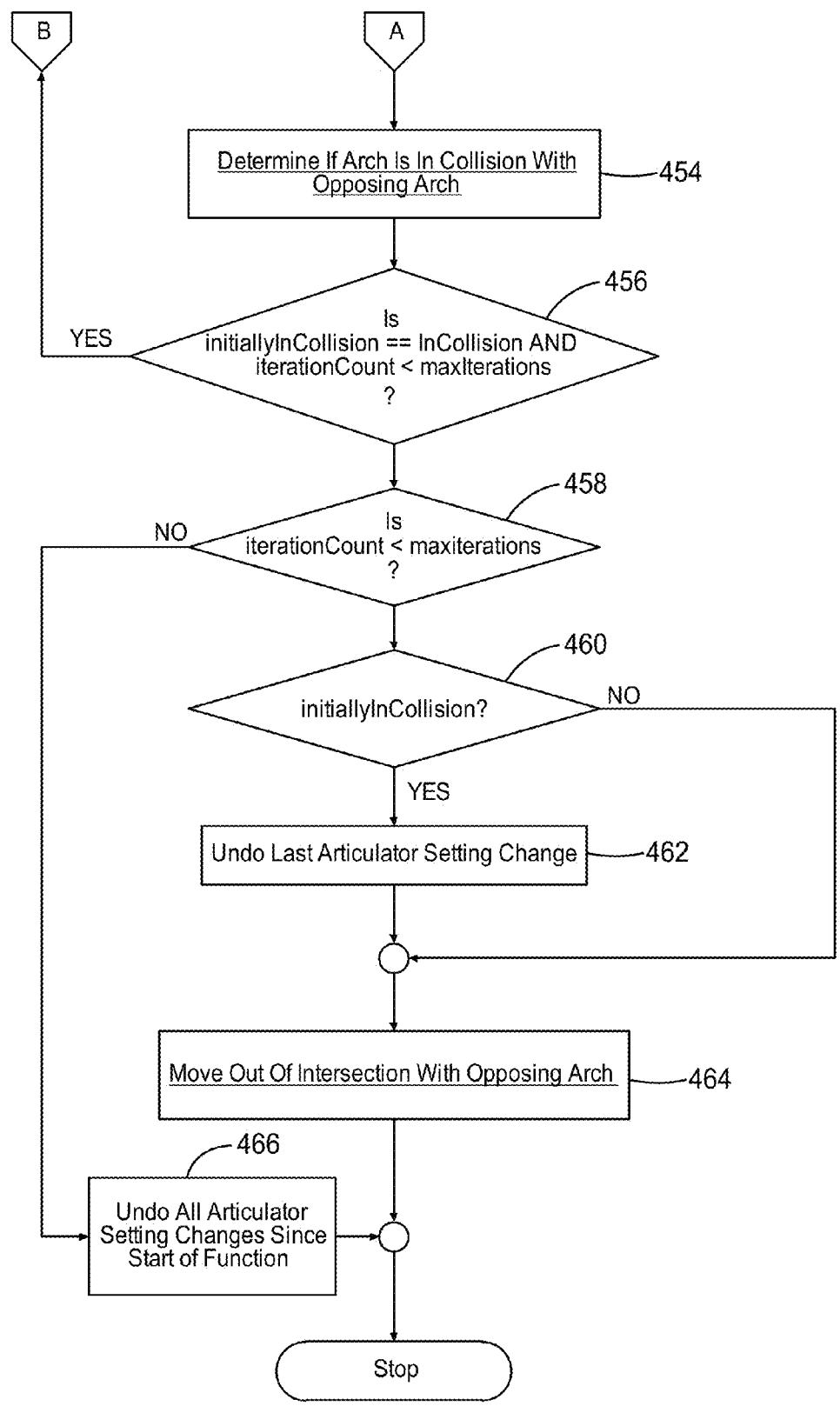

FIGS. 43 and 44 provide a flowchart of an exemplary process by which forces are applied to an arch to provide the desired movement.

The process begins with Block 434 and 436, in which TranslationIncrement and RotationIncrement are provided as inputs; here, these are provided as function parameters. While both variables are indicated, the former is only used for translational axes and the latter is only used for rotational axes. In Block 438, maxIterations is provided as an input. maxIterations sets the maximum number of iterations to prevent run-on arch movements.

Block 440 invokes a function to determine if the selected arch is in collision with the opposing arch and returns either TRUE or FALSE. Block 442 sets the variable initiallyInCollision to inCollision and sets iterationCourt to 0.

Block 444 represents the beginning of a loop that is iterated as long as the collision status of the arch has not changed and the maximum number of iterations has not been reached. If the selected force axis is the condyler translation axis (Block 444), then a function is executed to determine the lateral excursion (Block 446). If the selected force axis is the condyler rotation axis (Block 448), then a function is executed to determine the gape angle (Block 450). Either way, the process continues with Block 452, where iterationCount is incremented by 1.

Continuing with FIG. 44, Block 454 executes a function that determines if the two arches are in collision with each other. If initiallyInCollision is equal to inCollision AND iterationCount<maxIterations (Block 456), then the process returns back to Block 444. Otherwise, it proceeds to Block 458, which determines the reason for termination of the loop. If the loop terminated because the maximum number of iterations was reached, then Block 466 reverses all articulator setting changes since the start of the function and the function ends.

If the loop terminated because of a change in collision state, then the process goes to Block 460, which inquires if initiallyInCollision is TRUE. If so, then just the last articulator setting change is undone (Block 462). Finally, Block 464 executes a function that moves the arch out of intersection with the opposing arch and the function ends. Further details regarding the function of Block 464 will be addressed later in FIGS. 46-48.

Determine if Arch is in Collision with Opposing Arch

Figure 45:
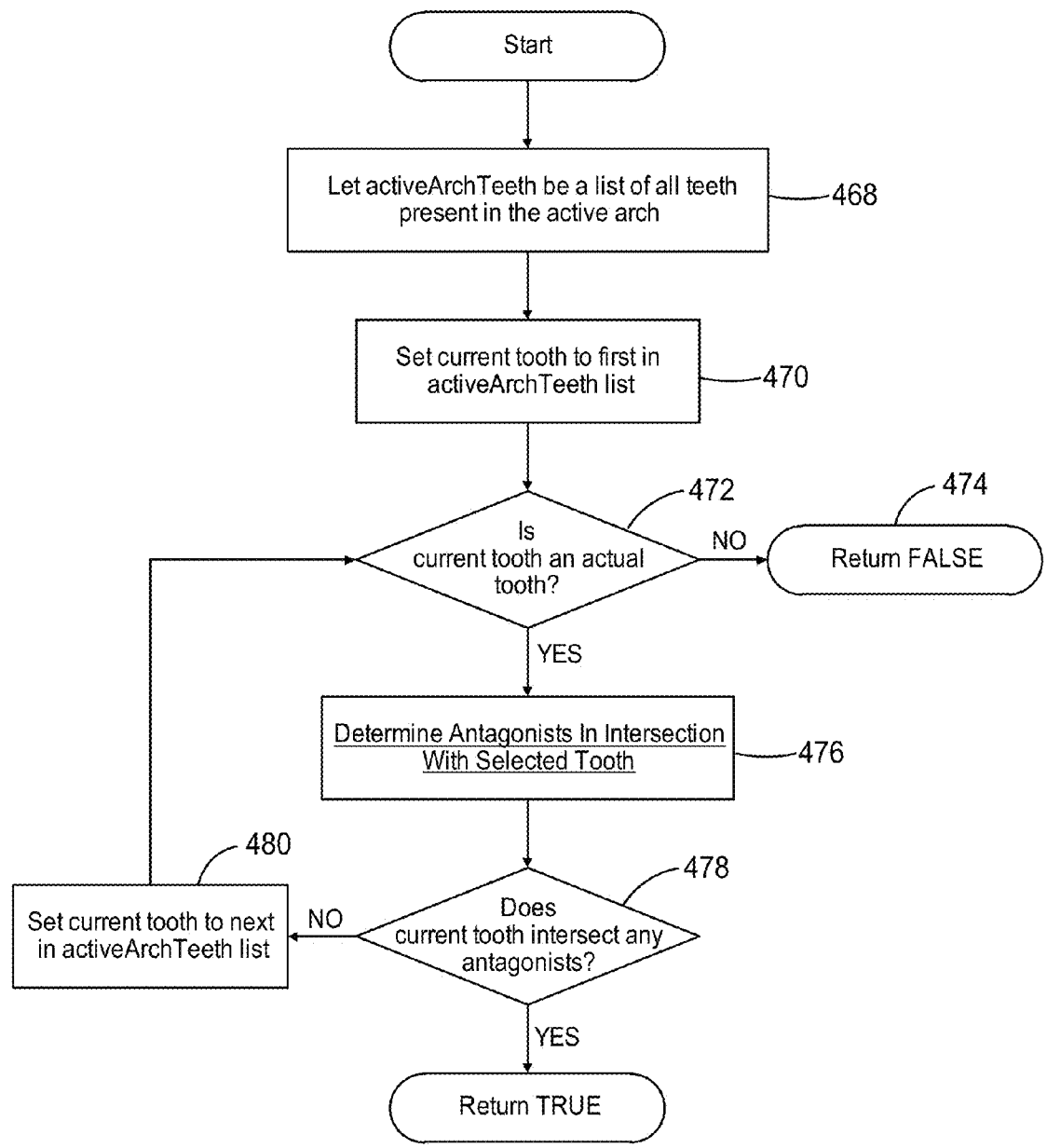
FIG. 45 is a flowchart showing a method of determining if a dental arch is in collision with an opposing dental arch.

FIG. 45 provides a function that searches for tooth-to-tooth collisions to determine if the upper arch is in collision with the lower arch. Initially, Block 468 defines activeArchTeeth as a list of all teeth present in the active arch. Block 470 then defines a current tooth as the first tooth in the activeArchTeeth list.

Block 472 determines if the current tooth is an actual tooth, as opposed to a null value. If not, then the function returns the value FALSE. If so, then the process proceeds with a function to determine antagonist teeth in intersection with the selected tooth (see FIG. 37). Block 478 then determines if the current tooth intersects with any antagonist teeth. If not, then the current tooth is set to the next tooth in the activeArchTeeth list, and the process reiterates from Block 472; otherwise, the function returns the value TRUE.

Move Arch Out of Intersection with Opposing Arch

Figure 46:
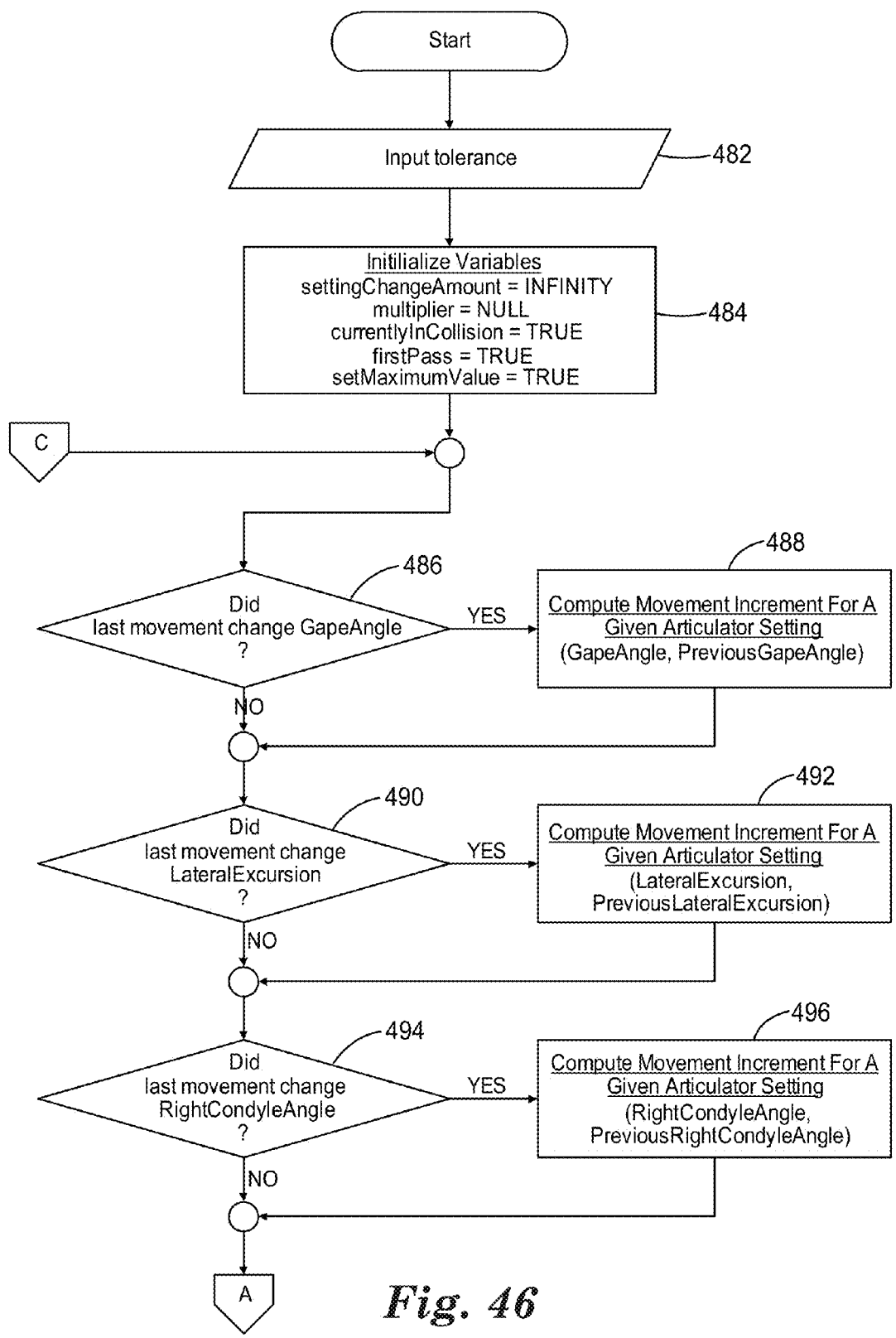
FIGS. 46-48 are a flowchart showing a method of moving a dental arch out of collision with an opposing dental arch.
Figure 47:
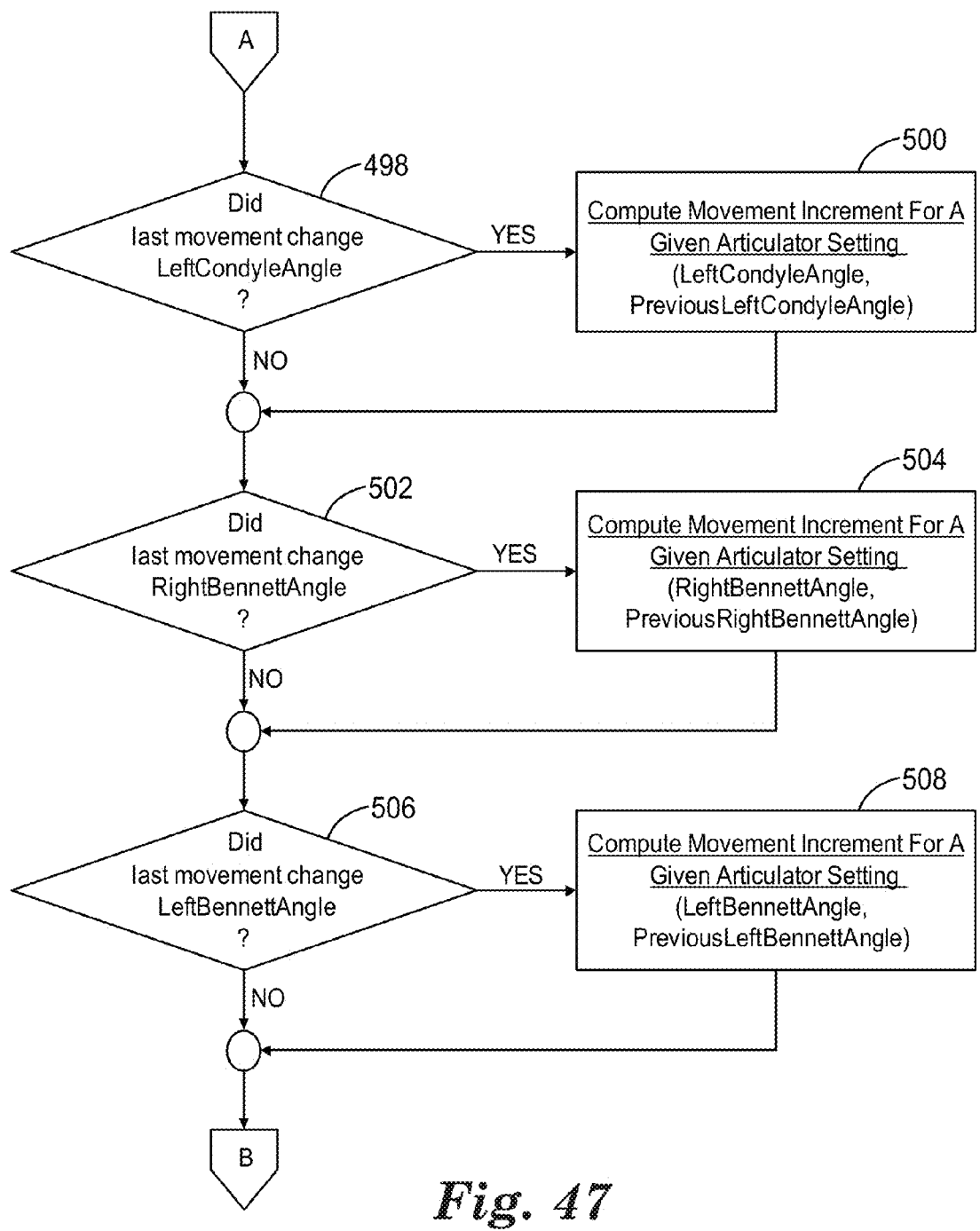
Figure 48:
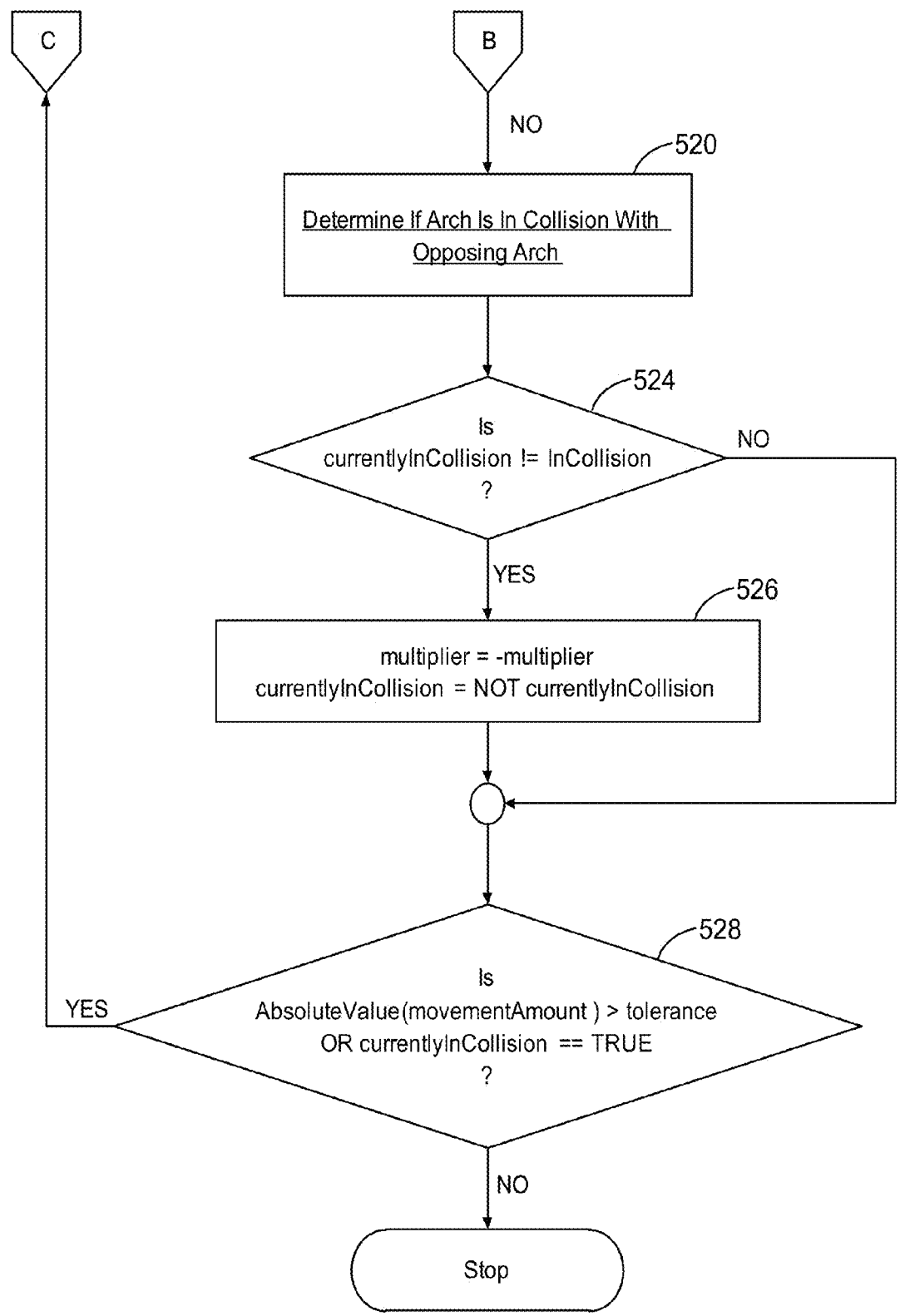

An exemplary process used to move the current arch out of intersection with the opposing arch is provided by a three-part flowchart shown in FIGS. 46-48.

First, a tolerance is provided in Block 482. This is a function parameter and is defined such that contact with the opposing arch occurs within this distance. Certain variables are initialized in Block 484. In this example, settingChangeAmount is set to INFINITY, multiplier is set to NULL, currentlyinCollision is set to TRUE, and setMaximumValue is set to TRUE.

Block 486 is the beginning of an iterative loop that is repeated until contact between upper and lower arches is achieved within the predefined tolerance. Block 486 determines if the last movement of the arch was a change to GapeAngle. If so, then the process goes to Block 483, which executes a function to compute the movement increment for a given articulator setting (addressed later in FIG. 49). In this case, the articulator settings are GapeAngle and PrevGapeAngle. As shown, the process then continues with Block 490.

Block 490 determines if the last movement of the arch was a change in LateralExcursion. If so, then the process goes to Block 492, which executes a function to compute the movement increment for articulator settings LateralExcursion and PrevLateralExcursion. As shown, the process then continues with Block 494.

Block 494 determines if the last movement of the arch was a change in RightCondyleAngle. If so, then the process goes to Block 496, which executes a function to compute the movement increment for articulator settings RightCondyleAngle and PrevRightCondyleAngle. As shown, the process then continues with Block 498 in FIG. 47.

Block 498 determines if the last movement of the arch was a change in LeftCondyleAngle. If so, then the process goes to Block 500, which executes a function to compute the movement increment for articulator settings LeftCondyleAngle and PrevLeftCondyleAngle. As shown, the process then continues with Block 502.

Block 502 determines if the last movement of the arch was a change in RightBennettAngle. If so, then the process goes to Block 504, which executes a function to compute the movement increment for articulator settings RightBennettAngle and PrevRightBennettAngle. As shown, the process then continues with Block 506.

Block 506 determines if the last movement of the arch was a change in LeftBennettAngle. If so, then the process goes to Block 508, which executes a function to compute the movement increment for articulator settings LeftBennettAngle and PrevLeftBennettAngle. As shown, the process then continues with Block 520 in FIG. 48.

Block 520 executes a function that determines if the arch is in collision with the opposing arch (see FIG. 45). Here, if the arches are in collision, then inCollision is set to TRUE; otherwise, inCollision is set to FALSE. Block 522 then determines if the collision status for the arch has changed (i.e. is currentlyinCollision no longer equal to inCollision?). If so, then Block 524 reverses the values of both multiplier and currentlyinCollision.

The process proceeds to Block 526 to determine if point contact may have been established. If the absolute value of movementAmount is greater than the tolerance OR currentlyinCollision is TRUE, then such contact has not been established and the cycle reiterates from Block 486. Otherwise, the process ends.

Compute Movement Increment for a Given Articulator Setting

Figure 49:
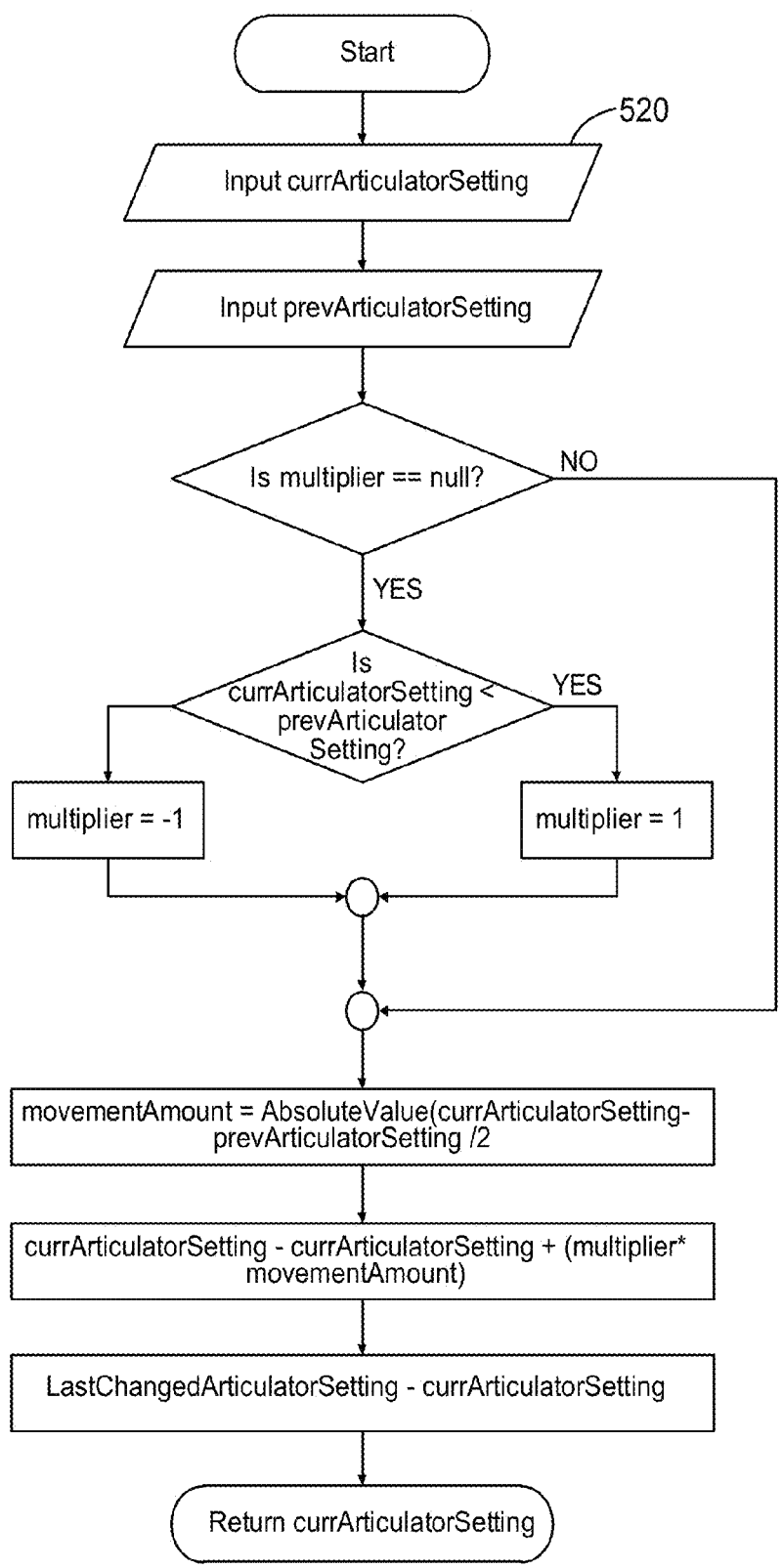
FIG. 49 is a flowchart showing a method of determining a movement increment for an articulated dental arch movement.

FIG. 49 is directed to an exemplary function that determines the movement increment used to move the arch out of collision. This function adjusts the movement increment at each iteration of the loop in FIGS. 46-48 such that the arch efficiently converges to a position where it is removed from collision but maintained in contact with the opposing arch.

Blocks 534 and 536 are function parameters providing the current and previous articulator settings, respectively. Block 538 determines if the multiplier has been declared in the calling function. If not, the multiplier is defined as being either −1 (Block 542) or 1 (Block 544), depending on the relative values of currArticulatorSetting and prevArticulatorSetting (Block 540), thereby indicating the proper direction of movement.

The process then moves to Block 546, which defines the movementAmount as the absolute value of ((currArticulatorSetting−prevArticulatorSetting)/2). Block 548 then increments the current articulator setting by an amount defined by multiplier*movementAmount. Block 550 sets LastChangedArticulatorSetting to currArticulatorSetting, a value which persists as a property of the articulator. Finally, Block returns currArticulatorSetting as an update to the input value of the function.

Figure 50:
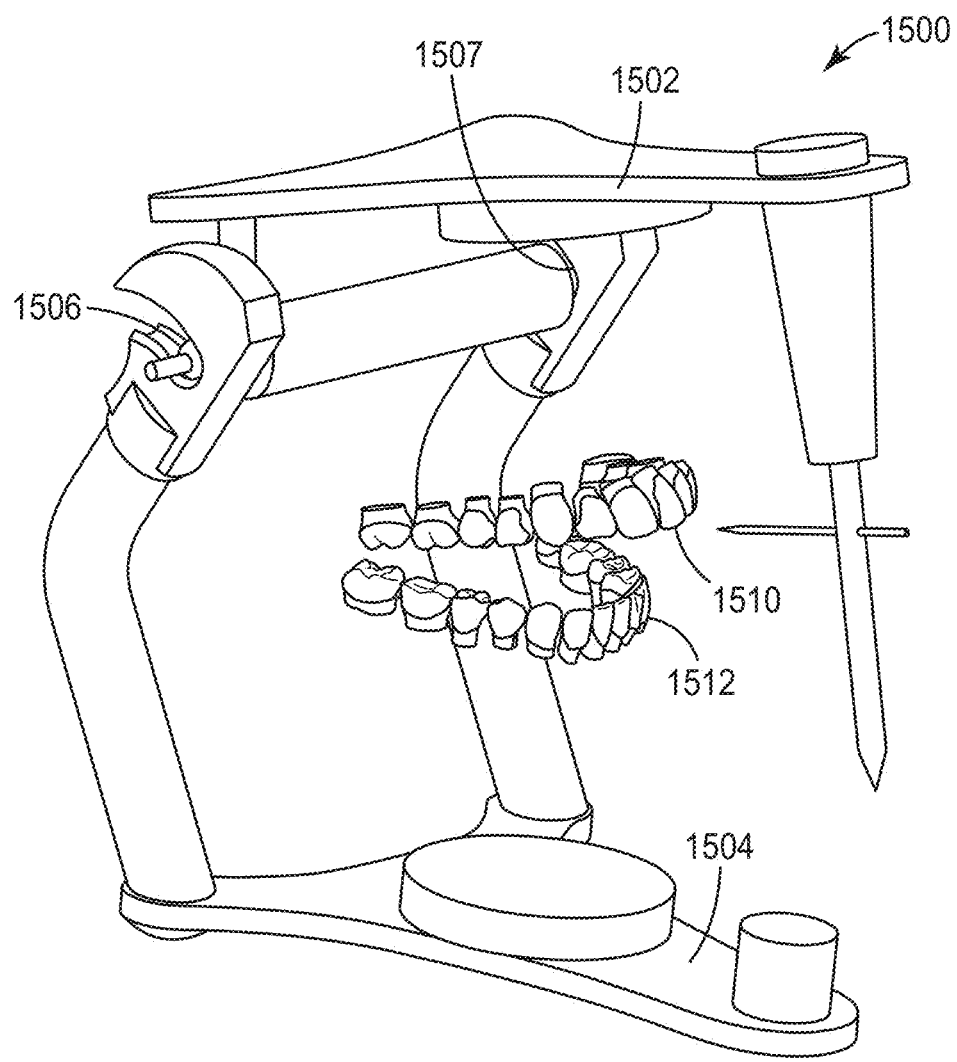
FIG. 50 is a perspective view of a virtual articulator showing the dentition surface of FIGS. 2A-24 in an open gape configuration.
Figure 51:
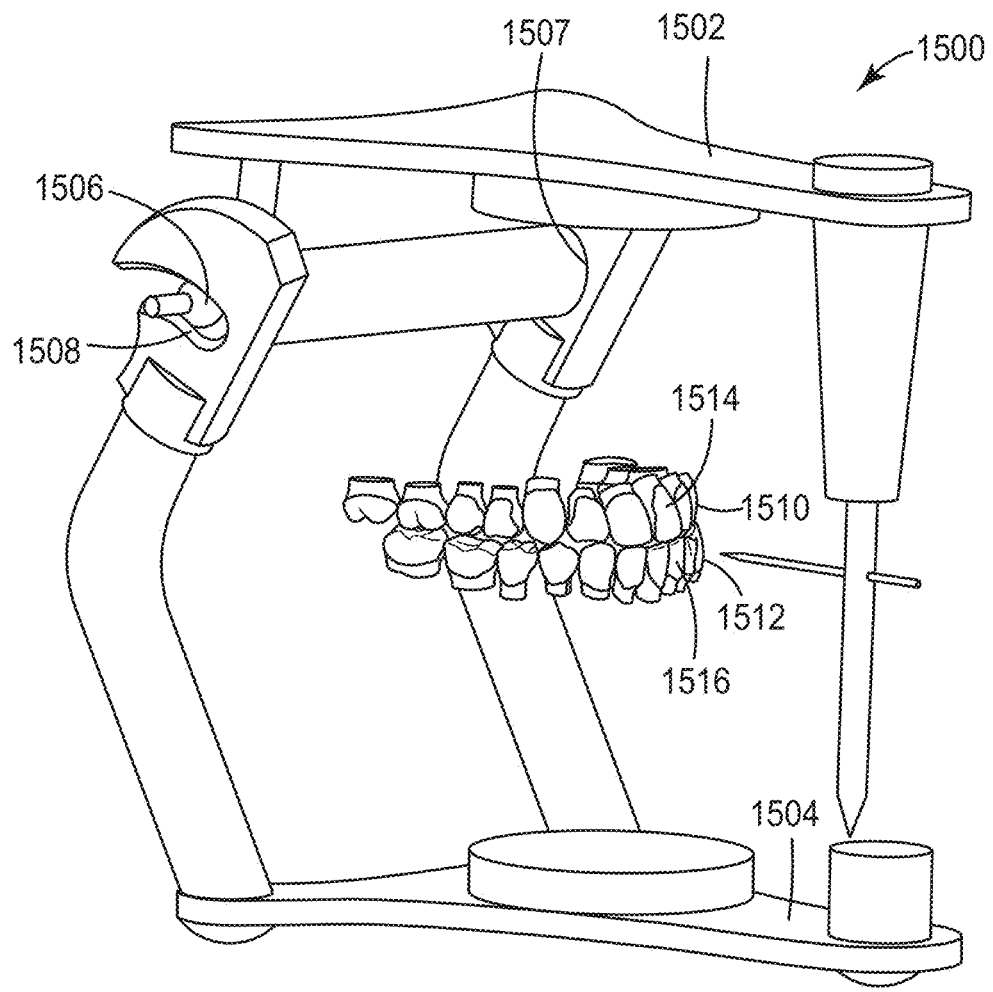
FIG. 51 is a perspective view of a virtual articulator showing the dentition surface of FIGS. 2A-24 in a closed gape configuration.

FIGS. 50 and 51 show a user interface displaying upper and lower arches in a virtual articulator 1500 in open and closed positions, respectively. The articulator 1500 includes an upper section 1502 and a lower section 1504, along with a pair of slidable ball joints 1506,1507 that connect the upper and lower sections 1502,1504 to each other. The joints 1506,1507 each reside in a corresponding pair of grooves 1508 (only one of which is visible in FIGS. 50 and 51) located on the lower section 1504.

Upper and lower arches 1510,1512 of the dentition surface 100 float between the upper and lower sections 1502, 1504. Each of the arches 1510,1512 are virtually associated with the respective sections 1502,1504 such that they move in synchrony with each other.

Because the joints 1506,1507 are situated in the grooves 1508, the upper section 1502 has the freedom to not only pivot between open and closed positions (as defined by the gape angle) but also provide lateral excursion where one arch slides left or right relative to the other arch. In FIG. 51, the joint 1506 has traveled in the distal direction along a portion of the groove 1508, while the opposite joint 1507 remains fully engaged in the mesial end of the opposite groove 1508. As a result the articulator 1500 shows the effect of relative lateral excursion of the lower arch 1512 toward the patient's left against the upper arch 1510.

FIG. 51 shows an advantageous application of the collision detection tool described above under the section "TOOTH PLACEMENT IN ARCHFORM." As the teeth of the lower arch 1512 collide with the teeth of the upper arch 1510, tooth surfaces 1514,1516 are highlighted by suitable color or shading, thereby indicating to the user where interferences occur over a full range of jaw movements.

Described below are further embodiments provided herein:

A) A method of defining a coordinate system for a virtual tooth comprising:

displaying the tooth to a user in a three-dimensional viewing environment;

receiving user input to determine the placement of first and second crosshairs on a view plane such that the crosshairs appear to intersect at a perceived reference point on the tooth;

receiving additional user input to rotate at least one crosshair until either the first crosshair aligns with a perceived occluso-gingival axis of the tooth or the second crosshair aligns with a perceived mesio-distal axis of the tooth;

determining a normal vector for a portion of the tooth surface surrounding the reference point; and computing a coordinate system using the reference point as a position reference and using one of the crosshairs and the normal vector from the tooth surface as an orientation reference.

B) The method of embodiment A, wherein the user input to rotate one or both crosshairs is provided by rotating a scroll wheel of a pointing device.

C) The method of embodiment A, wherein the user input to rotate one or both crosshairs comprises user input to rotate the first crosshair relative to the second crosshair.

D) The method of embodiment C, wherein the user input to rotate the first crosshair relative to the second crosshair is provided by rotating a scroll wheel of a pointing device while in a temporary user input mode.

E) The method of embodiment A, wherein computing a coordinate system further comprises defining the origin of the coordinate system as the perceived reference point on the tooth.

F) The method of embodiment A, wherein computing a coordinate system comprises:

defining a sagittal reference plane based on the intersection of the first crosshair and an eye point of a virtual camera in the viewing environment;

identifying a polyline where the sagittal plane intersects the tooth surface; and defining the origin of the coordinate system as the occlusal-most point of the polyline.

G) The method of embodiment A, wherein determining a normal vector for a portion of the tooth surface surrounding the reference point comprises:

defining an array of points in a plane parallel to the view plane of a virtual camera in the 3D viewing environment;

projecting said points onto the surface of the tooth along a line passing through an eye point of the virtual camera and the reference point of the tooth;

determining additional normal vectors for each projected point at the surface of the tooth; and computing the normal vector based on the average of the additional normal vectors.

H) The method of embodiment G, wherein the array of points lie in a reference plane parallel to the view plane.

I). The method of embodiment A, wherein determining a normal vector for a portion of the tooth surface around the reference point comprises:

identifying a normal vector at the reference point of the tooth;

defining an array of points in a plane that is normal to said normal vector;

projecting said points onto the surface of the tooth along said normal vector;

determining additional normal vectors for each projected point at the surface of the tooth; and computing the normal vector based on the average of the additional normal vectors.

J). The method of embodiment I, wherein a plane parallel to the normal vector at the reference point of the tooth defines the face of a cylinder and the array of points in said plane is bounded by the radius of the cylinder.

K) The method of embodiment A, wherein determining the normal vector comprises:

identifying an initial normal vector at the reference point of the tooth;

defining an array of points lying in a reference plane perpendicular to the initial normal vector;

projecting the array of points onto the tooth along the initial normal vector;

determining additional normal vectors at each projected point on the tooth; and computing the normal vector based on the average of the additional normal vectors.

L) The method of embodiment A, wherein determining the normal vector comprises:

defining a geometric shape enclosing a portion of the tooth surrounding the reference point; and computing the normal vector based on an average normal vector for the enclosed portion of the tooth.

M) The method of embodiment L, wherein the enclosed portion of the tooth is represented by a plurality of polygons and the average normal vector is computed by averaging the normal vectors of the polygons.

N) The method of embodiment L wherein the enclosed portion of the tooth is represented by a plurality of polygons, and the average normal vector is computed by averaging the normal vectors of the polygon vertices.

O) A method of resolving a collision between first and second virtual teeth comprising:

simulating a force applied to the first tooth along or about a first axis;

receiving input directed to movement of the first tooth relative to the second tooth along or about a second axis; and allowing tooth movement in the direction of the input-directed movement while limiting tooth movement in the direction of the applied force based on the collision.

P) The method of embodiment O, wherein the movement of the first tooth along or about the second axis is determined based on user-directed movement.

Q) The method of embodiment O, wherein the input-directed tooth movement comprises a predetermined movement of the first tooth along or about the first axis accompanied by an automatic movement of the first tooth along or about the second axis.

R) The method of embodiment O, wherein the first and second teeth maintain contact with each other during tooth movement.

S) The method of embodiment O, wherein the first and second teeth are in the same arch.

T) The method of embodiment O wherein the first and second teeth are in opposing arches.

U) The method of embodiment T, wherein the relative movement of the first and second teeth is derived from a virtual articulation of the opposing arches.

V) The method of embodiment U, wherein one or both of the first and second axes is a condyle axis.

W) The method of embodiment O, wherein the allowed tooth movement combines translational or rotational components of the first axis with translational or rotational components of the second axis to provide a path of movement that varies in two dimensions simultaneously.

X) The method of embodiment O, wherein the tooth further comprises at least a portion of a natural crown, natural root, artificial crown, veneer, inlay, onlay, implant, bridge, partial denture, or appliance attached to the tooth.

Y) A method of resolving a collision between opposing virtual dental arches comprising:
 simulating a force applied to the first arch along or about a first axis;
 receiving input directed toward movement of the first arch relative to the second arch along or about a second axis; and
 allowing arch movement in the direction of the input-directed movement while limiting arch movement in the direction of the applied force based on the collision.

Z) The method of embodiment Y, wherein the movement of the first arch along or about the second axis is determined based on the user-directed movement.

AA) The method of embodiment Y, wherein the input-directed arch movement comprises a predetermined movement of the first arch along or about the first axis accompanied by an automatic movement of the first arch along or about the second axis.

BB) The method of embodiment Y, wherein the opposing arches maintain contact with each other during the arch movement.

CC) The method of embodiment Y, wherein the relative movement of the first and second arches is derived from a virtual articulation of the opposing arches.

DD) The method of embodiment Y, wherein the simulated application of force occurs along or about a predetermined condyle axis.

EE) The method of embodiment Y, wherein detecting the collision between opposing virtual dental arches comprises detecting whether one or more pairs of opposing teeth are in collision.

FF) The method of embodiment Y, wherein detecting the collision between opposing virtual dental arches comprises detecting whether one or more teeth in the first arch is in collision with any portion of the second arch.

GG) The method of embodiment Y, wherein the allowed arch movement includes translational or rotational components of the first axis and translational or rotational components of the second axis thereby providing a path of movement that varies in two dimensions simultaneously.

A1) A method for recognizing a tooth surface, comprising:
 receiving input specifying a point on a dentition surface;
 deriving an auxiliary surface using the specified point, wherein at least some portions of the dentition surface intersecting the auxiliary surface are defined as part of the tooth surface; and
 analyzing the dentition surface along a plurality of paths outwardly extending from the auxiliary surface along the dentition surface to identify a boundary separating the tooth surface and surrounding dentition surfaces.

A2) A method for recognizing a tooth surface, comprising:
 receiving input specifying a point on a dentition surface;
 deriving a virtual closed surface based on the specified point, wherein portions of the dentition surface located within the closed surface are defined as part of the tooth surface; and
 analyzing the dentition surface along a plurality of paths outwardly extending from the closed surface along the dentition surface to identify a boundary separating the tooth surface and surrounding dentition surfaces.

A3) A method for recognizing a tooth surface, comprising:
 providing a virtual dentition surface representing a shape of at least part of a dentition;
 determining a point on the dentition surface;
 creating a virtual auxiliary surface around the point, such that the auxiliary surface and the dentition surface intersect with each other to form a virtual intersection line on the auxiliary surface and the dentition surface;
 designating a portion of the dentition surface which is enclosed by the intersection line as a partial tooth surface;
 recognizing a tooth boundary on the dentition surface;
 designating the portion of the dentition surface between the tooth boundary and the intersection line as a second partial tooth surface; and
 forming a tooth surface from the first and second partial tooth surfaces.

A4) The method of embodiment A3, wherein automatically recognizing a tooth boundary on the dentition surface comprises analyzing the dentition surface along a plurality of paths outwardly extending from the auxiliary surface.

A5) The method of embodiment A1, A2, or A3, wherein the auxiliary surface is generally a sphere.

A6) The method of embodiment A1 or A2, wherein the surrounding dentition surfaces comprise representations of gingival tissue.

A7) The method of embodiment A1 or A2, wherein the surrounding dentition surfaces comprise representations of one or more adjacent natural or artificial teeth.

A8) The method of embodiment A1 or A2, wherein receiving input comprises receiving user input.

A9) The method of embodiment A5, wherein the sphere is generally symmetrically disposed about the specified point.

A10) The method of embodiment A1, A2, or A3, further comprising receiving input specifying a tooth type, wherein the auxiliary surface has a pre-determined diameter that varies according to the specified tooth type.

A11) The method of embodiment A10, further comprising adjusting the location of the sphere based upon additional input.

A12) The method of embodiment A10, further comprising adjusting the size of the sphere based upon additional input.

A13) The method of embodiment A1, A2, or A3, further comprising displaying the virtual auxiliary surface and dentition surface concurrently.

A14) The method of embodiment A1, A2, or A3 wherein analyzing the dentition surface comprises determining a local concavity of the dentition surface.

A15) The method of embodiment A14, wherein the local concavity is at least partially determined by a numeric characteristic of one or more surface triangles.

A16) The method of embodiment A15, wherein the numeric characteristic is selected from: an angle formed between the surface triangle and a neighboring surface triangle, aspect ratio, internal angle, and area.

A17) The method of embodiment A15, wherein identifying a boundary between the tooth surface and the surrounding dentition surface comprises identifying a chain of contiguous boundary triangles, wherein the numeric characteristic of each boundary triangle falls within a predetermined range of values.

A18) The method of embodiment A17, wherein identifying a boundary between the tooth surface and the surrounding dentition surface comprises fitting a spline to at least some of the boundary surface triangles.

A19) The method of embodiment A17, wherein each boundary triangle has a maximum of two neighboring boundary triangles that also have a numeric characteristic falling within a predetermined range of values.

A20) The method of embodiment A19, wherein the numeric characteristic is an angle formed between the boundary triangle and a neighboring surface triangle.

A21) The method of embodiment A15, wherein identifying a boundary between the tooth surface and the surrounding dentition surface comprises:

proposing a set of surface triangles with a numeric characteristic satisfying a certain threshold value;

determining that the set of surface triangles do not provide an acceptable gingival boundary; and iteratively decreasing the certain threshold value until an acceptable gingival boundary is provided.

A22) An orthodontic appliance made using the method of any of the above embodiments.

A23) A computer program, residing on a tangible storage medium, for recognizing a tooth surface, the program comprising executable instructions operable to cause a computer to:

receive input specifying a point on the dentition surface;

derive a virtual closed surface based on the specified point, wherein portions of the dentition surface located within the closed surface are defined as part of the tooth surface; and analyze the dentition surface along a plurality of paths outwardly extending from the closed surface along the dentition surface to identify a boundary separating the tooth surface and surrounding dentition surfaces.

A24) A computer program, residing on a tangible storage medium, for recognizing a tooth surface, the program comprising executable instructions operable to cause a computer to:

receive input specifying a point on the dentition surface;

derive a virtual closed surface based on the specified point, wherein portions of the dentition surface located within the closed surface are defined as part of the tooth surface; and analyze the dentition surface along a plurality of paths outwardly extending from the closed surface along the dentition surface to identify a boundary separating the tooth surface and surrounding dentition surfaces.

A25) A computer program, residing on a tangible storage medium, for recognizing a tooth surface, the program comprising executable instructions operable to cause a computer to:

provide a virtual dentition surface representing a shape of at least part of a dentition;

determine a point on the dentition surface;

create a virtual auxiliary surface around the point, such that the auxiliary surface and the dentition surface intersect with each other to form a virtual intersection line on the auxiliary surface and the dentition surface;

designate a portion of the dentition surface which is enclosed by the intersection line as a partial tooth surface;

recognize a tooth boundary on the dentition surface;

designate the portion of the dentition surface between the tooth boundary and the intersection line as a second partial tooth surface; and form a tooth surface from the first and second partial tooth surfaces.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

What is claimed is:

1. A computer-implemented method of defining a tooth coordinate system for a virtual tooth comprising:

presenting a dentition surface including the virtual tooth in a user interface of a digital display, the dentition surface representing at least a portion of the patient's dental structure;

receiving point input data that defines a point on the virtual tooth;

receiving axis input data that defines first and second axes associated with the virtual tooth;

using the computer's processor, computing a substantially normal vector for a portion of the tooth surface surrounding the point;

computing the tooth coordinate system based on the axis input and the computed vector;

and receiving modification data for the virtual tooth, the modification data associated with the tooth coordinate system, the modification data including at least one of; and updating the user interface consistent with the modification data.

2. The computer-implemented method of claim 1:

wherein the dentition surface includes a plurality of virtual teeth, and wherein computing the tooth coordinate system is performed on each tooth of the plurality of virtual teeth and further includes the step of creating a movable tooth surface for each tooth of the plurality of virtual teeth.

3. The computer-implemented method of claim 2, and further comprising the step of adjusting the location and orientation of the moveable tooth surfaces to place the tooth surfaces in an archform.

4. The computer-implemented method of claim 1, wherein the modification data comprises input associated with at least one of attaching an appliance to the virtual tooth and transforming the virtual tooth.

5. The computer-implemented method of claim 1, further comprising:

presenting crosshairs in the user interface and, based on input from a user, causing the crosshairs to rotate until the user is satisfied with the orientation of the crosshairs relative to the virtual tooth, and wherein the basis of the resulting rotated crosshairs comprises the axis input.

6. The computer-implemented method of claim 1, further comprising displaying visual indicia associated with the coordinate system in the user interface.

7. The computer-implement method of claim 1, and further comprising receiving a digital dentition model of a patient's dental arrangement, the model comprising at least one virtual tooth representing the patient's actual tooth.

8. The computer implemented method of claim 1, wherein receiving point input data comprises receiving a facial axis (FA) point on the tooth surface.

9. The computer implement method of claim 1, wherein computing a substantially normal vector for a portion of the tooth surface surrounding the point comprises sampling a plurality of points within a geometric shape enclosing a portion of the tooth around the reference point, finding a normal vector for each of the plurality of points, and averaging all normal vectors to find the substantially normal vector at the facial surface of the tooth.

10. A computer-implemented method of defining a tooth coordinate system comprising:
   receiving a digital dentition model of a patient's dental arrangement, the model comprising a virtual tooth representing the patient's actual tooth;
   presenting the virtual tooth in a user interface of a digital display;
   receiving point input data that defines a reference point on the virtual tooth;
   receiving axis input data that defines a first axis associated with the virtual tooth;
   using the computer's processor, computing a substantially normal vector for a portion of the tooth surface surrounding the reference point; and
   computing the tooth coordinate system based on the axis input and the computed vector; and
   and receiving modification data for the virtual tooth, the modification data associated with the tooth coordinate system; and
   updating the user interface consistent with the modification data.

11. The computer-implemented method of claim 10, wherein receiving axis input data further comprises receiving axis input data that defines a second axis associated with the virtual tooth.

12. The computer-implement method of claim 10, wherein the digital dentition model includes a plurality of virtual teeth, and wherein computing the tooth coordinate system is performed on each tooth of the plurality of virtual teeth and further includes the step of creating a movable tooth surface for each tooth of the plurality of virtual teeth, and wherein the method further comprises the step of adjusting the location and orientation of the moveable tooth surfaces to place the moveable tooth surfaces in an archform.

13. A computer-implemented method of defining a tooth coordinate system comprising:
   providing a digital dentition model of a patient's dental arrangement, the model comprising at least one virtual tooth representing the patient's actual tooth;
   presenting the virtual tooth in a user interface of a digital display;
   receiving point input data that defines a point on the virtual tooth;
   receiving axis input data that defines a first axis associated with the virtual tooth;
   using the computer's processor, computing a substantially normal vector for a portion of the tooth surface surrounding the point;
   computing the tooth coordinate system based on the axis input and the computed vector, the tooth coordinate system defining six degrees of freedom for movement of the virtual tooth; wherein computing a substantially normal vector for a portion of the tooth surface surrounding the point comprises sampling a plurality of points within a geometric shape enclosing a portion of the tooth around the reference point, finding a normal vector for each of the plurality of points, and averaging all normal vectors to find the substantially normal vector at the facial surface of the tooth; and
   and receiving modification data for the virtual tooth, the modification data including movement of the virtual tooth surface within the six degrees of freedom defined by the tooth coordinate system; and
   updating the user interface consistent with the modification data.

14. The computer-implemented method of claim 13, wherein receiving axis input data further comprises receiving axis input data that defines a second axis associated with the virtual tooth.

15. The computer-implemented method of claim 14: wherein the digital dentition model includes a plurality of virtual teeth, and wherein computing the tooth coordinate system is performed on each tooth of the plurality of virtual teeth and further includes the step of creating a movable tooth surface for each tooth of the plurality of virtual teeth, and wherein the method further comprises the step of adjusting the location and orientation of the moveable tooth surfaces to place the moveable tooth surfaces in an archform.

16. The computer implemented method of claim 15, wherein adjusting the location and orientation of the moveable tooth surfaces to place the moveable tooth surfaces in an archform comprises following one or more quantitative rules.

17. The computer implemented of claim 16, wherein one or more quantitative rules includes the closure of all spaces within the archform.

18. The computer implemented method of claim 17, and further comprising receiving one or more specified constraints on the position within the archform of at least one tooth of the plurality of virtual teeth.

19. The computer-implemented method of claim 13, further comprising:
   presenting crosshairs in the user interface and, based on input from a user, causing the crosshairs to rotate until the user is satisfied with the orientation of the crosshairs relative to the virtual tooth, and wherein the basis of the resulting rotated crosshairs comprises the axis input.

20. The computer implemented method of claim 13, wherein receiving point input data comprises receiving a facial axis (FA) point on the tooth surface.

* * * * *

UNITED STATES PATENT AND TRADEMARK OFFICE
CERTIFICATE OF CORRECTION

PATENT NO.        : 9,622,835 B2                        Page 1 of 1
APPLICATION NO.   : 14/528966
DATED             : April 18, 2017
INVENTOR(S)       : Peter See It is certified that error appears in the above-identified patent and that said Letters Patent is hereby corrected as shown below:

On the Title Page

Page 2, under "Related U.S. Application Data"
Item (60) delete "61/444,644" and insert -- 61/444,664 --, therefor.

In the Claims

Column 32
Line 27, in Claim 2, delete "claim 1:" and insert -- claim 1, --, therefor.
Line 53, in Claim 7, delete "-implement" and insert -- -implemented --, therefor.
Line 60, in Claim 9, delete "implement" and insert -- implemented --, therefor.

Column 33
Line 16-17 (approx.), in Claim 10, delete "and and" and insert -- and --, therefor.
Line 26, in Claim 12, delete "-implement" and insert -- -implemented --, therefor.

Column 34
Line 8-9 (approx.), in Claim 13, delete "and and" and insert -- and --, therefor.
Line 19 (approx.), in Claim 15, delete "claim 14:" and insert -- claim 1, --, therefor.
Line 34 (approx.), in Claim 17, after "implemented" insert -- method --.

Signed and Sealed this
Twenty-seventh Day of March, 2018

Andrei Iancu
*Director of the United States Patent and Trademark Office*